(12) United States Patent  
Faller et al.

(10) Patent No.: US 8,834,518 B2  
(45) Date of Patent: Sep. 16, 2014

(54) ELECTROSURGICAL CUTTING AND SEALING INSTRUMENTS WITH CAM-ACTUATED JAWS

(75) Inventors: Craig N. Faller, Milford, OH (US); Matthew C. Miller, Cincinnati, OH (US); Omar J. Vakharia, Cincinnati, OH (US); Robert J. Laird, Morrow, OH (US); Gavin M. Monson, Oxford, OH (US); John V. Hunt, Cincinnati, OH (US); Richard W. Timm, Cincinnati, OH (US); David A. Witt, Maineville, OH (US); Zhifan F. Huang, Mason, OH (US); Timothy G. Dietz, Terrace Park, OH (US); Jeffrey L. Aldridge, Lebanon, OH (US); Mary E. Mootoo, Cincinnati, OH (US); Raymond M. Banks, Cupertino, CA (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 710 days.

(21) Appl. No.: 12/758,253

(22) Filed: Apr. 12, 2010

(65) Prior Publication Data

US 2011/0251612 A1  Oct. 13, 2011

(51) Int. Cl.
*A61B 17/28* (2006.01)
*A61B 18/14* (2006.01)

(52) U.S. Cl.
USPC .......................................................... 606/205

(58) Field of Classification Search
USPC ...................................... 606/51, 52, 205–207
See application file for complete search history.

(56) References Cited

U.S. PATENT DOCUMENTS

| 2,366,274 A | 1/1945 | Luth et al. |
| 2,458,152 A | 1/1949 | Eakins |
| 2,510,693 A | 6/1950 | Green |
| 3,166,971 A | 1/1965 | Stoecker |

(Continued)

FOREIGN PATENT DOCUMENTS

| DE | 20004812 U1 | 9/2000 |
| DE | 10201569 A1 | 7/2003 |

(Continued)

OTHER PUBLICATIONS

International Search Report for PCT/US2011/031147, Nov. 9, 2011 (7 pages).

(Continued)

*Primary Examiner* — Michael Peffley

(57) ABSTRACT

Various embodiments are directed to a surgical instrument comprising, a shaft, and an end effector. The shaft may be coupled to the handle and may extend distally along a longitudinal axis. The end effector may be positioned at a distal end of the shaft and may comprise first and second jaw members and a reciprocating member. The first and second jaw members may define first and second longitudinal slots. One or both of the jaw members may be pivotable relative to the other about a pivot point. The reciprocating member may be translatable distally and proximally parallel to the longitudinal axis and through the first and second longitudinal slots. A distal portion of the reciprocating member may define a blade. The instrument may comprise an overtube translatable distally to exert a force on a portions of the first and second jaw members tending to close the first and second jaw members.

20 Claims, 49 Drawing Sheets

(56) References Cited

U.S. PATENT DOCUMENTS

| | | |
|---|---|---|
| 3,580,841 A | 5/1971 | Cadotte et al. |
| 3,703,651 A | 11/1972 | Blowers |
| 4,005,714 A | 2/1977 | Hiltebrandt |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,545,926 A | 10/1985 | Fouts, Jr. et al. |
| 4,582,236 A | 4/1986 | Hirose |
| 4,761,871 A | 8/1988 | O'Connor et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,205,459 A | 4/1993 | Brinkerhoff et al. |
| 5,285,945 A | 2/1994 | Brinkerhoff et al. |
| 5,309,927 A | 5/1994 | Welch |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,624,452 A | 4/1997 | Yates |
| 5,647,871 A | 7/1997 | Levine et al. |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 * | 12/2002 | Truckai et al. ............... 606/51 |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,267,685 B2 | 9/2007 | Butaric et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,510,107 B2 | 3/2009 | Timm et al. |
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |

(56) References Cited

U.S. PATENT DOCUMENTS

| | | |
|---|---|---|
| 7,776,037 B2 | 8/2010 | Odom |
| 7,780,663 B2 | 8/2010 | Yates et al. |
| 7,784,663 B2 | 8/2010 | Shelton, IV |
| 7,815,641 B2 | 10/2010 | Dodde et al. |
| 7,819,298 B2 | 10/2010 | Hall et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,981,113 B2 | 7/2011 | Truckai et al. |
| 8,070,036 B1 | 12/2011 | Knodel et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 * | 8/2012 | Bucciaglia et al. .............. 606/51 |
| 8,298,232 B2 | 10/2012 | Unger |
| 2002/0165541 A1 | 11/2002 | Whitman |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251613 A1 | 10/2011 | Guerra et al. |
| 2011/0264093 A1 | 10/2011 | Schall |
| 2011/0276057 A1 | 11/2011 | Conlon et al. |
| 2011/0282339 A1 | 11/2011 | Weizman et al. |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |
| 2012/0150176 A1 | 6/2012 | Weizman |

FOREIGN PATENT DOCUMENTS

| | | |
|---|---|---|
| EP | 0630612 A1 | 12/1994 |
| EP | 0705571 A1 | 4/1996 |
| EP | 0640317 B1 | 9/1999 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |

(56) References Cited

FOREIGN PATENT DOCUMENTS

| | | |
|---|---|---|
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/059741 A1 | 5/2009 |
| WO | WO 2009/082477 A2 | 7/2009 |
| WO | WO 2010/017266 A1 | 2/2010 |
| WO | WO 2010/104755 A1 | 9/2010 |
| WO | WO 2011/089717 A1 | 7/2011 |

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1..., accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.

International Preliminary Report on Patentability for PCT/US2011/031147, Oct. 16, 2012 (10 pages).

Wright, et al., "Time-Temperature Equivalence of Heat-Induced Changes in Cells and Proteins," Feb. 1998. ASME Journal of Biomechanical Engineering, vol. 120, pp. 22-26.

U.S. Appl. No. 13/221,410, filed Aug. 30, 2011.
U.S. Appl. No. 13/189,169, filed Jul. 22, 2011.

\* cited by examiner

ELECTROSURGICAL CUTTING AND SEALING INSTRUMENTS WITH CAM-ACTUATED JAWS

BACKGROUND

Various embodiments are directed to electrosurgical cutting and sealing instruments with cam-actuated jaws that may be used, for example, in open and minimally invasive surgical environments.

Minimally invasive procedures are desirable because such procedures can reduce pain and provide relatively quick recovery times as compared to conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices (such as end effectors for creating energy-induced tissue welds) are inserted into a patient through trocars placed through the body wall. Still less invasive treatments include those that are performed through insertion of an endoscope through a natural body orifice to a treatment region. Examples of this approach include, but are not limited to, cystoscopy, hysteroscopy, esophagogastroduodenoscopy, and colonoscopy.

Many of these procedures employ a flexible endoscope during the procedure. Flexible endoscopes often have a flexible, steerable articulating section near the distal end that can be controlled by the clinician by utilizing controls at the proximal end. Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 to 3.7 mm for the purpose of introducing and removing medical devices and other accessory devices to perform diagnosis or therapy within the patient. For example, some end effectors are used to create an energy-induced weld or seal. Certain specialized endoscopes or steerable overtubes are available, such as large working channel endoscopes having a working channel of 5 mm, or larger, in diameter, which can be used to pass relatively large accessories, or to provide capability to suction large blood clots. Other specialized endoscopes include those having two or more working channels.

A common task both in minimally invasive and open surgical environments is to grasp, cut and fasten tissue while leaving the cut ends hemostatic (e.g., not bleeding). For example, it is often desirable to cut and seal bodily lumens, such as individual blood vessels or tissue including various vasculature. When sealing a fluid-carrying bodily lumen, it is often necessary for the seal to have sufficient strength to prevent leakage of the fluid, which may exert considerable fluid pressure.

Instruments exist for simultaneously making a longitudinal incision in tissue and fastening the tissue on opposing sides of the incision. Such instruments commonly include an end effector having a pair of cooperating jaw members that, if the instrument is intended for minimally invasive applications, are capable of passing through a cannula passageway or endoscopic working channel. In use, the clinician is able to close the jaw members to clamp the tissue to be cut. A reciprocating cutting instrument (or knife) is drawn distally along the jaw members to transect the clamped tissue. Simultaneously, a fastening mechanism fastens the cut ends of the tissue on opposing sides of the incision. Known fastening mechanisms include staples, sutures or various instruments utilizing energy sources. For example, various energy sources such as radio frequency (RF) sources, ultrasound sources and lasers have been developed to coagulate, seal or join together tissue volumes.

SUMMARY

Various embodiments are directed to a surgical instrument comprising an handle, a shaft, an end effector, and a reciprocating member. The shaft may be coupled to the handle and may extend distally along a longitudinal axis. The end effector may be positioned at a distal end of the shaft and may comprise first and second jaw members. The first and second jaw member may, respectively, define first and second longitudinal slots. Further, the second jaw member may be pivotable towards the first jaw member about a pivot point and comprising a cam pin positioned offset from the pivot point. The reciprocating member may be translatable distally and proximally parallel to the longitudinal axis through the first longitudinal slot and the second longitudinal slot. A distal portion of the reciprocating member may define a blade. The reciprocating member may define a cam slot for receiving the cam pin. Distal motion of the reciprocating member may exert a force on the cam pin such that the second jaw member pivots towards the first jaw member, and proximal motion of the reciprocating member exerts a force on the cam pin such that the second jaw member pivots away from the first jaw member.

Also, various embodiments are directed to a surgical instrument comprising a handle, a shaft, an end effector, a reciprocating member and an overtube. The shaft may be coupled to the handle and may extend distally along a longitudinal axis. The end effector may be positioned at a distal end of the shaft and may comprise first and second jaw members. The first and second jaw member may, respectively, define first and second longitudinal slots. Further, the first and second jaw members may be pivotable relative to one another about a pivot point and may comprise first and second cam portions positioned proximally from the respective pivot points. The reciprocating member may be translatable distally and proximally parallel to the longitudinal axis through the first longitudinal slot and the second longitudinal slot. A distal portion of the reciprocating member may define a blade. The overtube may be positioned over the shaft and may be translatable distally toward the pivot point. The overtube may also be configured to contact the first and second cam portions as it translates distally to apply a force on the first and second cam portions tending to close the first and second jaw members.

In addition, various embodiments are directed to a surgical instrument comprising a handle, a shaft, a reciprocating member, and an end effector. The shaft may be coupled to the handle and may extend distally along a longitudinal axis. The end effector may be positioned at a distal end of the shaft and may comprise first and second jaw members. The first and second jaw members may, respectively, define first and second longitudinal slots. The second jaw member may be pivotable relative to the first jaw member about the pivot point. The reciprocating member may comprise an I-beam member translatable distally and proximally relative to the longitudinal axis through the first longitudinal slot and the second longitudinal slot; and a blade member translatable distally and proximally separately from the I-beam member.

FIGURES

Various features of the embodiments described herein are set forth with particularity in the appended claims. The various embodiments, however, may be understood in accordance with the following description taken in conjunction with the accompanying drawings as follows.

DESCRIPTION

Figure 1:
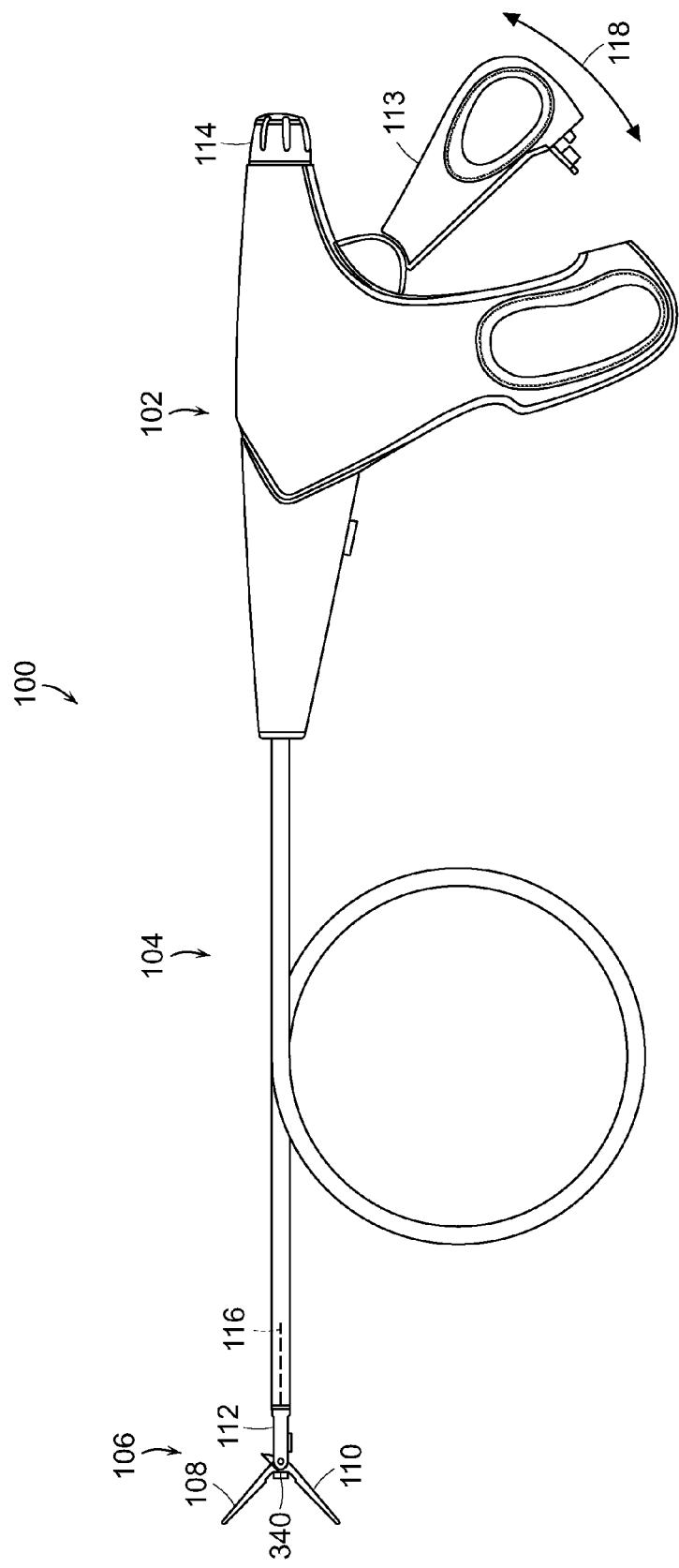
FIG. 1 illustrates one embodiment of a transection and sealing instrument, which may be used, for example, with an endoscope.

Various embodiments are directed to electrosurgical devices for cutting and sealing, for example, cutting and sealing a bodily lumen. According to various embodiments, the electrosurgical devices may comprise a cam-actuated end effector. The cam-actuated end effector may comprise a pair of jaw members and a reciprocating member that may be translatable distally through the jaw members to provide a clamping force tending to force the jaw members together and to transect tissue between the jaw members with a sharpened leading edge. The jaw members may comprise electrodes and/or another electrically active surface for sealing tissue (e.g., tissue that has been severed). Some embodiments of the end effectors may be bilateral (both jaw members are pivotable) or unilateral (only one jaw member is pivotable).

According to various embodiments, the reciprocating member may define a cam slot configured to receive a cam pin coupled to a movable jaw member. Distal and proximal movement of the reciprocating member may cause the cam pin to translate within the cam slot, which may, in turn, cause the movable jaw member to pivot from an open position (e.g., proximal position of the reciprocating member) to a closed (e.g., distal position of the reciprocating member). In embodiments where two jaw members are movable, both jaw members may comprise a cam pin and the reciprocating member may define a pair of cam slots or grooves. The cam-actuated nature of the jaw member or members may increase the acuity of the instrument and allow the clinician to increase the force with which the jaw members are opened. This may make the surgical instrument useful for dissecting as well as for cutting and sealing.

According to various embodiments an end effector may comprise a pair of movable jaw members pivotable about a pivot pin or other pivot point. The jaw members may comprise a cam portion proximal of the pivot point. Each cam portion may define a cam slot. A shuttle may comprise one or more cam pins received within the cam slots. Distal and proximal movement of the shuttle may cause the cam pin or pins to slide within the respective cam slots of the jaw members. This may, in turn, cause the jaw members to open and close. In some embodiments, an overtube may be provided. The overtube may extend distally and contact the cam portions of the jaw members, forcing them towards a longitudinal axis of the end effector.

According to various embodiments, the reciprocating member of any of the end effectors described above may comprise an I-beam member and a blade member. The I-beam member may define a slot for receiving the blade member such that the blade member may translate distally and proximally relative to the I-beam member. In use, the I-beam member may be translated distally separately from the blade member. In this way, the I-beam member may act to close the jaw members, and/or to provide a clamping force tending to force the jaw members together without the blade member extending to transect tissue or material present between the jaw members. The blade member may then be separately extended to transect the tissue or material. In this way, the end effector may be used for grasping as well as for cutting and sealing.

FIG. 1 illustrates one embodiment of a transection and sealing instrument 100. The instrument 100 may be used with an endoscope, laparoscope, or any other suitable introduction device. According to various embodiments, the transection and sealing instrument 100 may comprise a handle assembly 102, a shaft 104 and an end effector 106. The shaft 104 may be rigid (e.g., for laparoscopic application and/or open surgical application) or flexible, as shown, (e.g., for endoscopic application). In various embodiments, the shaft 104 may comprise one or more articulation points (e.g., in embodiments where the shaft 104 is rigid). The end effector 106 may comprise a first jaw member 108 and a second jaw member 110. The first jaw member 108 and second jaw member 110 may be connected to a clevis 112, which, in turn, may be coupled to the shaft 104. In various embodiments, as illustrated below, the jaw members 108, 110 may be directly coupled to the shaft 104 and the clevis 112 may be omitted. As illustrated in FIG. 1, the end effector 106 is shown with the jaw members 108, 110 in an open position. A reciprocating blade/I-beam member 340 is illustrated between the jaw members 108, 110.

Figure 2:
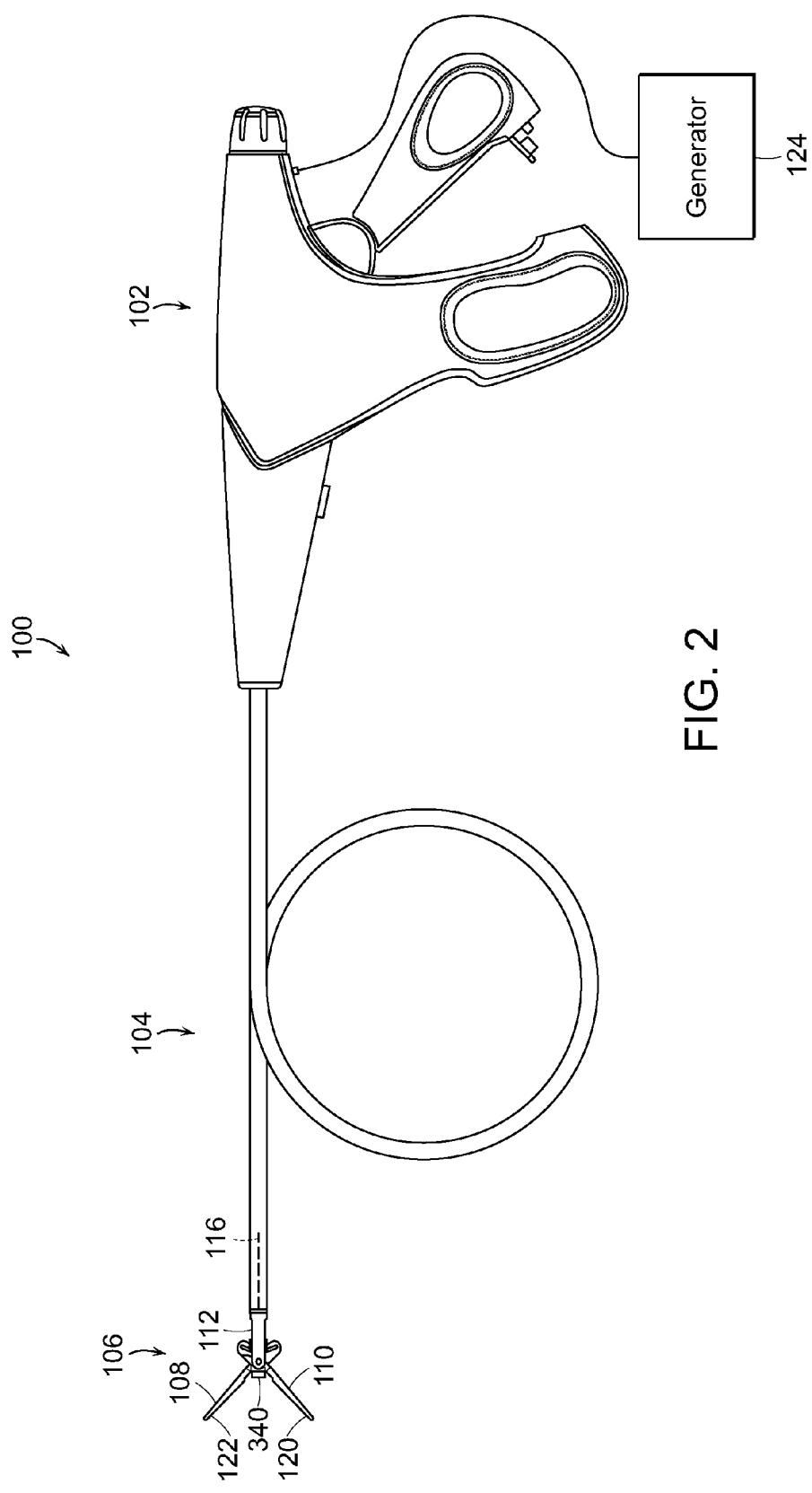
FIG. 2 illustrates one embodiment of the transection and sealing instrument of FIG. 1 for use in electrosurgical applications.

According to various embodiments, one or both of the jaw members 108, 110 may include, or serve as electrodes in monopolar or bi-polar electrosurgical applications including, for example, cutting, coagulation and welding. FIG. 2 illustrates one embodiment of the transection and sealing instrument 100 for use in electrosurgical applications. The jaw members 108, 110 of the end effector 106 may comprise respective electrodes 120, 122. The electrodes 120, 122 may be connected to an electrosurgical generator 124 via wires (not shown) extending from the end effector 106 through the shaft 104 and handle 102. The generator 124 may generate any suitable type of signal for electrosurgical applications. For example, the generator 124 may make various alternating current (A/C) and/or direct current (D/C) signals at suitable voltages, currents, frequencies and wave patterns. According to various embodiments, the transection and sealing instrument 100 may be configured for monopolar operation. In this case, the end effector 106 may comprise a single electrode, rather than two. According to various embodiments, all or a portion of the end effector 106 may serve as the single electrode.

A translating member 116 may extend within the shaft 104 from the end effector 106 to the handle 102. The translating member 116 may be made from any suitable material. For example, the translating member 116 may be, a metal wire (e.g., a tri-layered steel cable), a plastic or metal shaft, etc. In some embodiments, one or more additional translating members (not shown in FIG. 2) may be included to control the motion of the end effector 106 and/or the shaft 104. In various embodiments, the instrument 100 may comprise multiple translating members 116, for example, as described below. At the handle 102, the shaft 104 may be directly or indirectly coupled to an actuator 113 (FIG. 1). In use, a clinician may cause the actuator 113 to pivot along arrow 118 from a first position to a second position. When the actuator moves from the first position to the second position, it may translate the translating member 116 distally or proximally. Distal or proximal motion of the translating member 116 may, in turn, cause the end effector 106 to transition from an open position to a closed position (or vice versa) and/or to perform various other surgical activities such as, for example, severing and/or joining or welding. According to various embodiments, the handle 102 may comprise multiple actuators 113. When multiple actuators 113 are present, each actuator 113 may be used by a clinician to cause the end effector 106 to perform different surgical activities. In various embodiments a single actuator 113 may cause the end effector 106 to perform more than one activity. For example, a clinician may activate a single actuator 113 to force a reciprocating member 340 distally. This may, as described, both close the jaw members 108, 110 and transect any tissue between the jaw members 108, 110.

Figure 3:
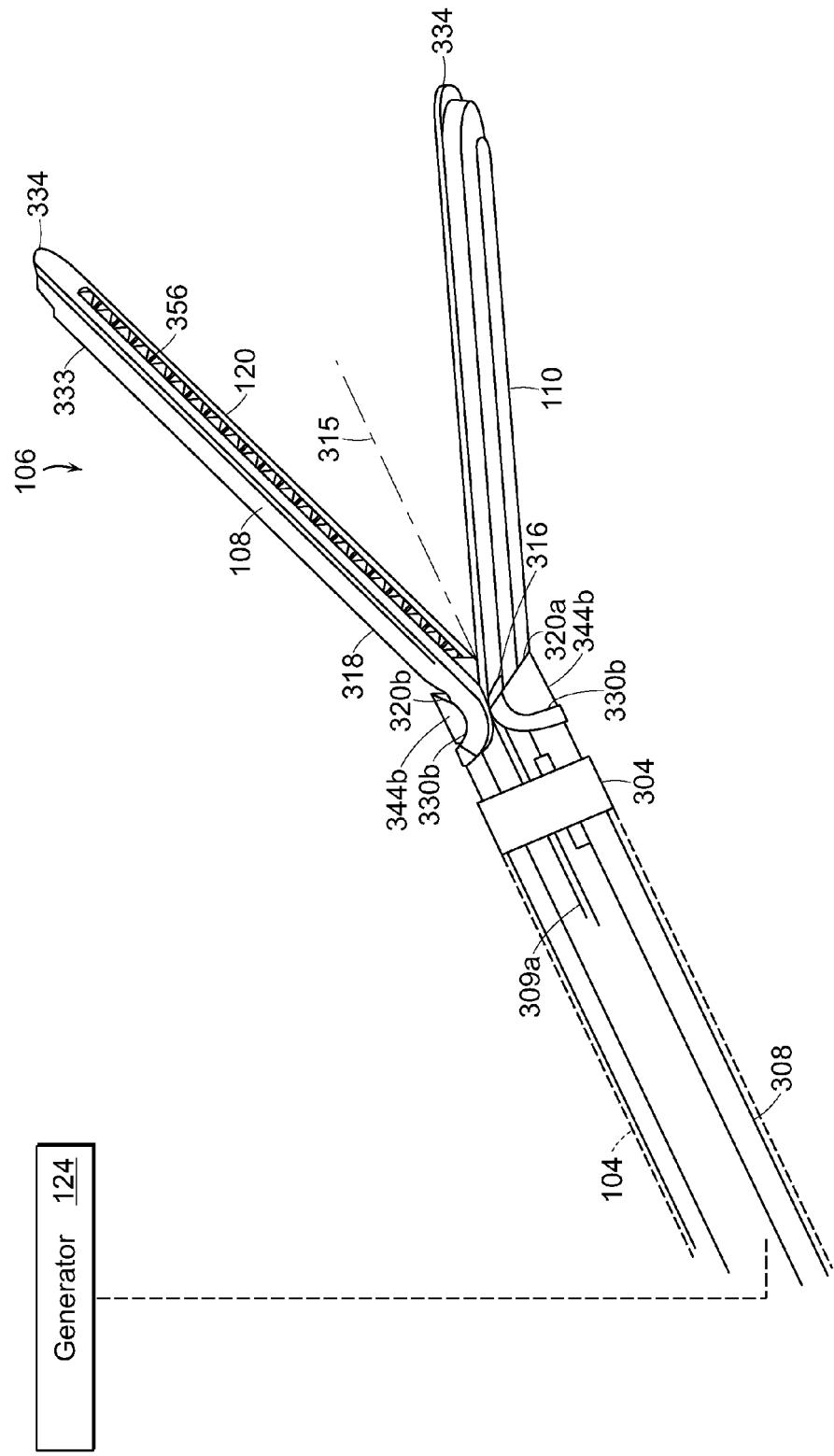
FIGS. 3 and 4 illustrate one embodiment of an end effector of a surgical grasping instrument adapted for transecting captured tissue and contemporaneous sealing of the captured tissue with RF energy delivery.
Figure 4:
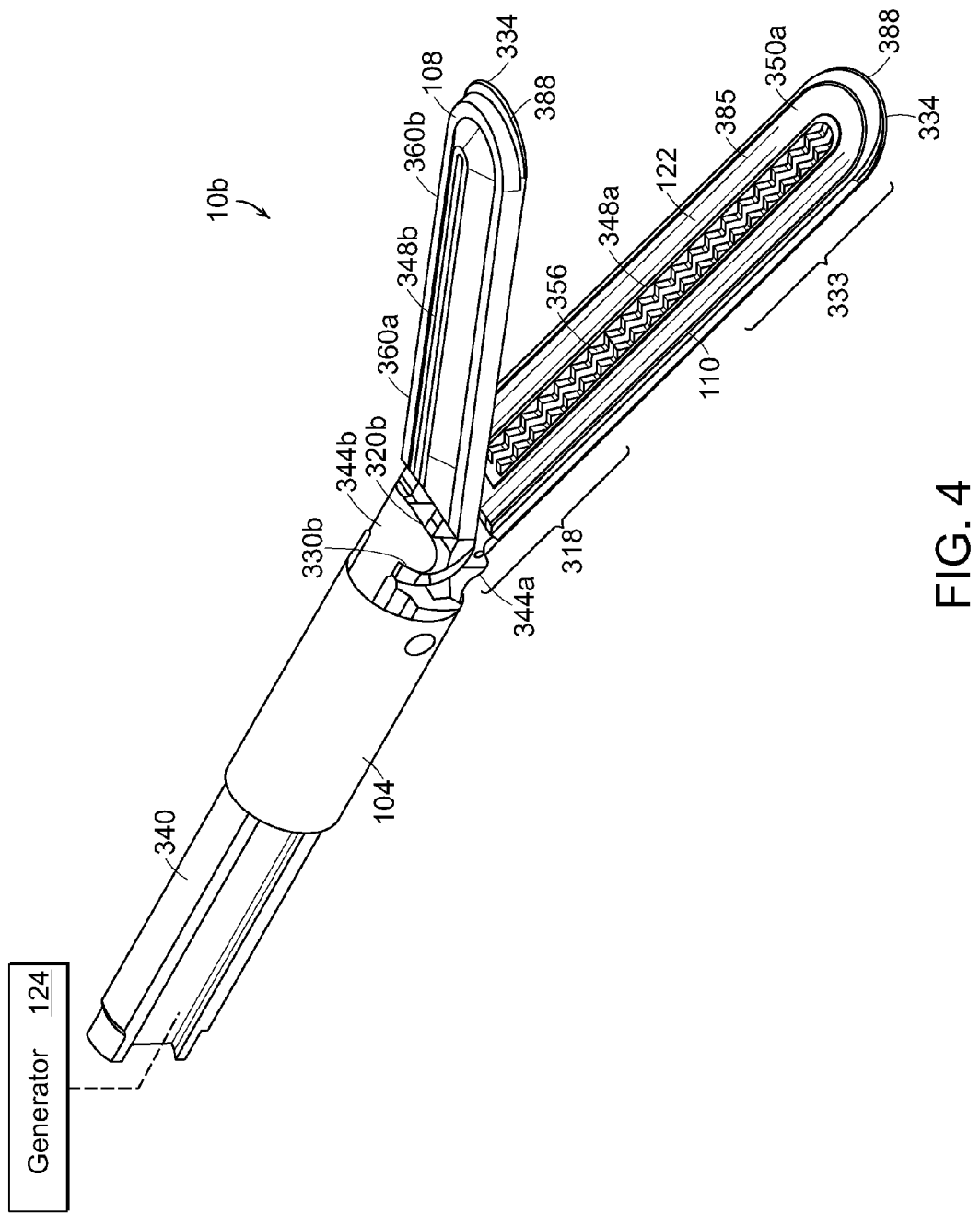

FIGS. 3 and 4 illustrate one embodiment of an end effector 106 of the instrument 100 adapted for transecting captured tissue and contemporaneous sealing of the captured tissue with RF energy delivery. The end effector 106 is carried at the distal end 304 of the shaft 104 that can be rigid, articulatable or deflectable in any suitable diameter. For example, the shaft 104 can have a diameter ranging from about 2 mm to 20 mm to cooperate with cannulae in endoscopic/laparoscopic surgeries or for use in open surgical procedures. The shaft 104 extends from a proximal handle, such as the handle 102. The handle 102 can be any type of pistol-grip or other type of handle known in the art that carries actuator levers, triggers or sliders for moving the translating member 116 or members distally and proximally to actuate the jaws as will be disclosed below. The shaft 104 has a bore 308 extending therethrough for carrying actuator mechanisms (e.g., translating member 116) for actuating the jaws and for carrying electrical leads 309a-309b for the electrosurgical components of the end effector 106.

FIGS. 3 and 4 show details of the end effector 106, including the (upper) jaw element 108 and (lower) jaw element 110 that are adapted to close or approximate along an axis 315. The jaw elements 108, 110 may both be moveable or a single jaw may rotate to provide the open and closed positions. In the example embodiment of FIGS. 1 and 2, both the lower and upper jaws 110, 108 are moveable relative to a rolling pivot location 316 defined further below.

An opening-closing mechanism of the end effector 106 operates on the basis of cam mechanisms that provide a positive engagement of camming surfaces both distal and proximal to a pivoting location (i) for moving the jaw assembly to the (second) closed position to engage tissue under very high compressive forces, and (ii) for moving the jaws toward the (first) open position to apply substantially high opening forces for "dissecting" tissue. This feature allows the surgeon to insert the tip of the closed jaws into a dissectable tissue plane—and thereafter open the jaws to apply such dissecting forces against the tissues.

Figure 5:
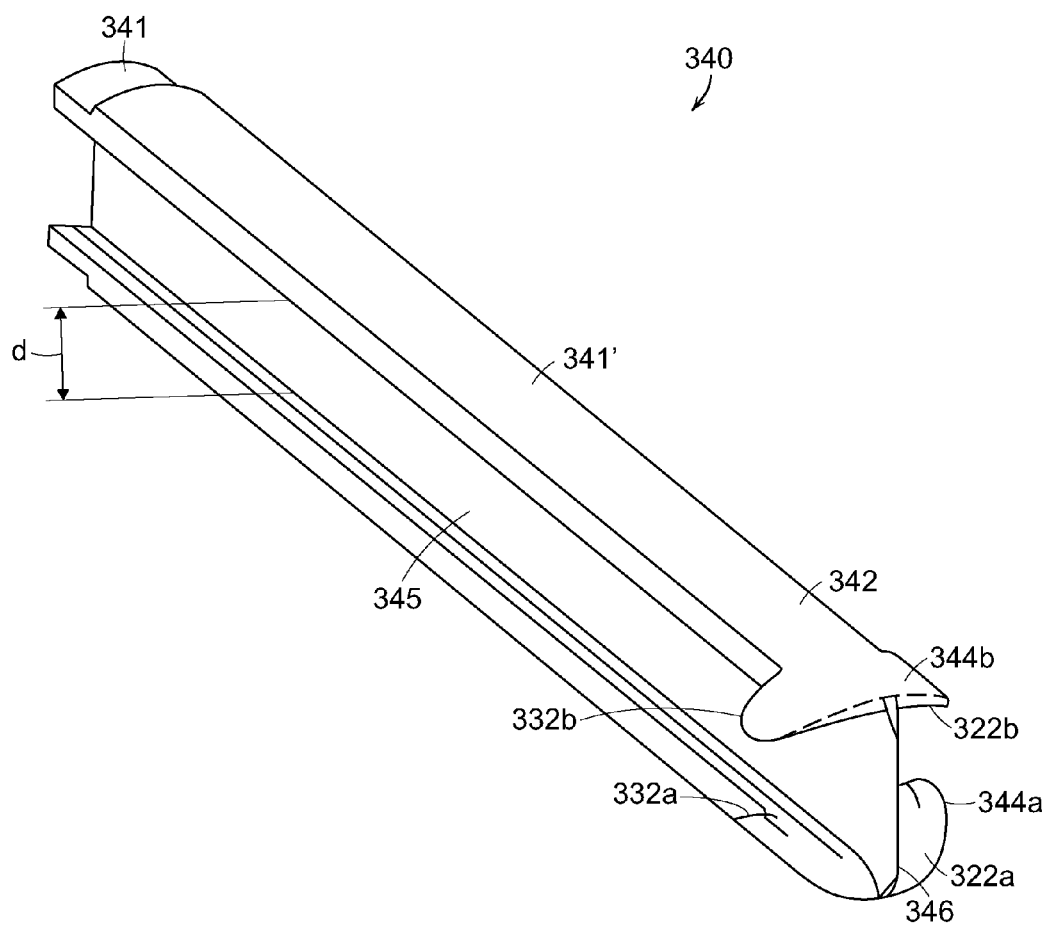
FIGS. 5 and 6 illustrate one embodiment of the reciprocating member shown in FIGS. 3 and 4.
Figure 6:
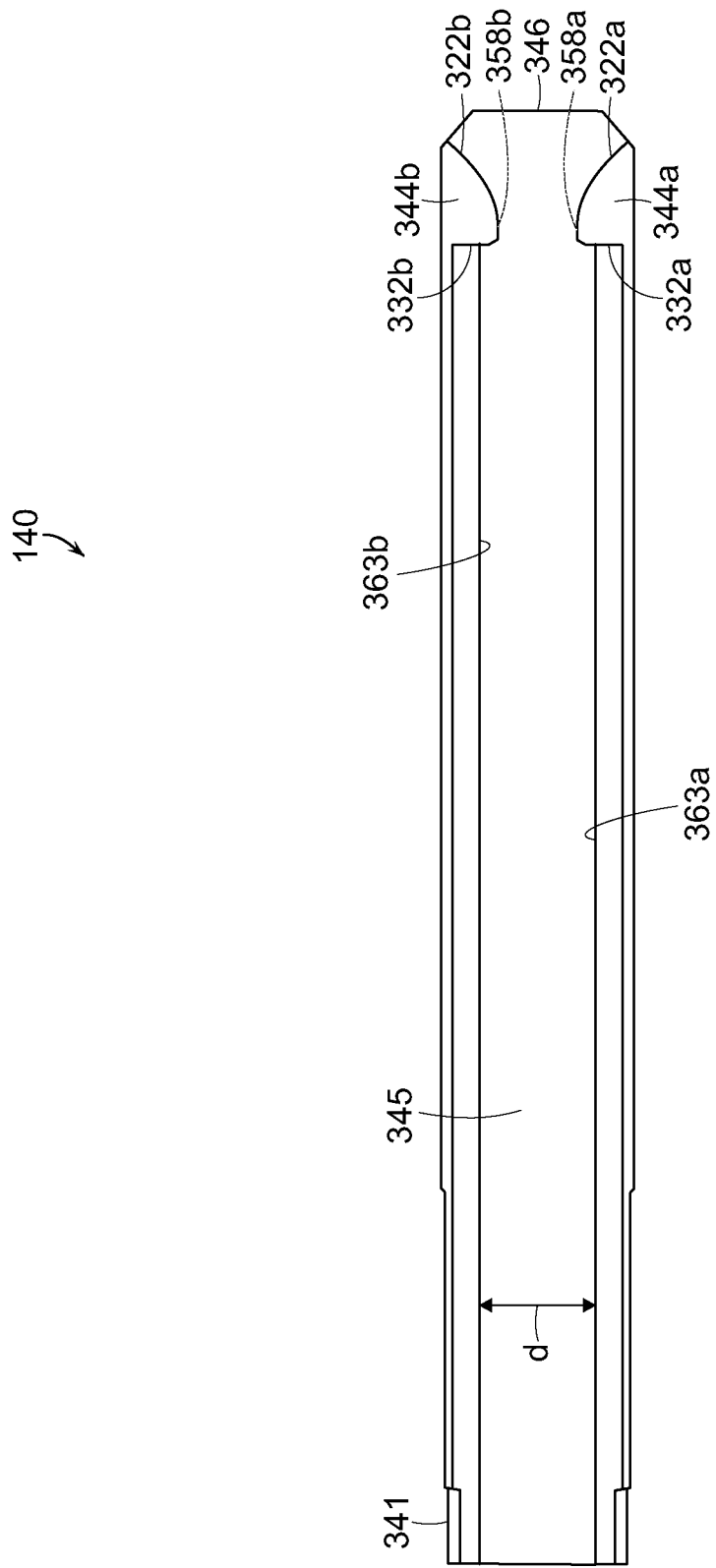

According to various embodiments, the lower and upper jaws 110, 108 may have a first end 318, in the open position, that defines first (proximally-facing) arcuate outer surface portions indicated at 320a and 320b that are engaged by a first surface portions 322a and 322b of a reciprocating I-beam member 340 (FIG. 4) that is adapted to slide over the jaw elements 108, 110 to thereby move the jaws toward closed position. FIGS. 5 and 6 show views that illustrate the cam surfaces of reciprocating member 340 de-mated from jaws 110 and 108. The first end portion 318 of the lower and upper jaws, in the open position, further defines second (distally-facing) arcuate surface portions indicated at 330a and 330b that are engaged by second surface portions 332a and 332b (FIG. 5) of the reciprocating member 340 for moving the jaw elements to the open position. The effective point of jaw rotation may lie between the first and second arcuate cam surfaces of the jaws. The distal (second) end region 333 of the paired jaws is rounded with a lip 334 that can serve as an electrode for surface coagulation as will be described below.

In this embodiment of FIGS. 3, 4 and 5, the reciprocating member 340 may be actuatable from the handle of the instrument by any suitable mechanism, such as actuator 113. For example, the actuator 113 may be coupled to a proximal end 341 of the member 340 and/or may be coupled to a translating member or members 116 that are, in turn, coupled to the reciprocating member. The proximal end 341 and medial portion 341' of member 340 are dimensioned to reciprocate within bore 308 of the shaft 104. The distal portion 342 of reciprocating member 340 carries first (lower) and second (upper) laterally-extending flanges or shoulder elements 344A and 344B that are coupled by an intermediate transverse element 345. The transverse element 345 further is adapted to transect tissue captured between the jaws with a leading edge 346 (FIG. 5) that can be a blade or a cutting electrode. The transverse element 345 is adapted to slide within channels 348a and 348b in the paired first and second jaws 110, 108. As can be seen best in FIGS. 5 and 6, the laterally-extending shoulder elements 344A and 344B define the surfaces 322a, 322b, 332a, 332b that slidably engage the arcuate cam surfaces of the jaws and that apply high compressive forces to the jaws in the closed position.

According to various embodiments, the first and second jaws 108 and 110 may define tissue-engaging surfaces or planes 350a and 350b that contact and deliver energy to engaged tissues, in part, from RF electrodes 120, 122. The engagement plane 350a of the lower jaw 110 may be adapted to deliver energy to tissue, and the tissue-contacting surface 350b of upper jaw 108 may be electrosurgically active or passive as will be described below. Alternatively, the engagement surfaces 350a, 350b of the jaws can carry any suitable electrode arrangement known in the art.

The jaws 108, 110 may have teeth or serrations 356 in any location for gripping tissue. The embodiment of FIGS. 3 and 4 depicts such serrations 356 at an inner portion of the jaws along channels 348a and 348b thus leaving engagement planes 350a and 350b laterally outward of the tissue-gripping elements. The serrations 356 may be of any suitable symmetric or asymmetric shape or combination of shapes including, for example, triangular, rounded, sinusoidal, etc. In the embodiments described below, the engagement planes 350a and 350b and electrode(s) 120, 122 generally are shown with a non-serrated surface for clarity of explanation, but such engagement planes and electrodes themselves can be any non-smooth gripping surface. The axial length of jaws 108, 110 indicated at L can be any suitable length depending on the anatomic structure targeted for transection and sealing. In various embodiments, the length L may be between 10 mm and 50 mm. In some embodiments, the length L may be longer. For example, one embodiment of an end effector 106 for resecting and sealing organs such as a lung or liver may have a length L of about 200 mm. Also, for example, for some surgical tasks, the jaws having a shorter length L may be used, including, for example, jaws having a length L of about 5.0 mm.

Figure 9:
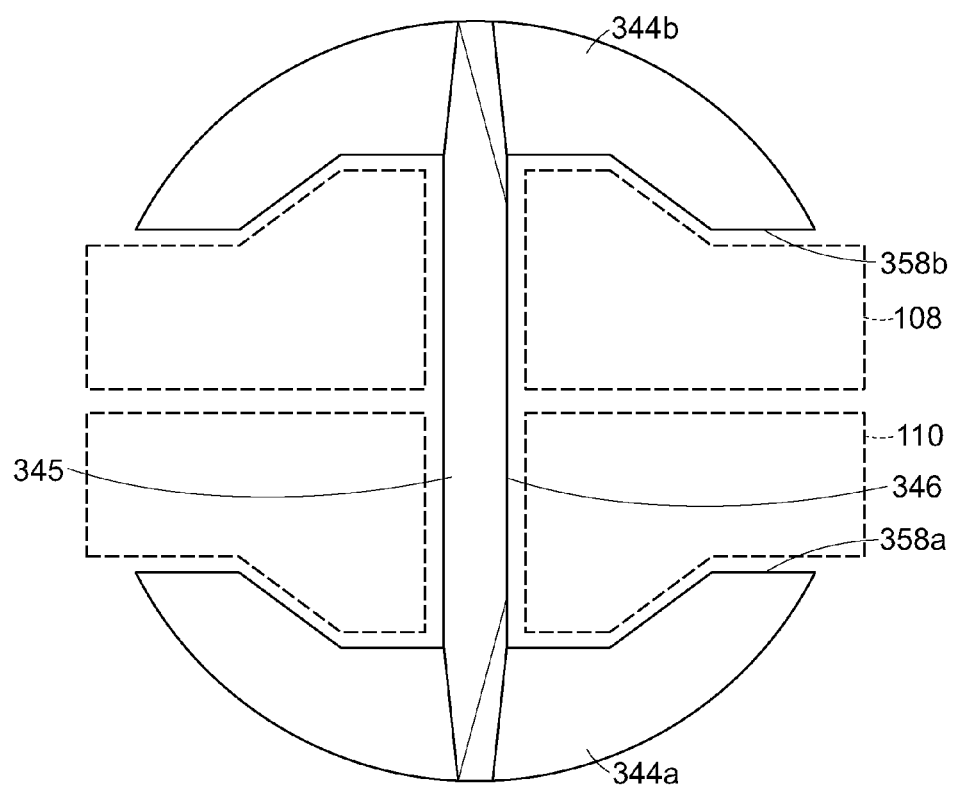
FIG. 9 illustrates an end view of one embodiment of the reciprocating member of FIG. 3 with the jaws of the end effector in phantom view.
Figure 10:
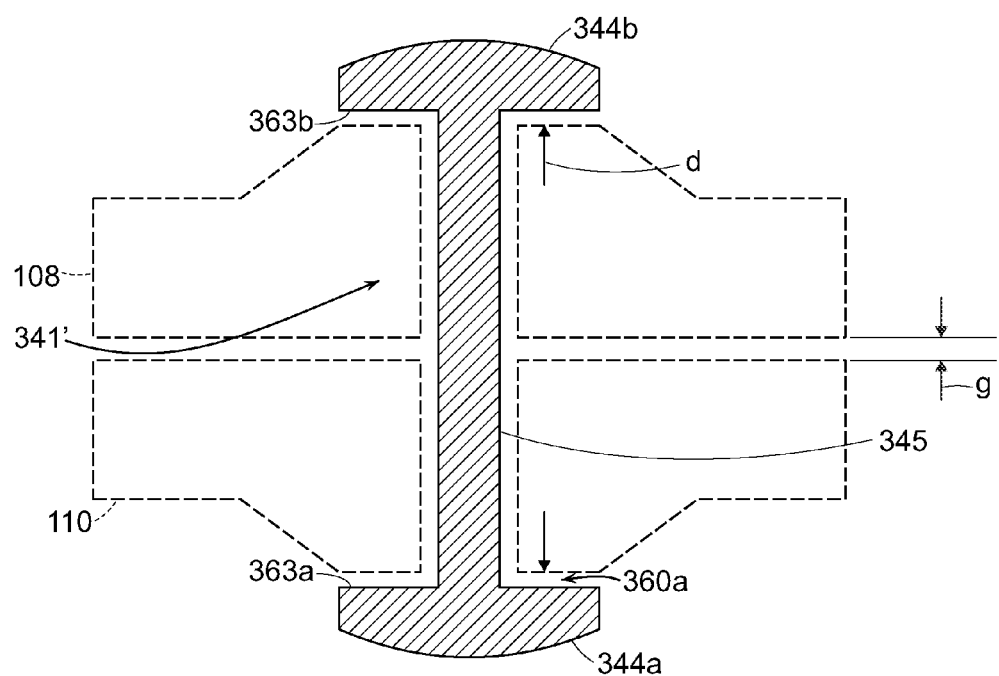
FIG. 10 illustrates a cross-sectional view of the embodiment shown in FIG. 9 along a cross-section taken at a position proximally located from the end view shown in FIG. 9.

FIG. 9 illustrates an end view of one embodiment of the reciprocating member 340 with the jaws 110 and 108 in phantom view. The view shown in FIG. 9 is a head-on view with the distally positioned blade surface 346 pointed out of the page. FIG. 10 illustrates a cross-sectional view of the embodiment shown in FIG. 9 along a cross-section taken at a position proximally located from the end view shown in FIG. 9. The transverse element 345 of the reciprocating member 340 may define a transverse dimension d between innermost surfaces 358a and 358b of the flanges 344A, 344B of the reciprocating member 340 and cooperating medial and distal outer surfaces 360A and 360B of the jaws. The selected transverse dimension d between the flanges or shoulders 344A and 344B thus further defines the engagement gap g between the engagement planes 350a and 350b of the jaws in the closed position. It has been found that very high compression of tissue combined with controlled RF energy delivery is optimal for welding the engaged tissue volume contemporaneous with transection of the tissue. According to various embodiments, the engagement gap g between the engagement planes 350a, 350b may range from about 0.001" to about 0.050". For example, the gap g between the engagement planes ranges from about 0.001" to about 0.010". As can be seen in FIGS. 5 and 10, the medial portion 341' of the reciprocating member 340 may have an "I"-beam shape with inner surface portions 363a and 363b that engage the cooperating medial outer surfaces of the jaws. Thus, in various embodiments, the entire length L of the jaws can be maintained in a fixed spaced-apart relationship to define a consistent engagement gap g. According to various embodiments, the engagement gap g may be selected to be large enough to prevent tissue engaged between the jaws 108, 110 from being sheared and to prevent electrical shorts between the electrodes 120, 122.

Figure 7:
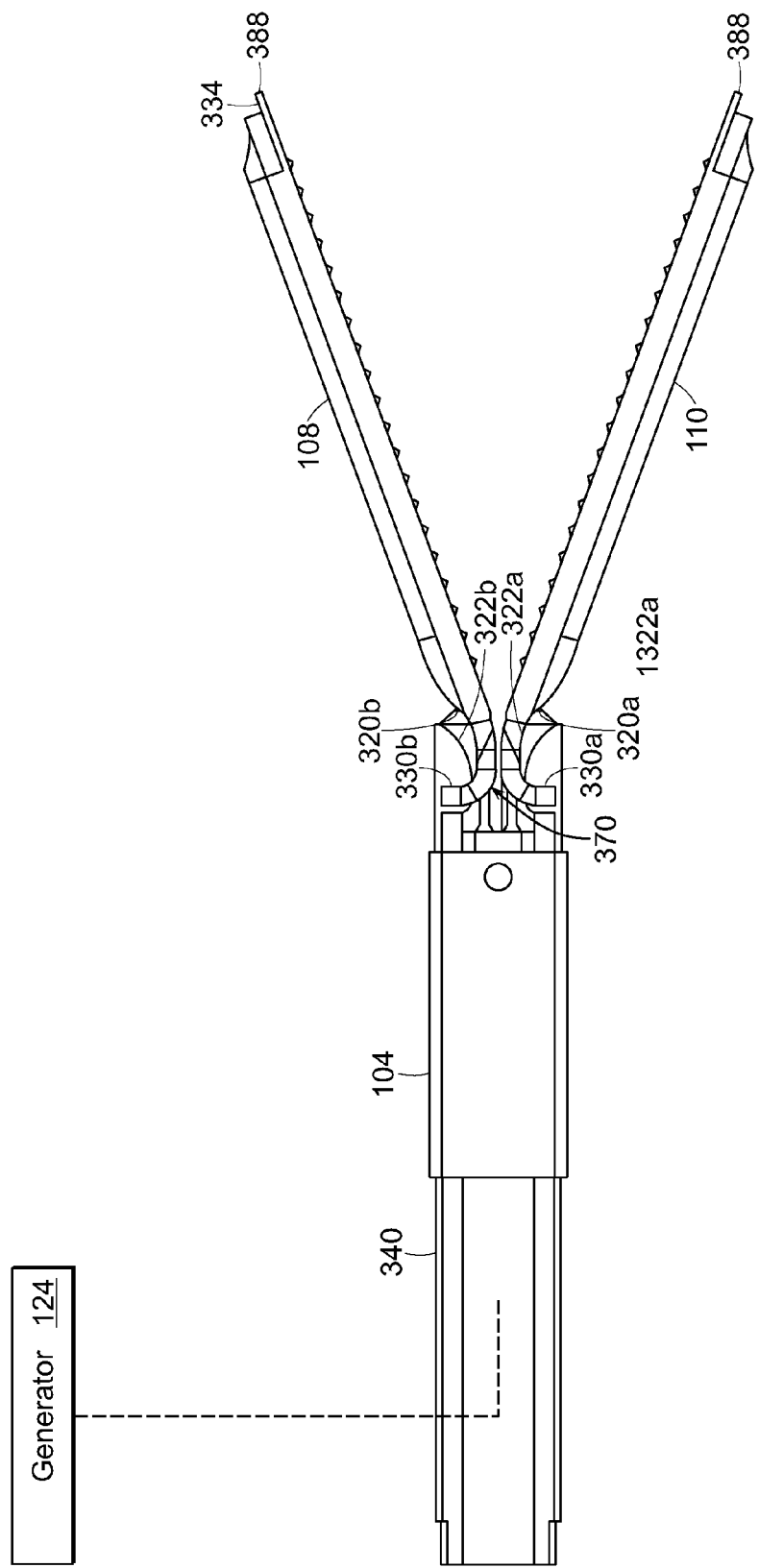
FIGS. 7 and 8 illustrate one embodiment of the actuation of a reciprocating member shown in FIG. 3 from a first retracted position to a second extended position to move the jaws of the end effector from an open position to a closed position.
Figure 8:
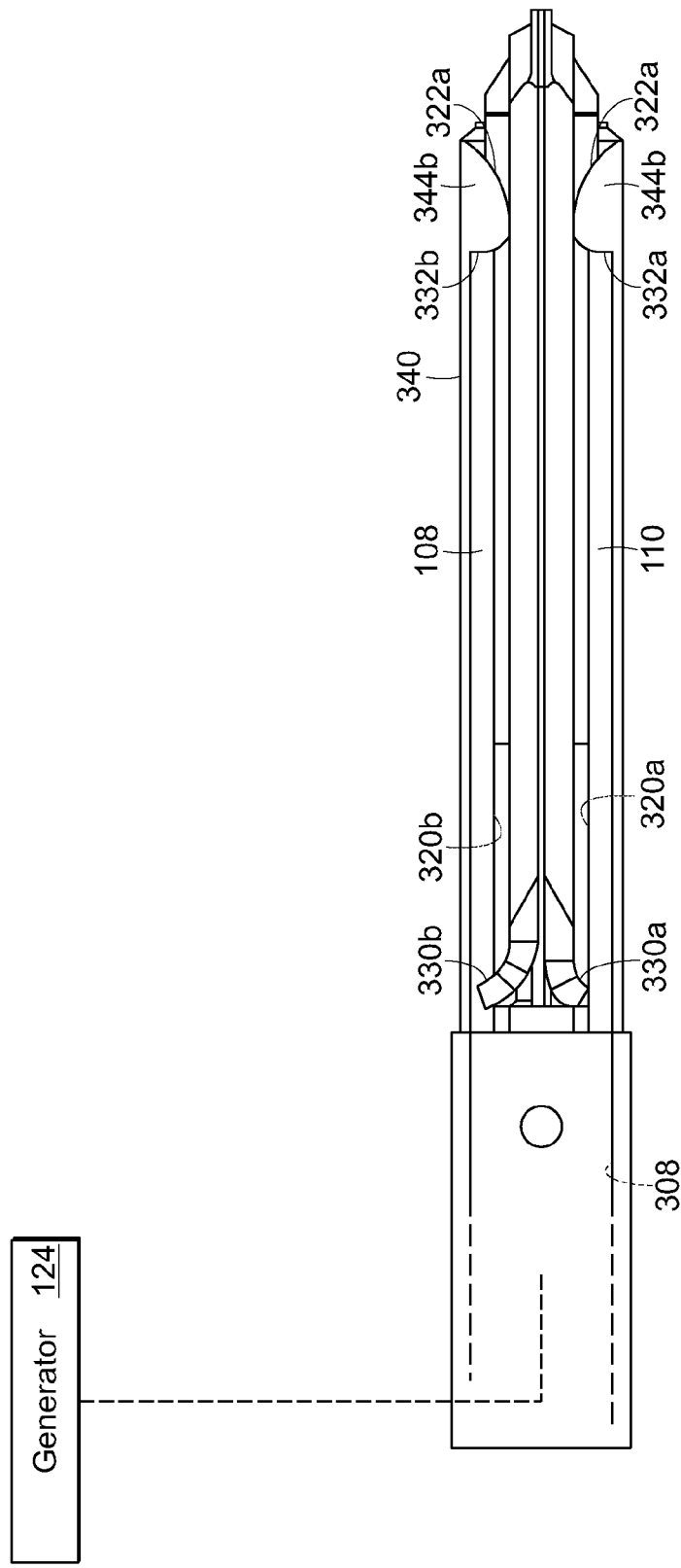

FIGS. 7 and 8 illustrate one embodiment of the actuation of the reciprocating member 340 from a first retracted position to a second extended position to move the jaws 110 and 108 from an open position to a closed position. Referring to FIG. 7, it can be seen that the translatable member 340 is being moved in the proximal direction so that the proximal-facing surfaces 332a and 332b (FIG. 5) of reciprocating member 340 about the outer surfaces 330a and 330b of the jaws thus forcing the jaws apart, for example to apply dissecting forces to tissues or to open jaws 108 and 110 to engage targeted tissues for hemostasis and transection. FIG. 8 shows the reciprocating member 340 after having been fully extended in the distal direction so that the distal-facing surfaces 322a and 322b of reciprocating member 340 have ridden up and over the proximal arcuate surfaces 320a and 320b of the jaws (and medial outer surfaces 360A and 360B) thus forcing the jaws together thereby producing a compressive force between jaws 108 and 110. According to various embodiments, the orientation of surfaces 322a, 322b of the reciprocating member 340 and/or the arcuate surfaces 320a, 320b may be modified to modify the compression rate provided by the reciprocating member 340. For example, the orientation of the 322a, 322b of the reciprocating member 340 and/or the arcuate surfaces

320a, 320b may vary from one embodiment to another, or may vary within a single embodiment in order to cause variable compression rates within a single stroke of the reciprocating member 340.

Figure 11:
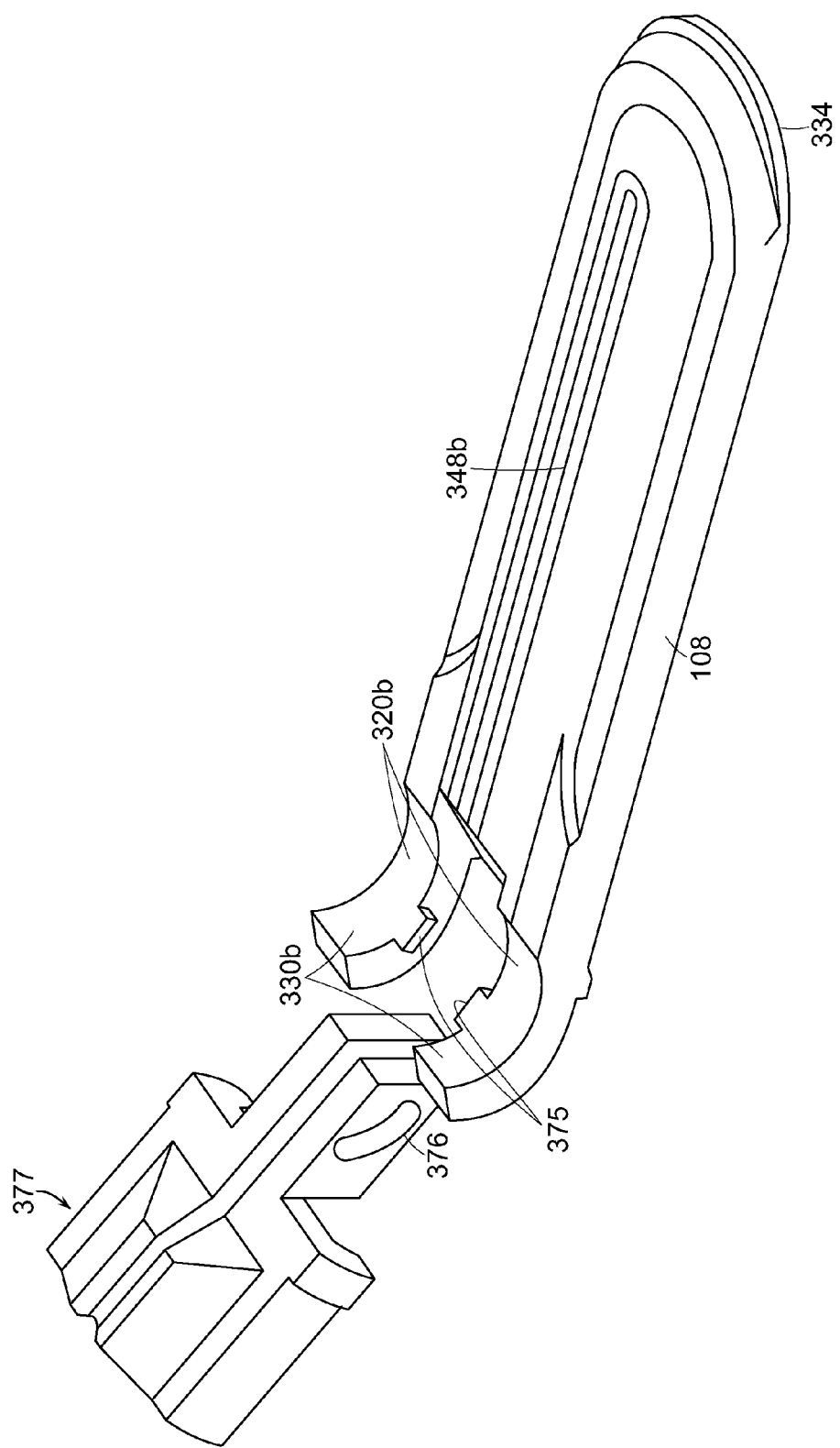
FIG. 11 illustrates one embodiment of the jaw of the end effector of FIG. 3 de-mated from the end effector.

According to various embodiments, the jaws 108, 110 may rollably contact one another along the interface 370 between inner surfaces 372 of the first end 318 of the jaws. As jaws 108 and 110 articulate, the pivot point is moving as the point of contact changes at the interface between surfaces 370 and 372. Thus, the jaw assembly may not need to define a true single pivot point as is typical of hinge-type jaws known in the art. The pivotable action of the jaws along interface 370 may be described as a rolling pivot that optionally can allow for a degree of dynamic adjustment of the engagement gap g at the proximal end of the jaws. FIG. 11 illustrates one embodiment of the jaw 108 de-mated from the end effector 106. Referencing FIG. 11, the jaws elements 110, 108 can be retained relative to one another and the shaft 104 by means of protruding elements 375 that couples with arcuate slots 376 in an internal member 377 that is fixedly carried in bore 308 of shaft 104. Alternatively, outwardly protruding elements can cooperate with slots in the wall of shaft 104. Also, for example, the jaw assembly may (optionally) comprise springs for urging the jaws toward the open position, or closed position depending on the desired at-rest state of the device.

Figure 12:
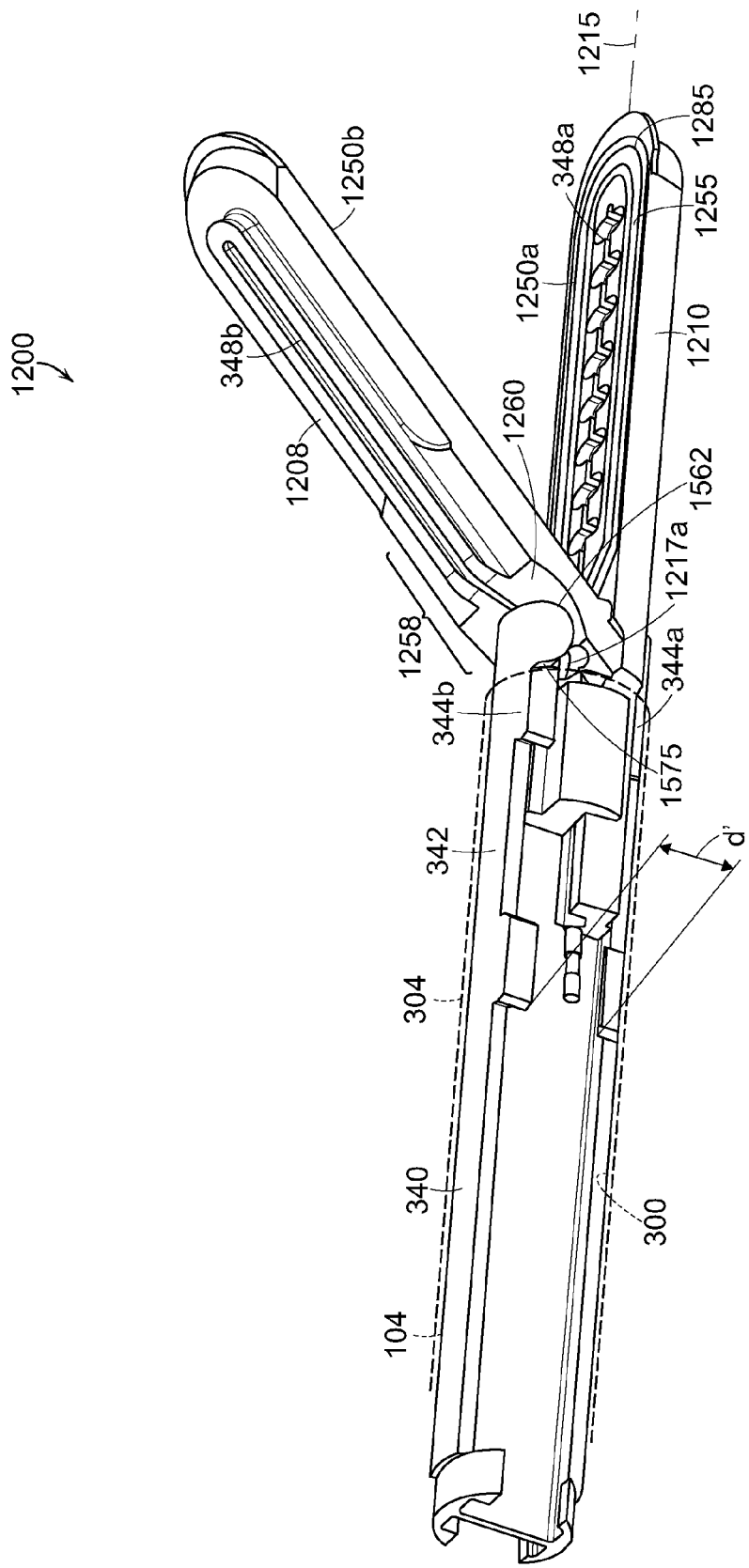
FIGS. 12-14 illustrate one embodiment of an end effector having a single rotating jaw member.
Figure 13:
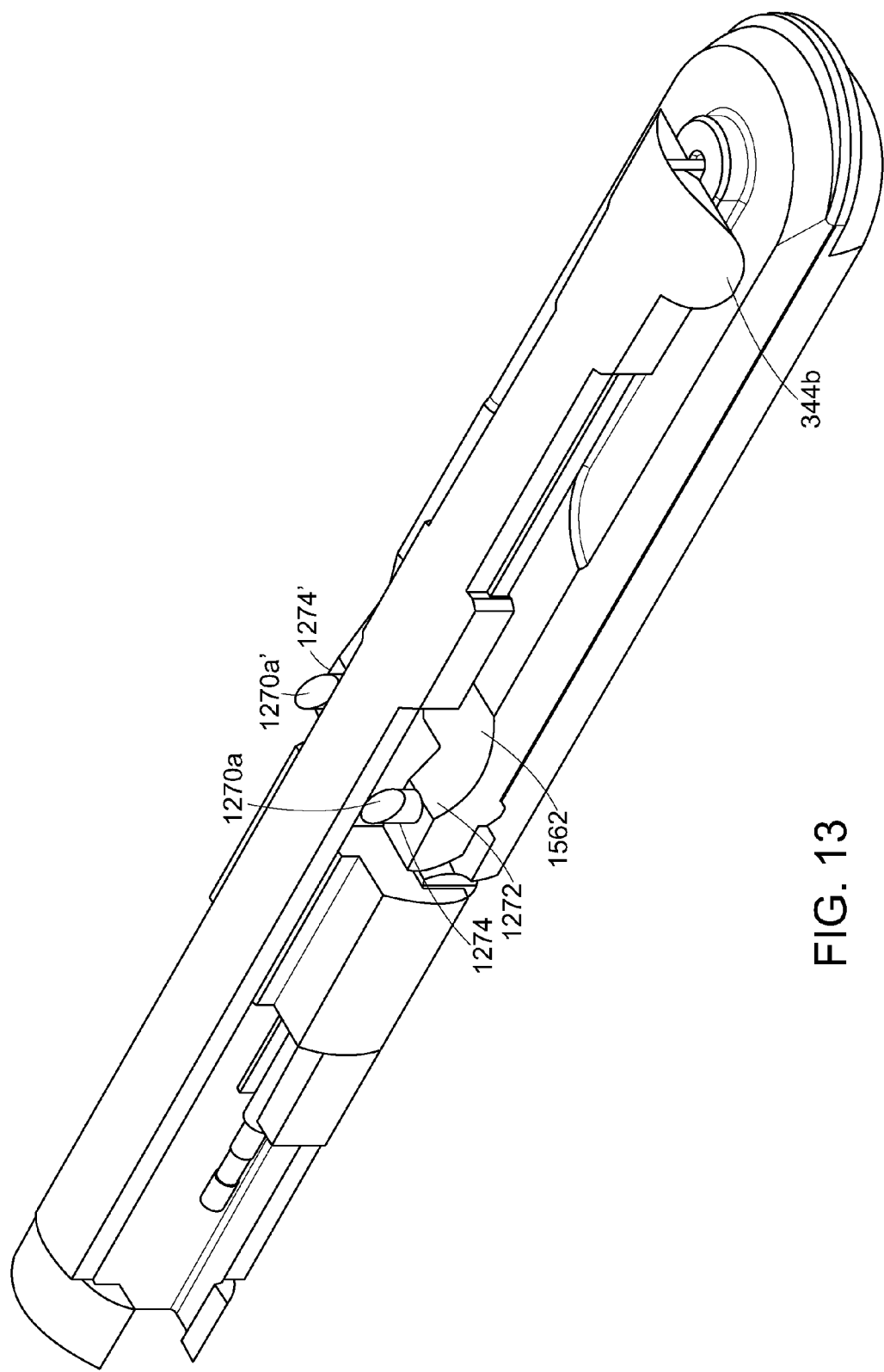

FIGS. 12-13 illustrate one embodiment of an end effector 1200 having a single rotating jaw member. Like the end effector 106 described above, the end effector 1200 is carried at the distal end 304 of the shaft 104 that has a bore 308 extending therethrough. According to various embodiments, the first (lower) jaw 1210 may be a fixed extension portion of the shaft 104. As can be seen in FIGS. 12 and 13, the second (upper) jaw 1208 is adapted to close or approximate along longitudinal axis 1215.

The opening-closing mechanism of end effector 1200 may provide cam surfaces for positive engagement between reciprocating member 340 and the jaws (i) for moving the jaws to a closed position to engage tissue under high compressive forces, and (ii) for moving the jaws toward the (first) open position thereby providing high opening forces to dissect tissue with outer surfaces of the jaw tips. The reciprocating member 340 operates as described previously to reciprocate within bore 308 of the shaft 104. As can be seen in FIG. 13, the distal end portion 342 of reciprocating member 340 carries distal first and second laterally-extending flange portions 344A and 344B with the blade-carrying transverse element 345 extending therebetween. The blade-carrying member slides within channels 348a and 348b in the jaws.

In the example embodiment of FIGS. 12 and 13, the first and second jaw members 1210 and 1208 again define engagement surfaces or planes 1250a and 1250b that deliver energy to engaged tissue. The engagement planes may carry one or more conductor/electrodes 1255 and, in various embodiments, may comprise a PTC matrix 1285 in at least one of the jaws' engagement surfaces 1250a and 1250b. In the embodiment of FIGS. 12 and 13, the upper jaw 1208 has a proximate end region 1258 that, in the open position, defines a first (proximally-facing) arcuate cam surface indicated at 1260 that is engaged by a first surface portion 1562 of the reciprocating member 340. The first (proximal) end region 1258 of the upper jaw, in the open position, further defines second (distally-facing) surface portions indicated at 1270a and 1270a' that are engaged by second surface 1272 of reciprocating member 340 for moving the jaw assembly to an open position.

Figure 14:
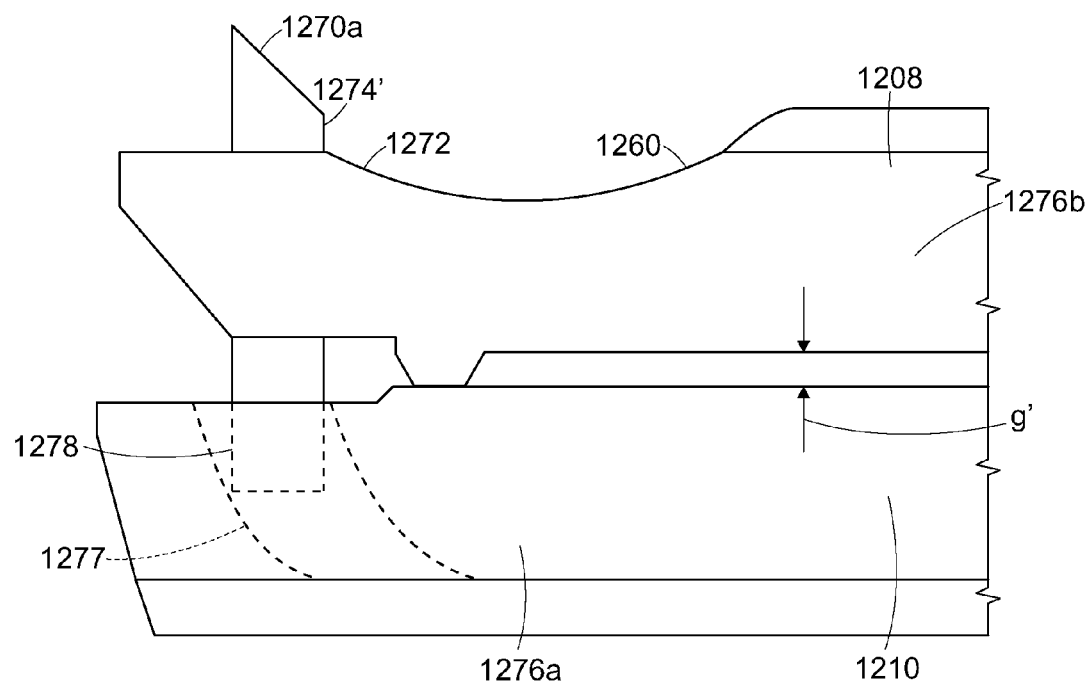

As can be seen best in FIG. 13, the cam surfaces 1270a and 1270a' may be formed into pins or projecting elements 1274 and 1274' that may serve multiple purposes. Referring to FIG. 14, the pins 1274 and 1274' extend through the upper jaw body 1276b and are received within arcuate bores 1277 in body 1276a of lower jaw 1210. The lower portions 1278 (collectively) of the pins 1274 and 1274' thus can retain upper jaw 1208 and prevent it from moving axially or laterally relative to the jaw axis 1215 while still allowing the jaw's rotation for opening and closing. The pin mechanism further allows for greatly simplified assembly of the instrument.

Figure 19:
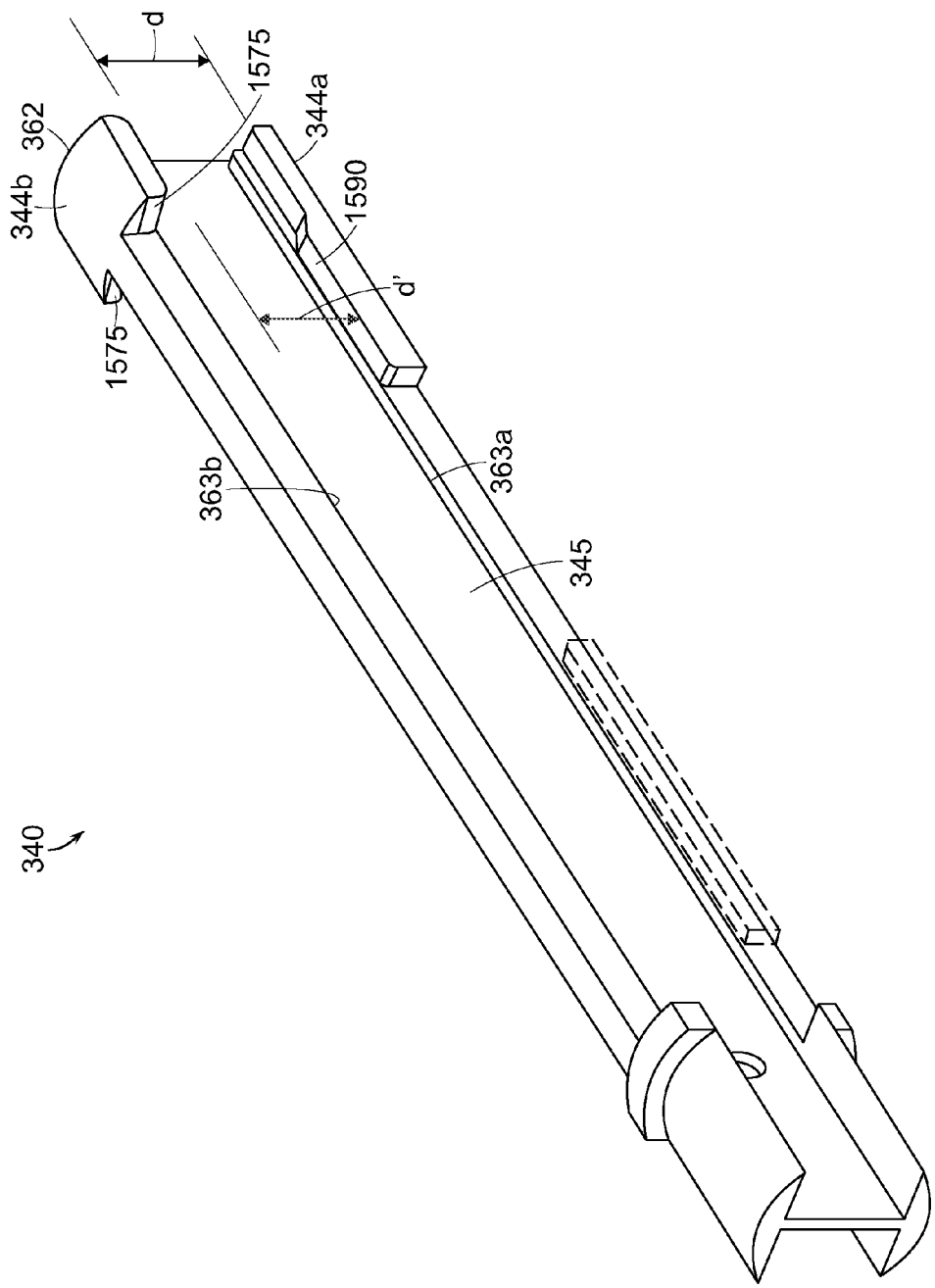
FIG. 19 illustrates one embodiment of the reciprocating member configured with separate elevated step or cam surfaces in the lower flange portions that are adapted to slidably engage the ends of the rectangular pins on either side of upper jaw.

The pins 1274 and 1274' may provide additional functionality by providing a degree of "vertical" freedom of movement within the first (proximal) end portion 1258 of the jaw. As can be seen in FIGS. 12 and 19, the distal laterally-extending flange portions 344A and 344B define a transverse dimension d (cf. FIG. 19) that in turn determines the dimension of the engagement gap g of the distal end of the jaws in the jaw-closed position (FIG. 14). The transverse dimension d equals the dimension between inner surfaces of flange portions 344A and 344B that slidably contact the outer surfaces of both jaws.

Figure 16:
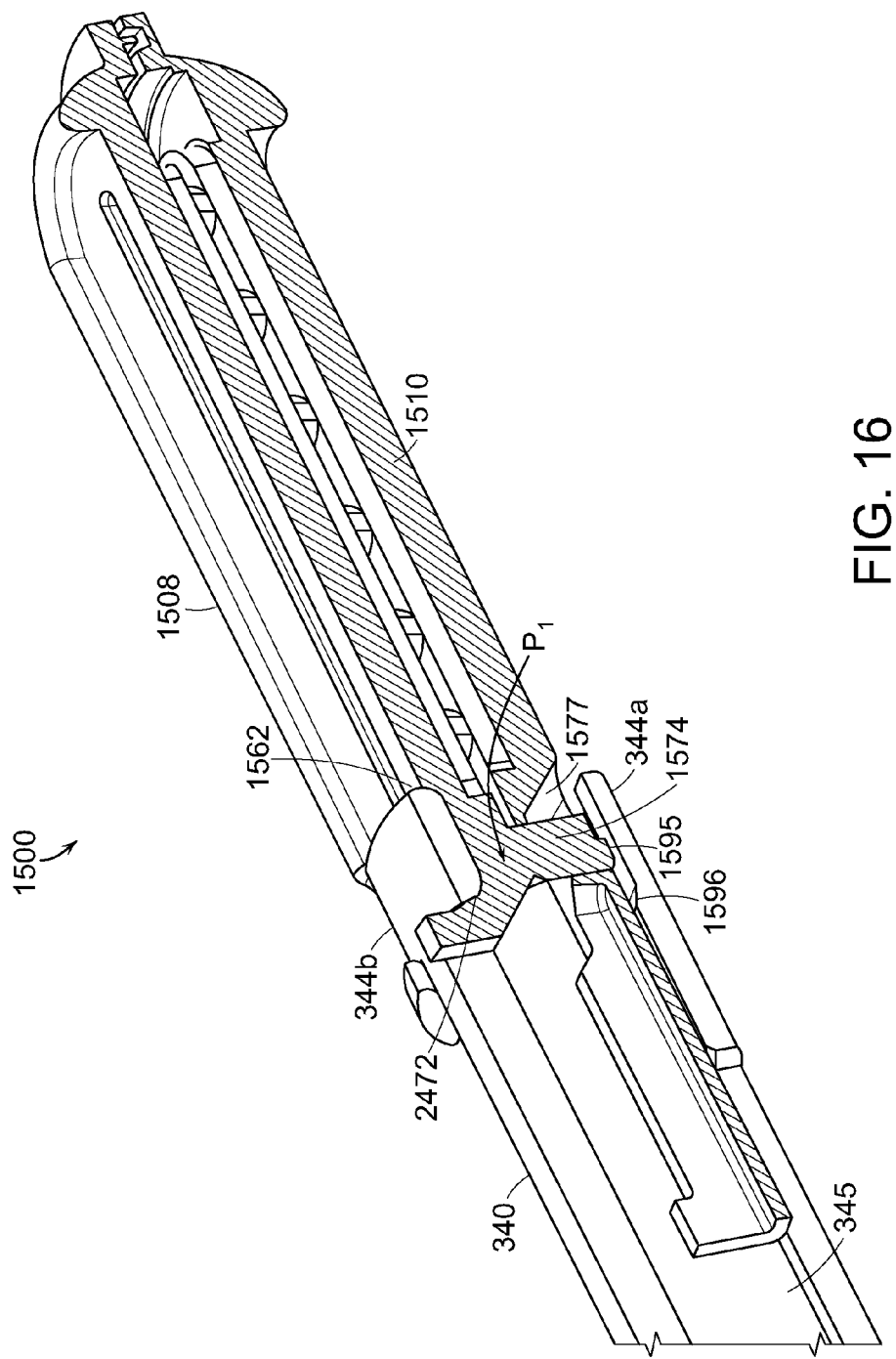
Figure 17:
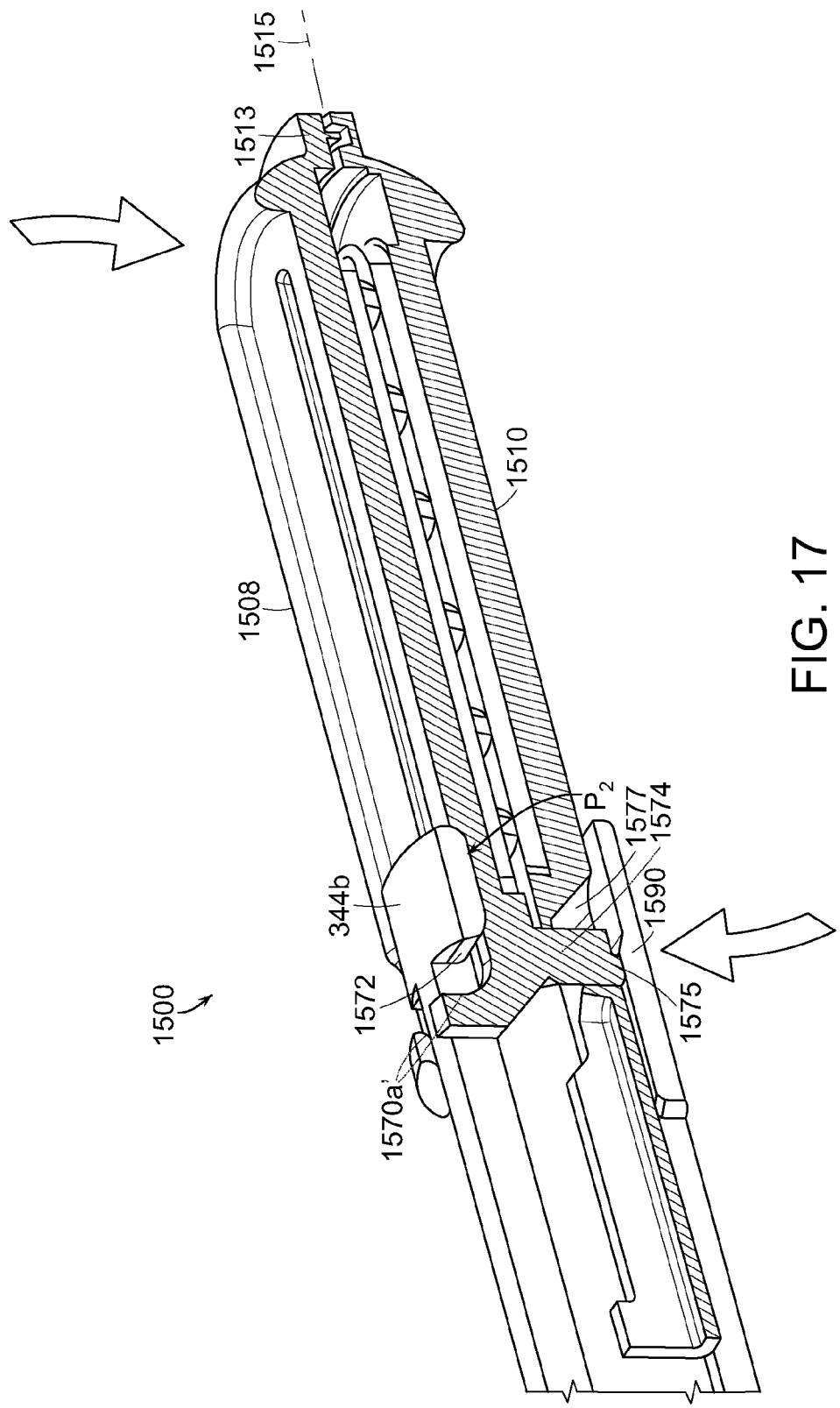
Figure 18:
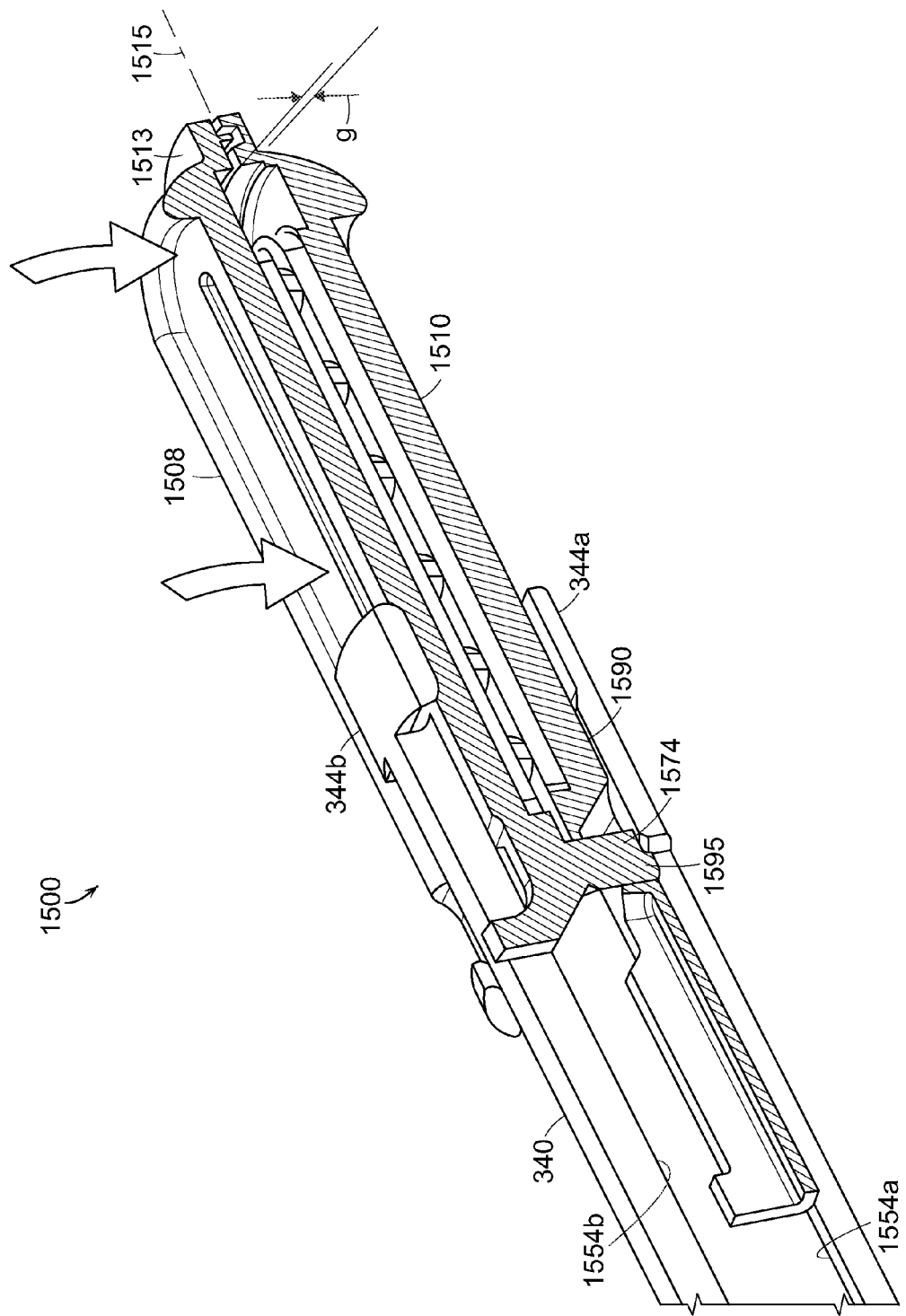

FIGS. 15-18 illustrate another embodiment of an end effector 1500 that provides both electrosurgical functionality and improved grasping and dissecting functionality for endoscopic surgeries. In FIGS. 15-18, both the upper and lower jaws are shown in cut-away views to show internal cam surfaces of the upper jaw 1510 and the reciprocating member 340. The jaw assembly 1500 may carry engagement surfaces for applying electrosurgical energy to tissue as in the previously described embodiments, as well as cutting means for transecting the engaged tissue volume. The jaw assembly 1500 relates to the ability of the jaw structure, in one mode of operation, to be used for general grasping and dissecting purposes wherein the distalmost tips 1513 of the jaws can close tightly on tissue with little movement of the actuator lever 113 in the handle of the instrument. At the same time, in another mode of operation, the jaw assembly 1500 can close to apply very high compressive forces on the tissue to enable welding. Thus, the jaw structure may provide (i) a first non-parallel jaw-closed position for grasping tissue with the distal jaws tips (FIG. 17), and (ii) a second parallel jaw-closed position for high compression of tissue for the application of electrosurgical energy (FIG. 18).

Figure 15:
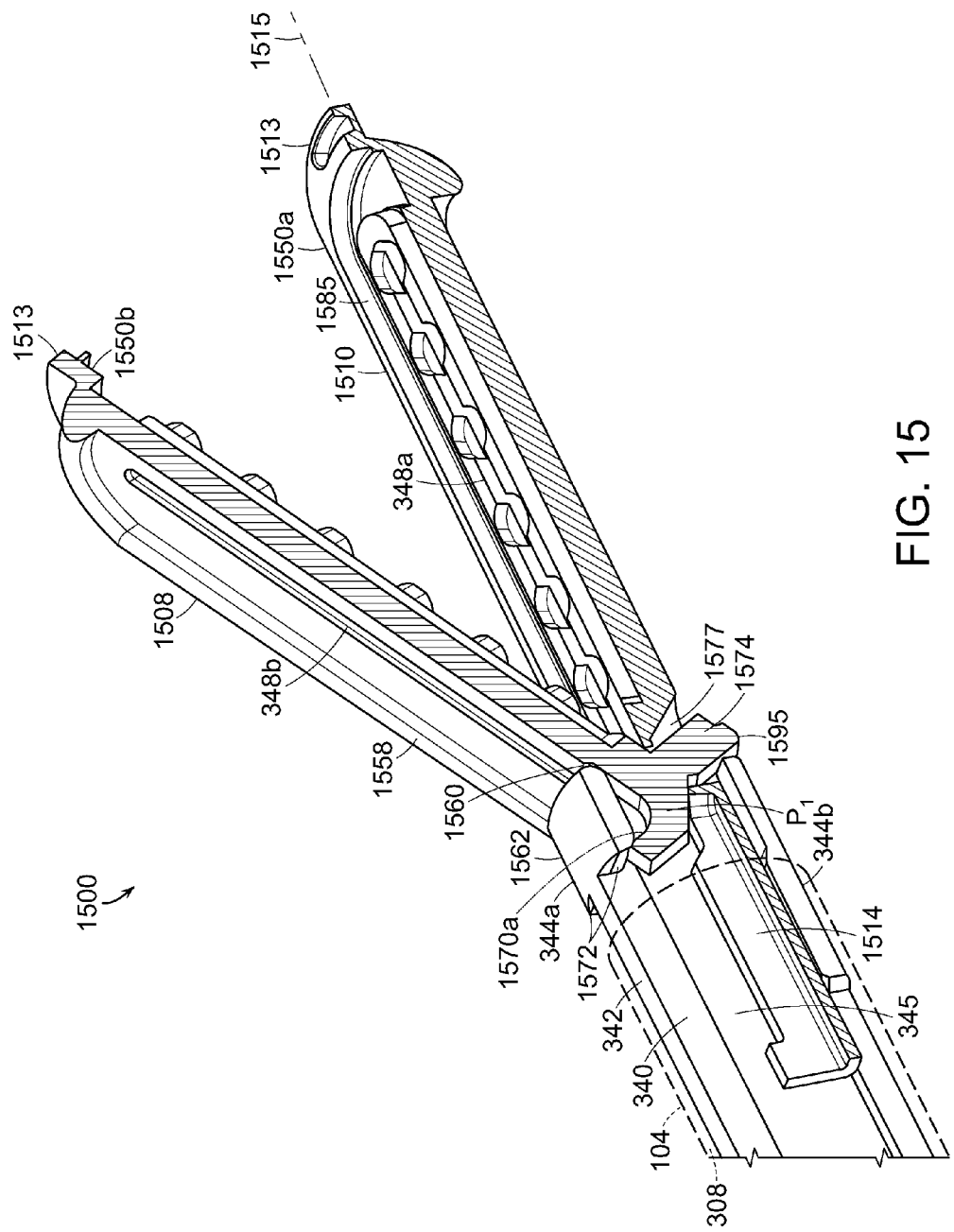
FIGS. 15-18 illustrate another embodiment of an end effector having a single rotating jaw member.

Referring to FIG. 15, the end effector 1500 again has a shaft 104 that is similar to the shaft 104 as used by the end effector 1200 with first (lower) jaw 1510 comprising a fixed extending portion 1514 of the shaft 104. As can be seen in FIG. 15, the second (upper) jaw 1508 is adapted to close or approximate about longitudinal axis 1515. The opening-closing mechanism of jaw assembly 1500 provides cam elements and cooperating jaw surfaces for positive engagement between the reciprocating member 340 as described previously (i) for moving the jaws to a closed position to engage tissue, and (ii) for moving the jaws toward the open position thereby providing high opening forces to dissect tissue with outer surfaces of the jaw tips 313.

The reciprocating member 340 (FIG. 19) operates as described previously to reciprocate within bore 308 of the shaft 104 (FIG. 15). As can be seen in FIG. 15, the distal end 342 of the reciprocating member 340 again carries distal flange portions 344A and 344B with a blade-carrying transverse portion 345 therebetween. The transverse portion 345 slides within channels 348a and 348b in the paired jaws. In the example embodiment of FIG. 15, the first and second jaws 1510 and 1508 again define engagement surfaces 1550a and 1550b that can deliver electrosurgical energy to engaged tissue.

In the embodiment of FIG. 15, the upper jaw 1508 has a proximal end 1558 that defines a first (proximally-facing) arcuate jaw surface 1560 that is engaged by a first cam surface element 1562 of reciprocating member 340 for opening the jaw. The proximal end 1558 of the upper jaw further defines second (distally-facing) jaw surface portions indicated at 1570a and 1570a' that are engaged by second cam element 1572 of reciprocating member 340 for moving the jaw assembly to an open position.

The embodiment of FIG. 15 shows that the upper jaw 1508 has a floating primary pivot location indicated at $P_1$ that is provided by the projecting elements or rectangular pins 1574 (collectively) on either side of the channel portions 348a that slidably extend into bores 1577 (collectively) in the lower jaw body (cf. FIG. 14). The lower portions of the pins 1574 thus allow upper jaw 1508 to rotate while at the same time the pin-and-bore mechanism allows the upper jaw to move upwardly away from the lower jaw.

For example, the degree of "vertical" freedom of movement of the upper jaw allows for the system to "tilt" the distal tip 1513 of upper jaw 1508 toward the axis 1515 to thereby allow the distal jaw tips 1513 to grasp tissue. This is termed a non-parallel closed position herein. The tilting of the jaw is accomplished by providing a plurality of cam surfaces in the upper jaw 1508 and the reciprocating member 340.

As can be seen in FIGS. 15 and 19, the lower and upper laterally-extending flange portions 344A and 344B of the reciprocating member 340 define a transverse dimension d that determines the dimension of gap g between the engagement surface of the jaws in the fully jaw-closed position (FIG. 18). The transverse dimension d equals the dimension between inner surfaces of flange portions 344A and 344B that slidably contact the outer surfaces of both jaws.

FIG. 19 illustrates one embodiment of the reciprocating member 340 configured with separate elevated step or cam surfaces 1590 in the lower flange portions 344A that are adapted to slidably engage the ends 1595 of the rectangular pins 1574 on either side of upper jaw 1508. The elevated cam surfaces 1590 of reciprocating member 340 thus create another transverse dimension d' between inner surfaces of the flange portions 344A and 344B that move the jaws toward either the first jaw-closed position or the second jaw-closed position.

Now turning to FIGS. 15-18, the sequence of cut-away views illustrate how the multiple cam surfaces cause the jaws to move between a first "tilted" jaw-closed position to a second "high-compression" jaw-closed position. In FIG. 15, the jaws are in an open position. In FIG. 16, the reciprocating member 340 is moved distally and its cam surface element 1562 pushes on jaw surfaces 1560 to move the jaws toward a closed position wherein the jaws rotate about primary pivot location $P_1$. In FIG. 16, it can be seen that the elevated cam surfaces 1590 in the lower flange 344A have not yet engaged the ends 1595 of the rectangular pins 1574.

Now turning to FIG. 17, the reciprocating member 340 is moved further distally wherein the elevated cam surfaces 1590 of lower flange 344A have now engaged and elevated the ends 1595 of rectangular pins 1574 thereby tilting the upper jaw. The upper jaw 1508 is tilted slightly by forces in the direction of the arrows in FIG. 17 as the upper flange 1544B holds the upper jaw 1508 at a secondary pivoting location indicated at $P_2$—at the same time that the step of the cam surface element 1590 lifts the pins 1574 and the proximal portion 1558 of the upper jaw 1508 upward.

Thus, the system functions by providing a slidable cam mechanism for lifting the proximal end of the jaw while maintaining the medial jaw portion in a fixed position to thereby tilt the distal jaw to the second jaw-closed position, with the pivot occurring generally about secondary pivot $P_2$ which is distal from the primary pivot location $P_1$.

FIG. 18 next shows the reciprocating member 340 moved further distally wherein the elevated cam surfaces 1590 of lower flange 344A slides distally beyond the ends 1595 of rectangular pins 1574 thus causing the flanges 344A and 344B together with the trailing edge portions 1575 of the "I"-beam portion (FIG. 19) of the member 340 to apply very high compression forces over the entire length of the jaws as indicated by the arrows in FIG. 18. This position is termed a parallel jaw-closed position herein. Another advantage is that the jaw structure is in a "locked" position when the reciprocating member 340 is fully advanced.

Figure 20:
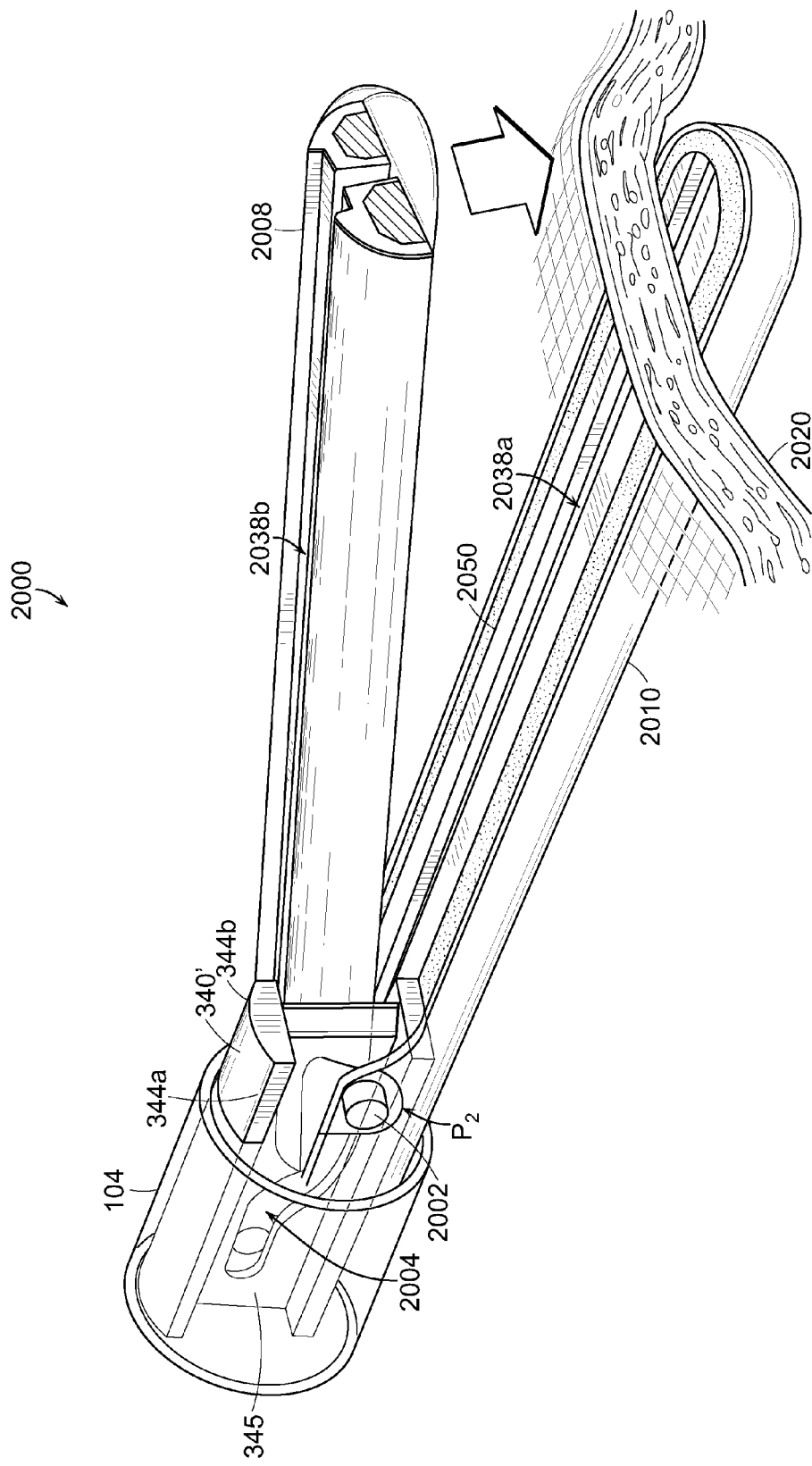
FIG. 20 illustrates one embodiment of an end effector comprising cam-pin actuated jaw members.
Figure 21:
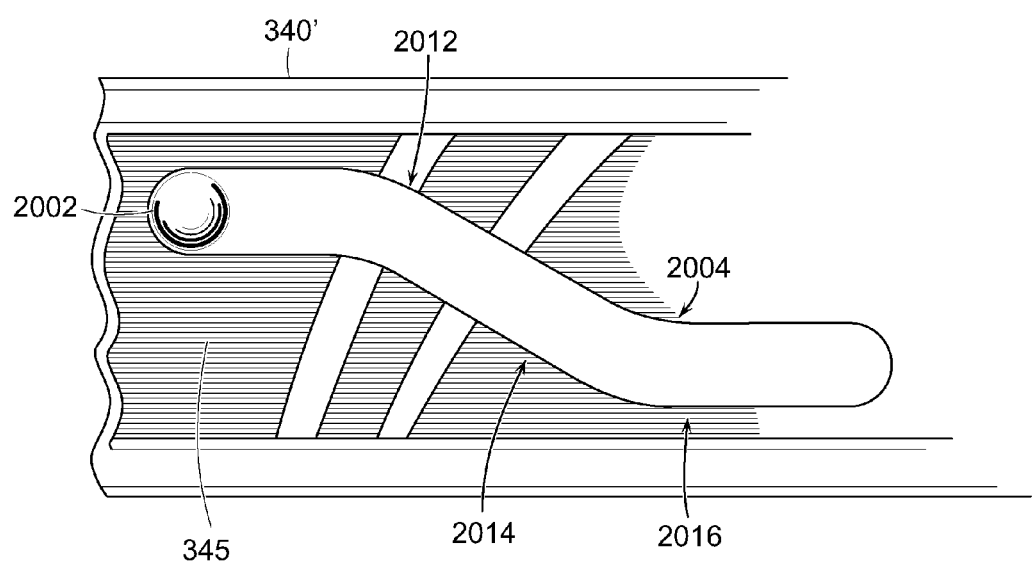
FIG. 21 illustrates one embodiment of the reciprocating member of FIG. 20 showing the cam slot.
Figure 22:
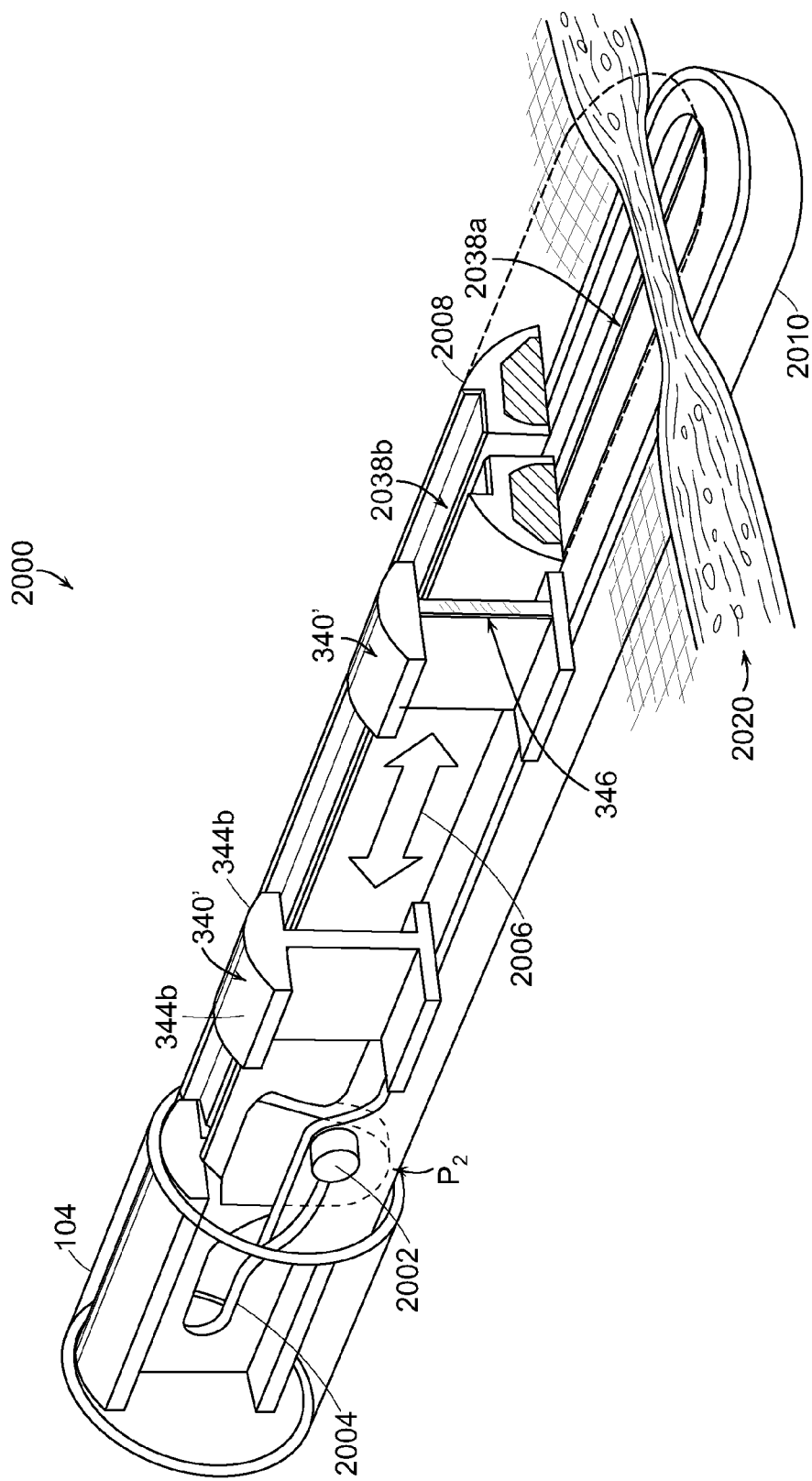
FIG. 22 illustrates one embodiment of the end effector of FIG. 20 in a closed position.

FIG. 20 illustrates one embodiment of an end effector 2000 comprising cam-pin actuated jaw members 2008, 2010. Tissue 2020 is shown between the members 2008, 2010. The end effector 2000 may provide increased opening force allowing it to be used in more dissecting applications. By increasing the functions that may be performed by the end effector 2000, the number of instrument changes during a procedure may be minimized. The upper rotating jaw member 2008 may pivot relative to the lower jaw member 2010 about a rolling pivot $P_2$. As illustrated, the jaw member 2008 may comprise a cam pin 2002 which extends through a cam slot 2004 defined by the reciprocating member 340'. The cam pin 2002 may be offset from the pivot point such that motion of the cam pin 2002 may tend to cause motion of the jaw member 2008. FIG. 21 illustrates one embodiment of the reciprocating member 340' showing the cam slot 2004. FIG. 22 illustrates one embodiment of the end effector 2000 in a closed position.

The cam slot 2004 may have a distal portion 2016, a transition portion 2014 and a proximal portion 2012 (Figure A2). The distal portion 2016 may be positioned low in the member 340' such that when the cam pin 2002 rides within the distal portion 2016 of the cam slot 2004, the jaw member 2008 may pivot about the pivot $P_2$ to the open position shown in FIG. 20. To close the jaw members 2008, 2010, the reciprocating member 340' may be pushed distally. As described above, transverse member 345 of the reciprocating member 340' may slide within respective slots 2038a, 2038b in the jaw members 2008, 2010. Flange portions 344B of the reciprocating member 340' may contact the jaw member 2008, forcing it to the closed position as described herein. Additionally, as the member 340' moves distally, the cam pin 2002 of the jaw 2008 may be pushed through the distal portion 2016 of the cam slot 2004, through the transition portion 2014 and into the proximal portion 2012. This may raise the portion of the jaw member 2008 including the cam pin 2002 relative to the pivot $P_2$, causing the jaw member 2008 to transition to the closed position shown in FIG. 22. Once the jaw member is in the closed position shown in FIG. 22, the member 340' may be pushed further in the distal direction to hold the jaw members 2008, 2010 together and/or to cause the distal edge 346 of the member 340' to transect tissue 2020.

Retracting the member 340' in the proximal position may cause the cam pin 2002 to translate from the proximal portion 2012, through the transition portion 2014 to the distal portion 2016. The process may serve to force the jaw member 2008 to the open position shown in FIG. 20. This opening process may be utilized by clinicians to transect tissue, dissect tissue and/or insert targeted tissues into the jaws during surgery during surgery. According to various embodiments, the cam pin embodiments described herein may provide superior opening force, allowing the clinician to use the end effector 2000 for dissection tasks that previously required a separate instrument.

Figure 23:
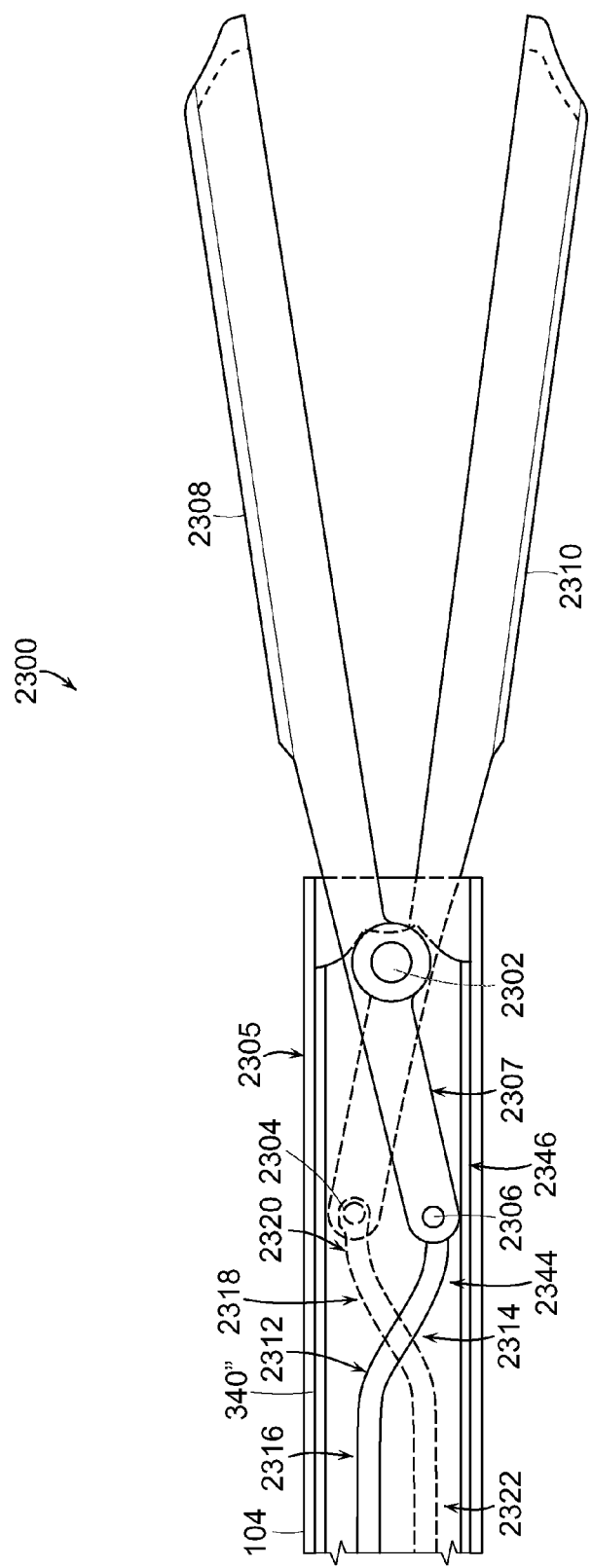
FIGS. 23-24 illustrate one embodiment of an end effector having a pair of movable, cam-pin actuated jaw members.
Figure 24:
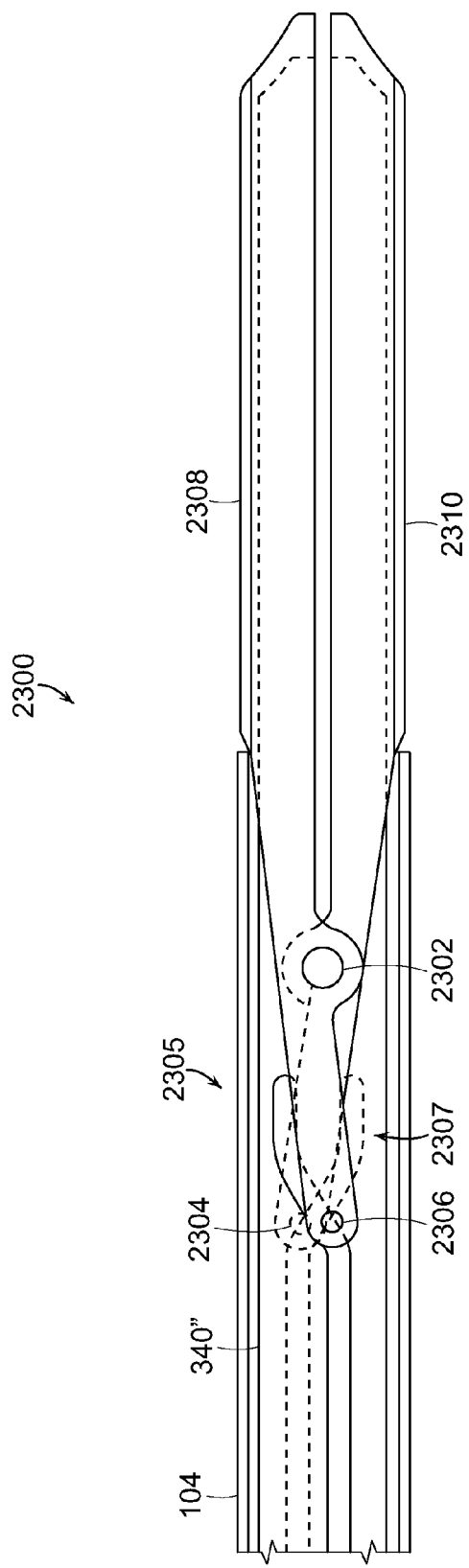

The cam pin concept shown in FIGS. 20-22 may also be used in embodiments having two movable jaw members. For example, FIGS. 23-24 illustrate one embodiment of an end effector 2300 having a pair of movable, cam-pin actuated jaw members 2308, 2310. The jaw members 2308, 2310 may be pivotable about a pivot pin 2302. The pin 2302 may be coupled to the shaft 104, as shown, or may be coupled to a clevis (not shown in FIG. 23), for example, as illustrated by clevis 112 shown in FIG. 1 above. The jaw members 2308, 2310 may comprise respective cam portions 2307, 2305. The cam portions 2307, 2305 may, in turn, comprise respective cam pins 2304, 2306. The cam pins 2304, 2306 may ride within a pair of cam slots 2312, 2314 of a reciprocating member 340". According to various embodiments, the cam slots 2312, 2314 may not extend all the way through the member 340" (e.g., the cam slots 2312 may thought of as cam grooves). This may prevent the respective pins 2304, 2306 from interfering with one another.

Each of the cam slots 2314, 2312 may comprise distal portions 2320, 2346, transition portions 2318, 2344, and proximal portions 2316, 2322. When the member 340" is pulled proximally, as shown in FIG. 23, the jaw members 2308, 2310 may be in the illustrated open position and the cam pins 2304, 2306 may rest in the distal portions 2320, 2346 of the respective cam slots 2312, 2314. To close the jaws, the reciprocating member 340" may be pushed distally, as shown in FIG. 24. This may cause the cam pins 2304, 2306 to slide from the distal portions 2320, 2346 through the transition portions 2318, 2344 to the proximal portions 2316, 2322 of the cam slots 2312, 2314. This may, as shown, cause the jaw members 2308, 2310 to pivot about the pivot pin 2302 to the closed position shown in FIG. 24. To open the jaw members 2308, 2310, the reciprocating member 340" may be pulled distally to the position shown in FIG. 23. This may cause the cam pins 2304, 2306 to transition back to the distal portions 2320, 2346 of the cam slots 2312, 2316 which, in turn, may force the jaw members 2308, 2310 to the open position.

Figure 25:
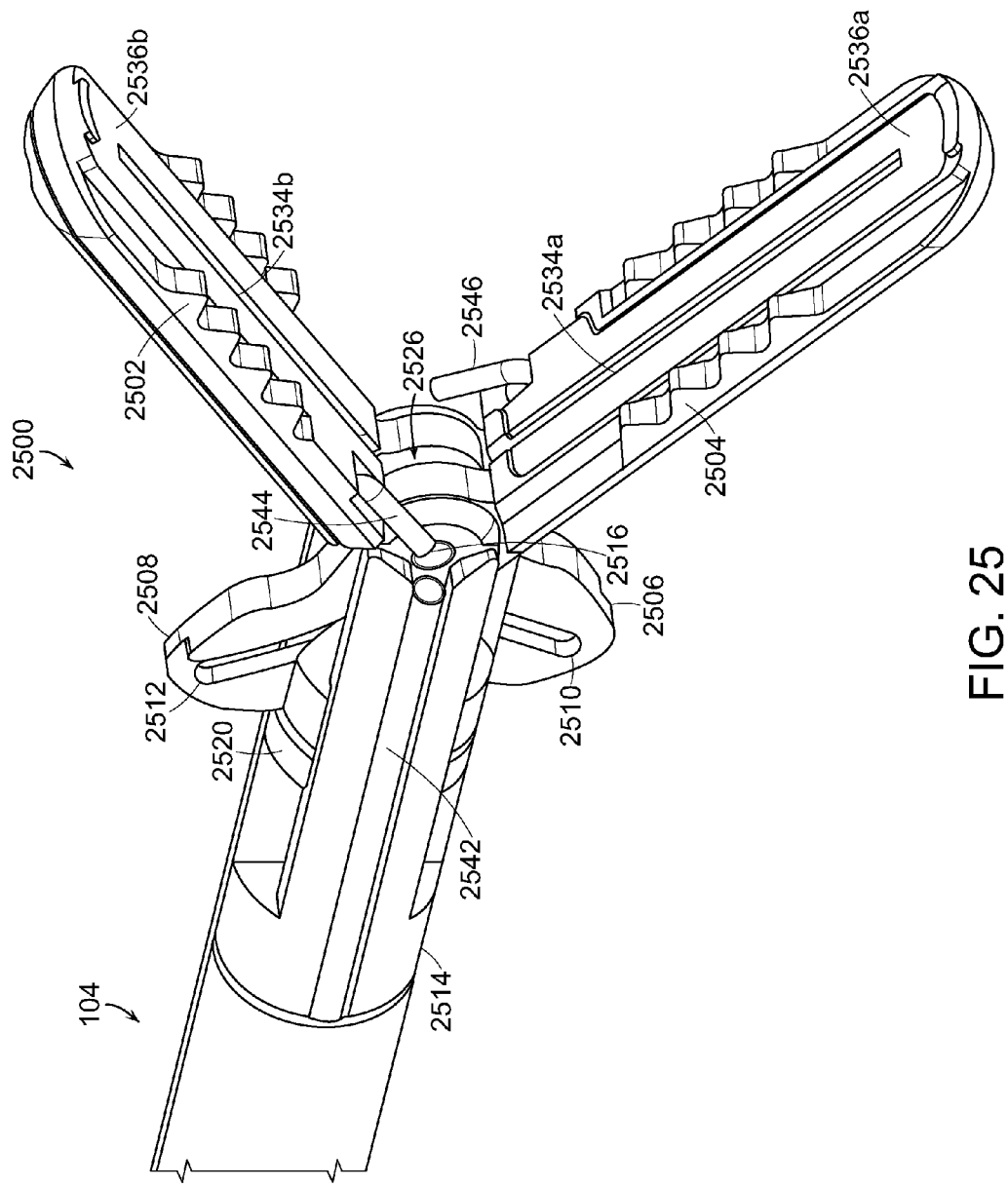
FIGS. 25 and 26 illustrate one embodiment of an end effector comprising cam-actuated jaw members in an open position.
Figure 26:
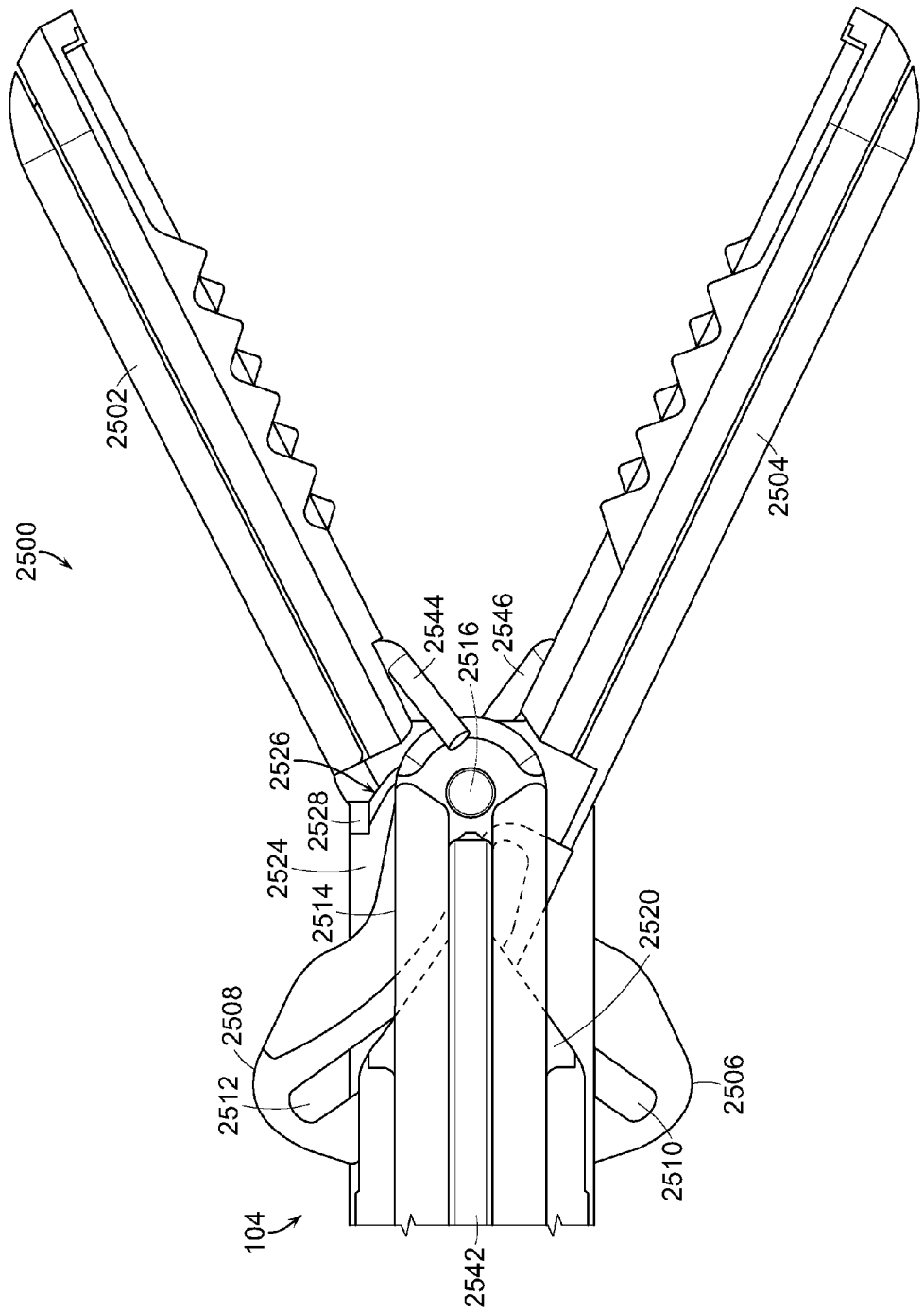

FIGS. 25 and 26 illustrate one embodiment of an end effector 2500 comprising cam-actuated jaw members 2502, 2504 in an open position. The jaw members 2502, 2504 may be pivotably coupled to a clevis 2514 at a pivot point 2516 such that the jaw members 2502, 2504 may transition from the open position shown in FIGS. 25 and 26 to the closed position shown in FIGS. 27 and 28 and described below. As shown in FIGS. 25-28, both jaw members 2502, 2504 may be pivotable about the pivot point 2516. In some embodiments, however, one of the jaw members may be stationary. The pivot point 2516 may be any suitable kind of joint and, in various embodiments, may comprise a pin. The jaw members 2502, 2504 may comprise tissue-engaging surfaces or planes 2536a, 2536b that may be similar to the tissue engaging planes 350a, 350b described above and may be, or comprise, one or more electrodes for delivering energy to tissue held between the jaw members 2502, 2504, as described herein. Wire conduits 2542, 2544, 2546 may be present, as shown, to carry wires from the electrodes to the generator 324, e.g., via the shaft 104.

Each of the jaw members 2502, 2504 may comprise respective cam portions 2506, 2508 positioned substantially or entirely proximally from the pivot point 2516. The cam portions 2506, 2508 may define cam slots 2510, 2512. A shuttle 2520 may be coupled to the cam portions 2506, 2508 via a cam pin 2518 received through both of the cam slots 2510, 2512. According to various embodiments, the cam pin 2518 may comprise two cam pins on opposite sides of the shuttle 2520. Also, according to various embodiments, the drive pin 2518 or pins may not extend all the way through the cam slots 2510, 2512.

Figure 27:
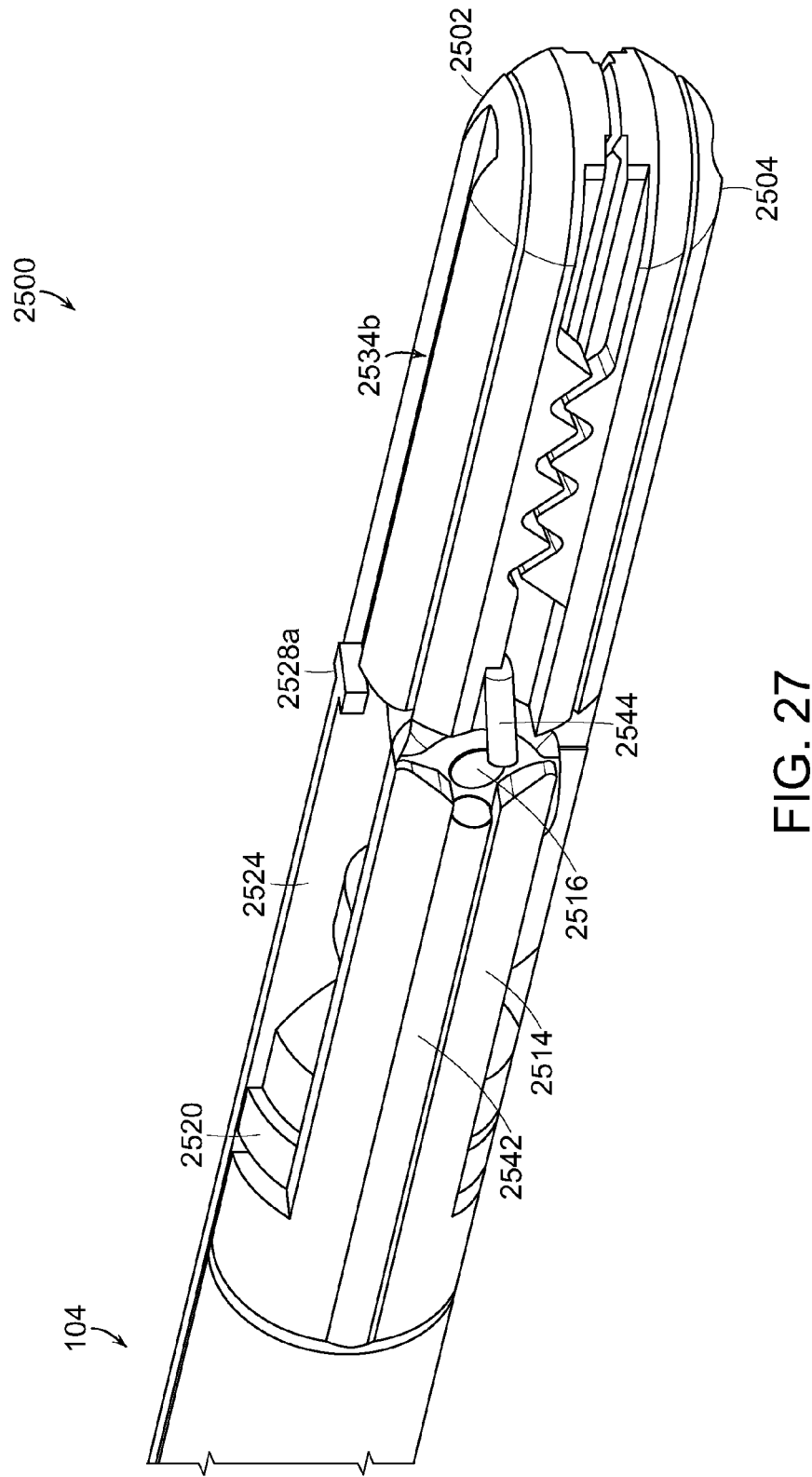
FIGS. 27 and 28 illustrate one embodiment of the end effector of FIGS. 25 and 26 with the jaw members in a closed position.
Figure 28:
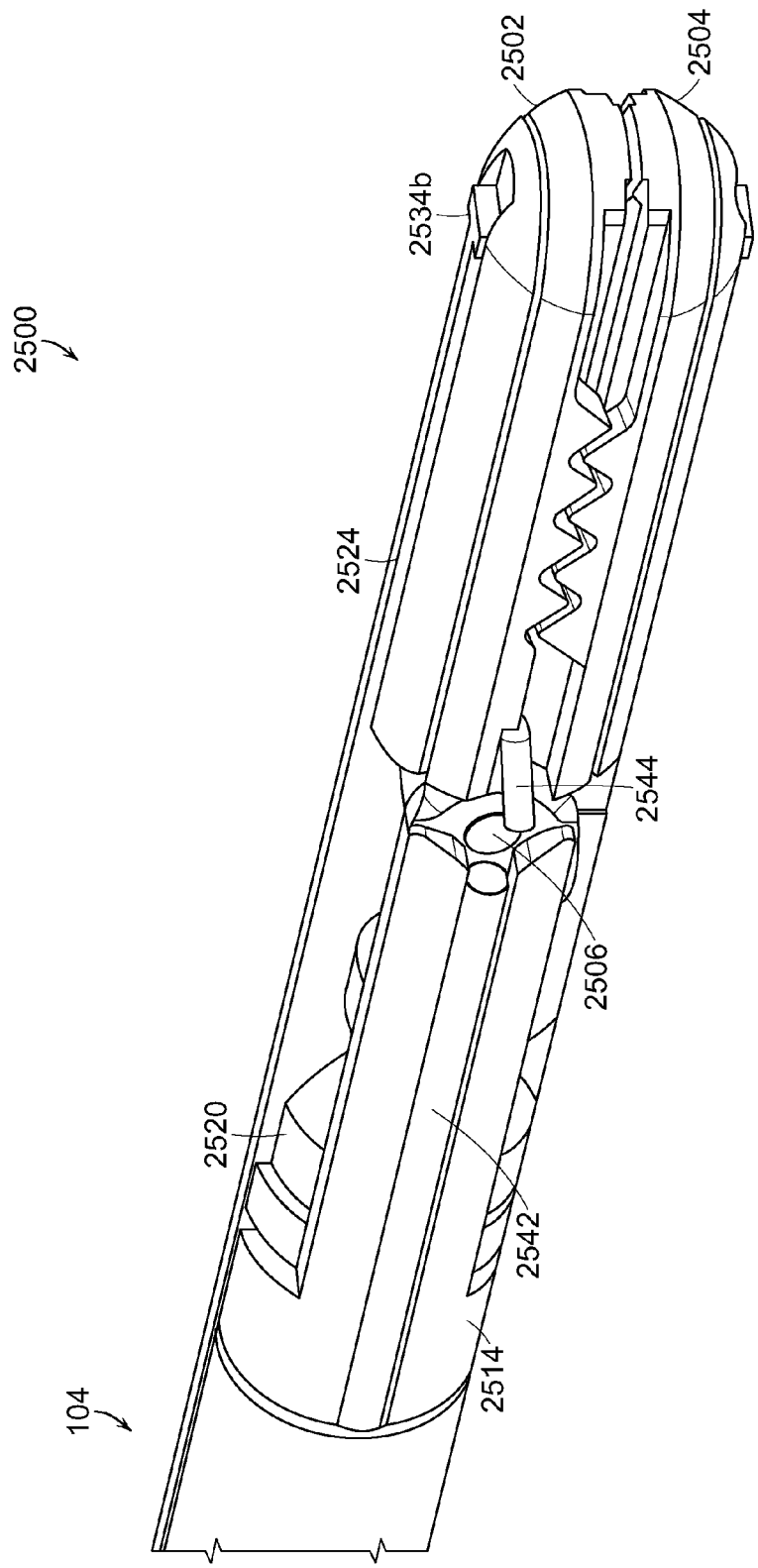

The cam slots 2510, 2512 may be curved such that distal motion of the shuttle 2520 may cause the jaw members 2502, 2504 to pivot about the pivot point 2516 to the open position shown in FIG. 25. Similarly, proximal motion of the shuttle 2520 may cause the jaw members 2502, 2504 to pivot about the pivot point 2516 to a closed position, for example, as shown in FIGS. 27 and 28. Distal and proximal motion of the shuttle 2520 may be effected by a translating member 2530 (FIG. 30), which may extend proximally to the handle 102. At the handle 102, an actuator, such as actuator 113 may be coupled to the translating member 2530 such that a clinician may move the actuator 113 in order to cause distal and proximal motion of the translating member 2530. Distal and proximal motion of the translating member 2530 may cause similar distal and proximal motion of the shuttle 2520, which may, in turn cause the jaws 2502, 2504 to open and close.

Figure 29:
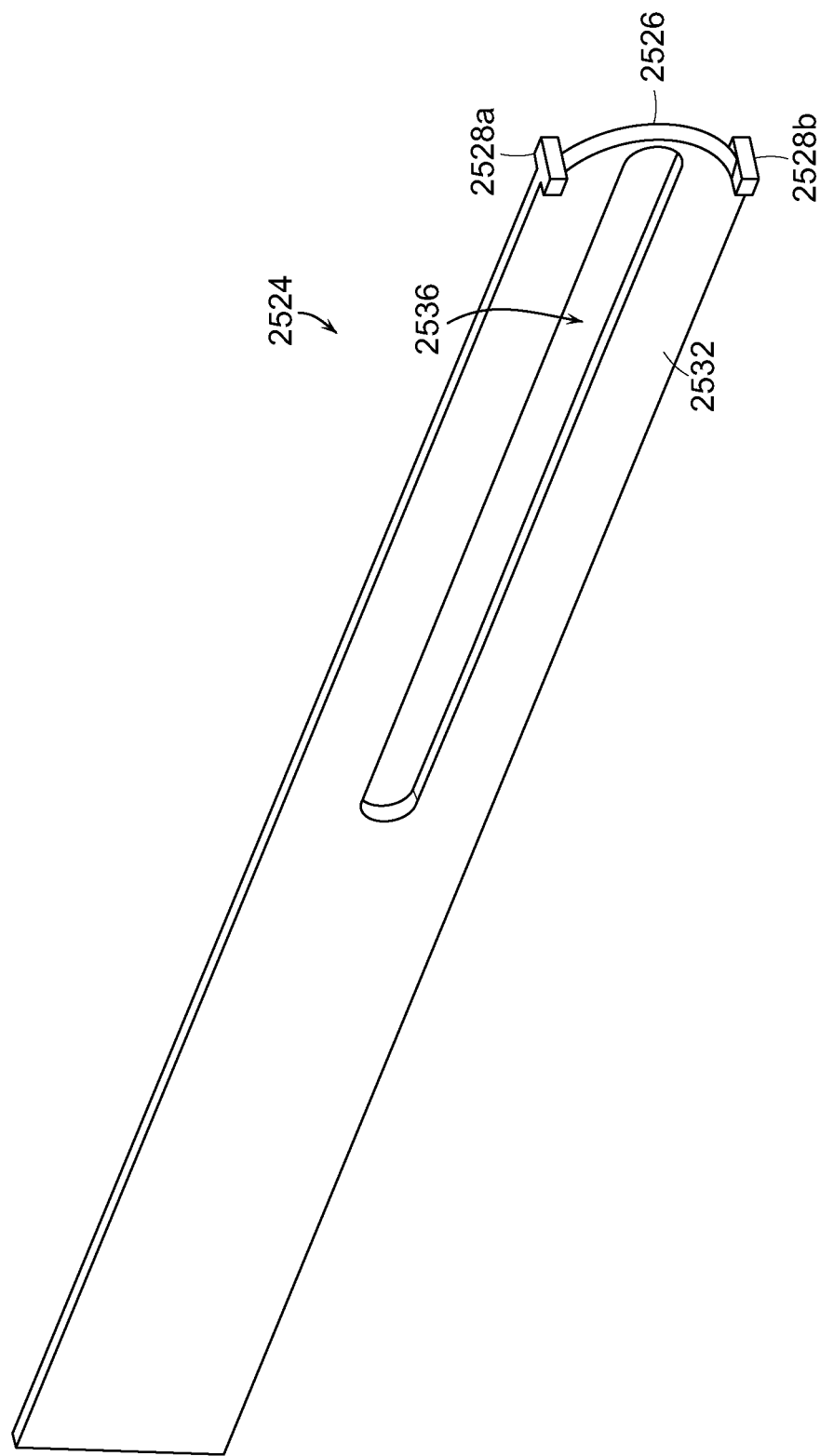
FIG. 29 illustrates one embodiment of the reciprocating member of FIGS. 25-28.

The end effector 2500 may also comprise a reciprocating I-beam member 2524 similar to the member 340 described above. FIG. 29 illustrates one embodiment of the reciprocating member 2524. The member 2524 may comprise a transverse element 2532 and a pair of flanges 2528a, 2528b. The transverse element 2532 may comprise a distally directed leading edge or blade 2526, which may be sharpened or be electrically active to cut tissue. When the jaw members 2502, 2504 are in the closed position shown in FIGS. 27 and 28, the transverse element may be translated distally to cut tissue held between the jaw members 2502, 2504 and, in various embodiments, to provide a compressive force tending to hold the jaw members 2502, 2504 together. For example, the transverse element 2532 of the reciprocating member 2524 may be adapted to slide within slots 2534a, 2534b in the jaw members 2502, 2504. Flanges 2528a, 2528b may ride above the slots 2534a, 2534b. As the reciprocating member 2524 is translated distally through the slots 2534a, 2534b, the flanges 2528a, 2528b may exert a compressive force on the jaw members 2502, 2504, tending to force the jaw members 2502, 2504 together. The reciprocating member 2524 may be actuatable from the handle 102 of the instrument by any suitable mechanism, such as actuator 113, which may be coupled to a proximal end of member 2524. The proximal end and medial portion of member 340 may be dimensioned to reciprocate within bore 308 of the shaft 104.

Figure 30:
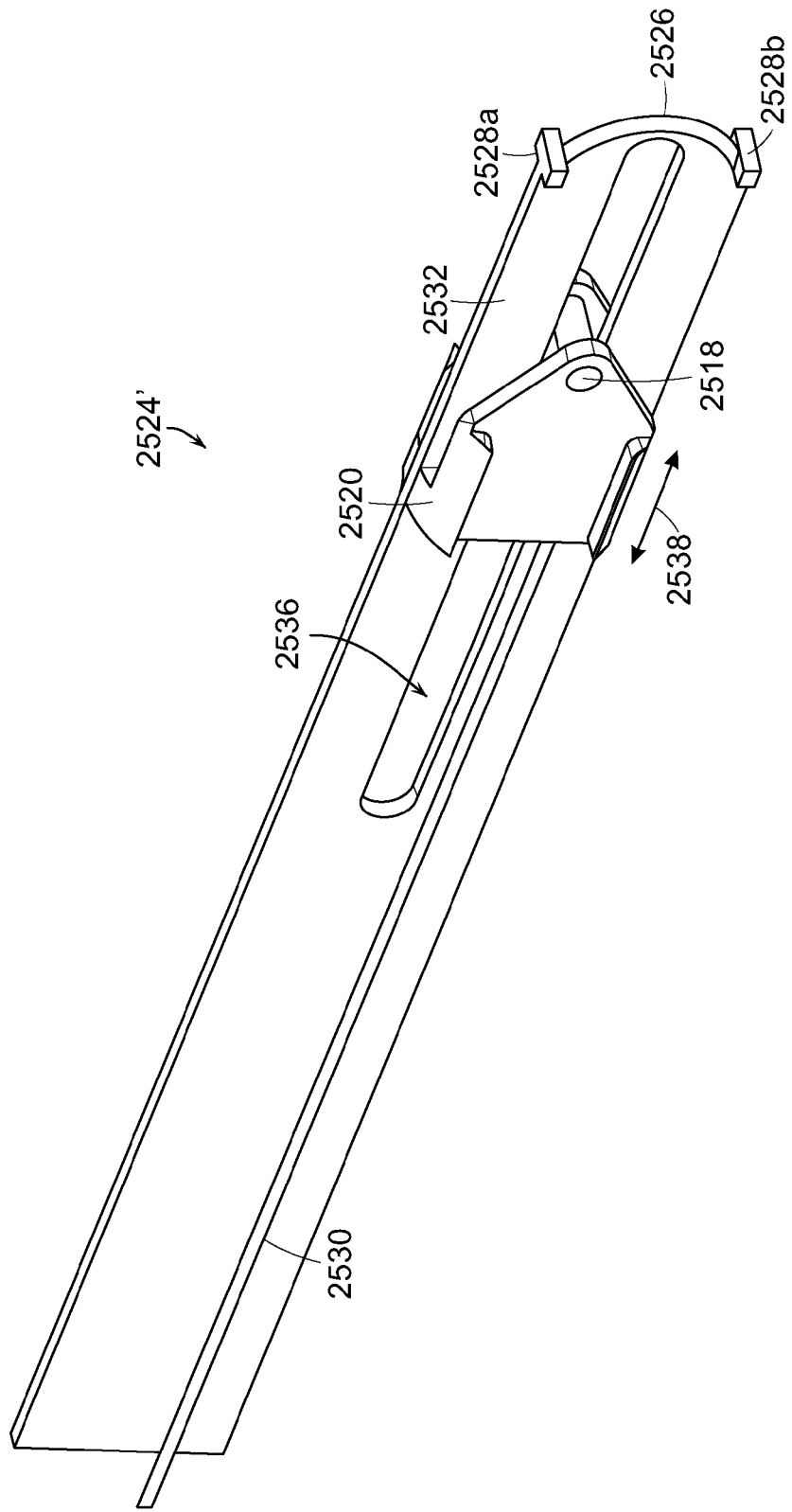
FIG. 30 illustrates one embodiment of the reciprocating member of FIG. 29 with a shuttle and cam pin shown.

According to various embodiments, the reciprocating member 2524 and the shuttle 2520 may be configured to translate distally and proximally substantially independent of one another. For example, the reciprocating member 2524 may define a slot 2536 in the transverse member 2532 for receiving the shuttle 2520 and the cam pin 2518. FIG. 30 illustrates one embodiment of the reciprocating member 2524 with the shuttle 2520 and cam pin 2518 shown. The shuttle 2520 and cam pin 2518 may be movable transversely and distally relative to the reciprocating member 2524 (e.g., as shown by arrow 2538). In this way, the reciprocating member 2524 may have a range of motion along the arrow 2538 while the shuttle 2520 is stationary. Likewise, the shuttle 2520 may have a range of motion along the arrow 2538 while the reciprocating member 2524 remains stationary.

Figure 31:
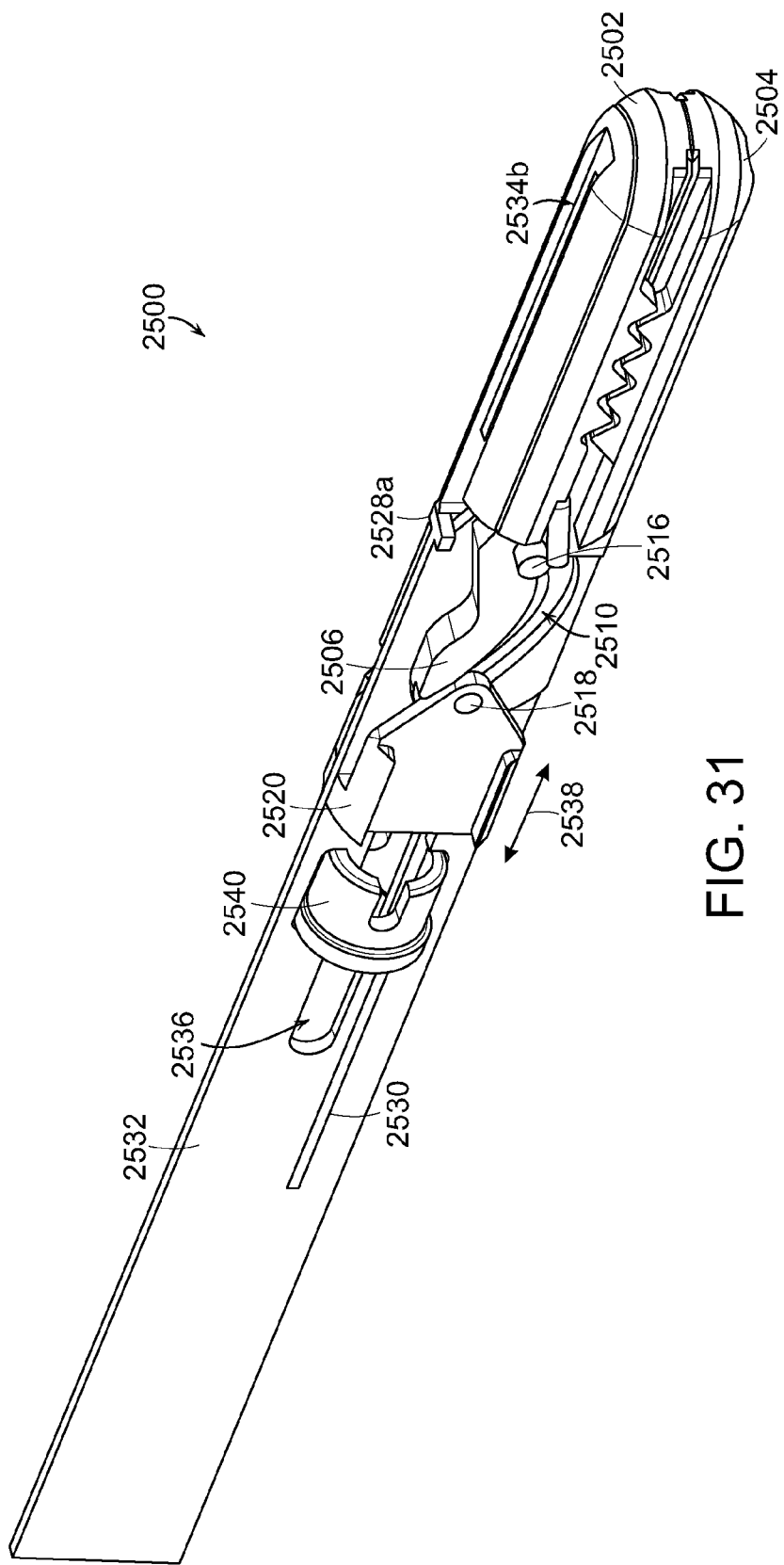
FIG. 31 illustrates one embodiment of the end effector of FIG. 25 with the clevis and the shaft shown in FIG. 25 not shown.
Figure 32:
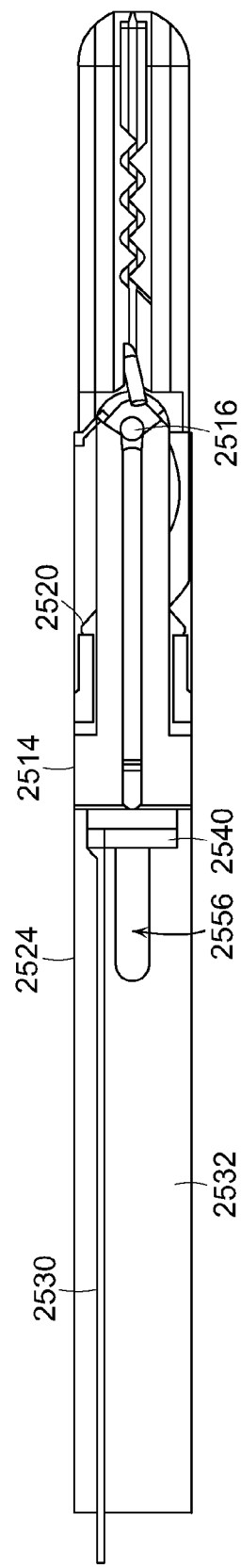
FIG. 32 illustrates one embodiment of the end effector as shown in FIG. 31 with the clevis also shown.
Figure 33:
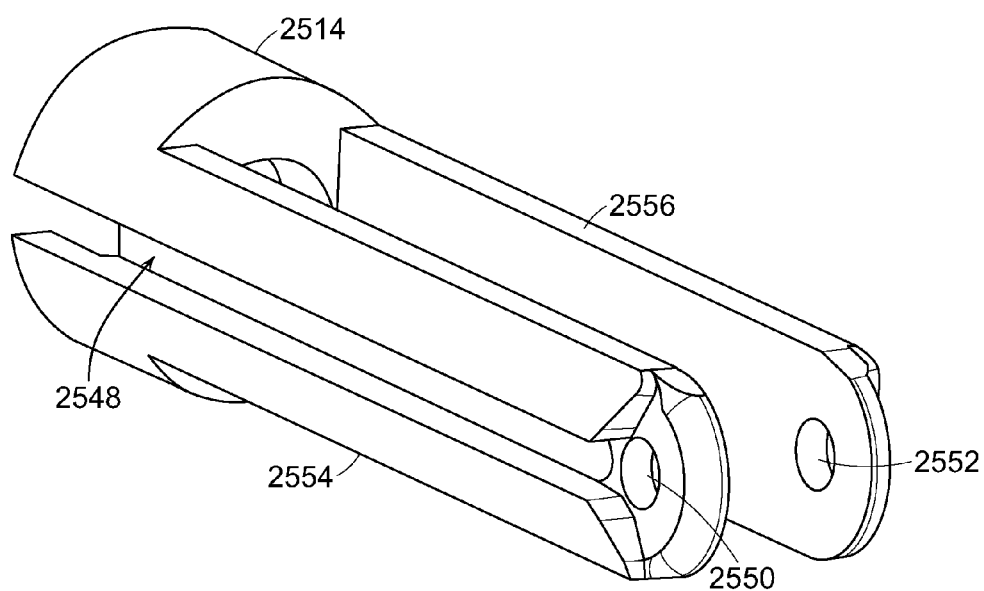
FIG. 33 illustrates one embodiment of the clevis of the end effector of FIG. 25.

FIG. 31 illustrates one embodiment of the end effector 2500 with the clevis 2514 and the shaft 104 shown in FIG. 25 omitted. The cam pin 2518 is shown riding within the slot 2536 in the reciprocating member 2524 as well as within the slot 2510 of the cam portion 2506 of the jaw member 2502. A coupling 2540 for fastening the clevis 2514 to the shaft 104 is also illustrated. FIG. 32 illustrates one embodiment of the end effector 2500 as shown in FIG. 31 with the clevis 2514 also shown. FIG. 33 illustrates one embodiment of the clevis 2514. The clevis 2514 may comprise a pair of arms 2554, 2556. Each arm 2554, 2556 may define respective holes 2550, 2552 at the pivot point 2516, e.g., for receiving a pivot pin (not shown). As illustrated in FIG. 32, the shuttle 2520 may ride between the arms 2554, 2556. According to various embodiments, the arms 2554, 2556 may define recesses such as recess 2548 for receiving wire conduits (e.g., conduit 2542 shown in FIG. 25).

Figure 34:
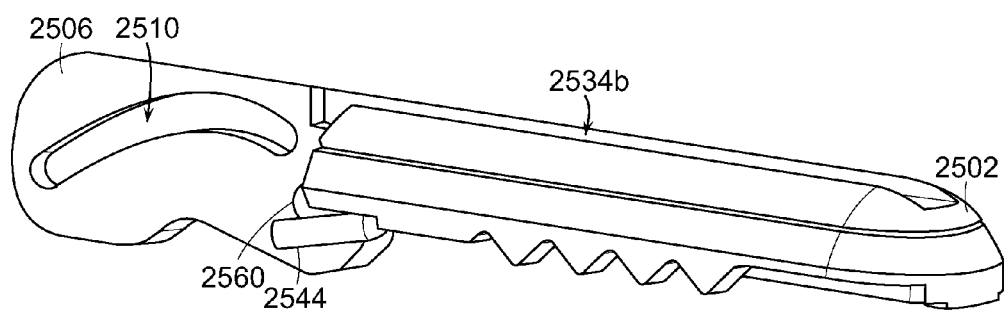
FIGS. 34 and 35 illustrate one embodiment of the upper jaw member of the end effector of FIG. 25.
Figure 35:
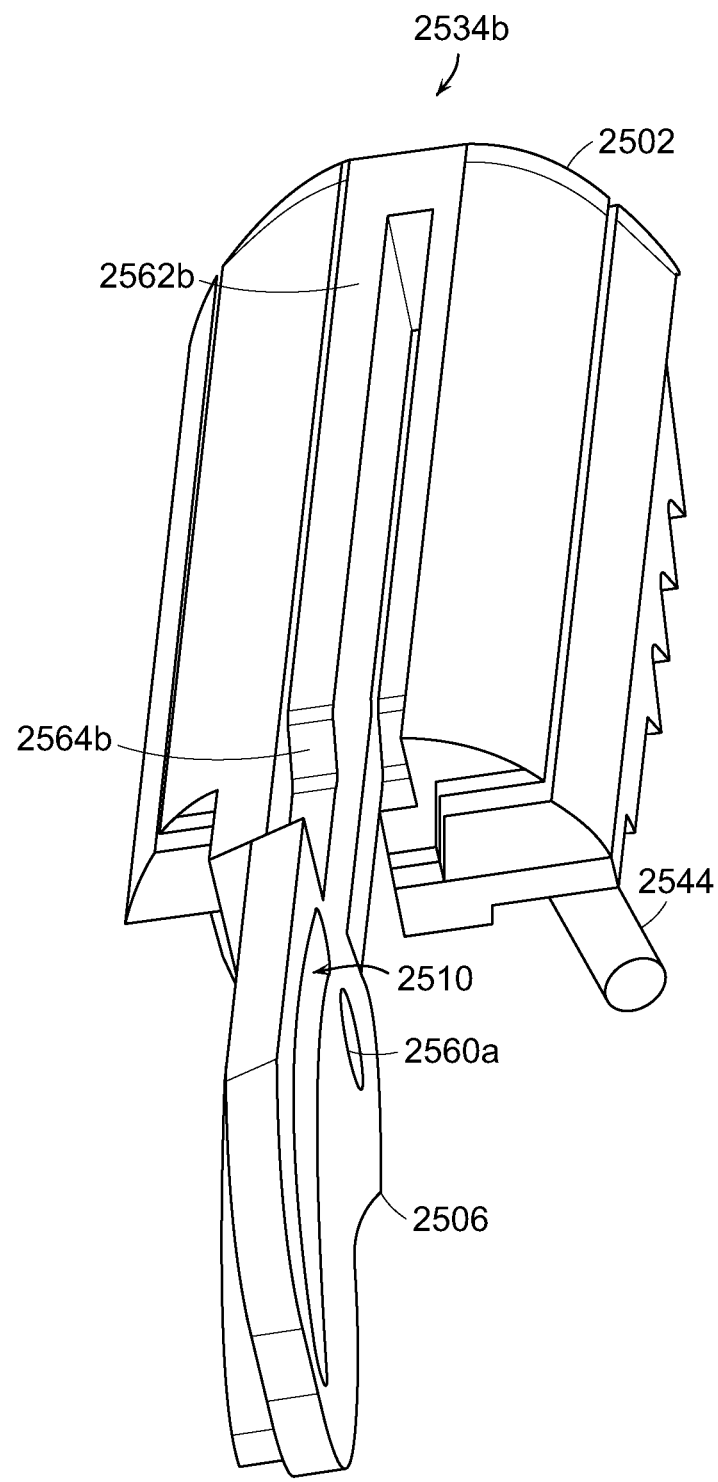
Figure 36:
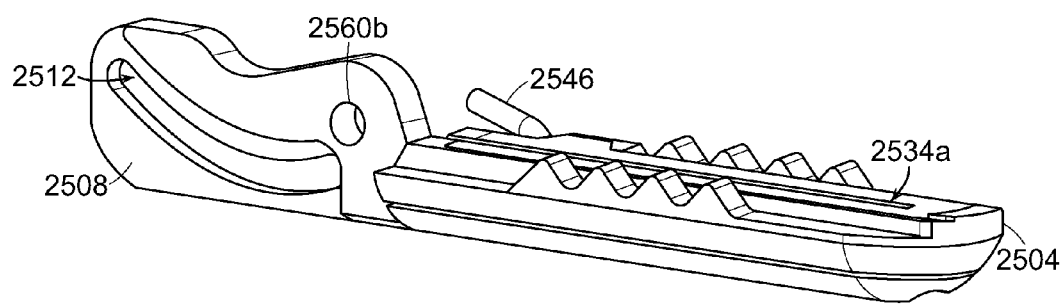
FIGS. 36 and 37 illustrate one embodiment of the lower jaw member of the end effector of FIG. 25.
Figure 37:
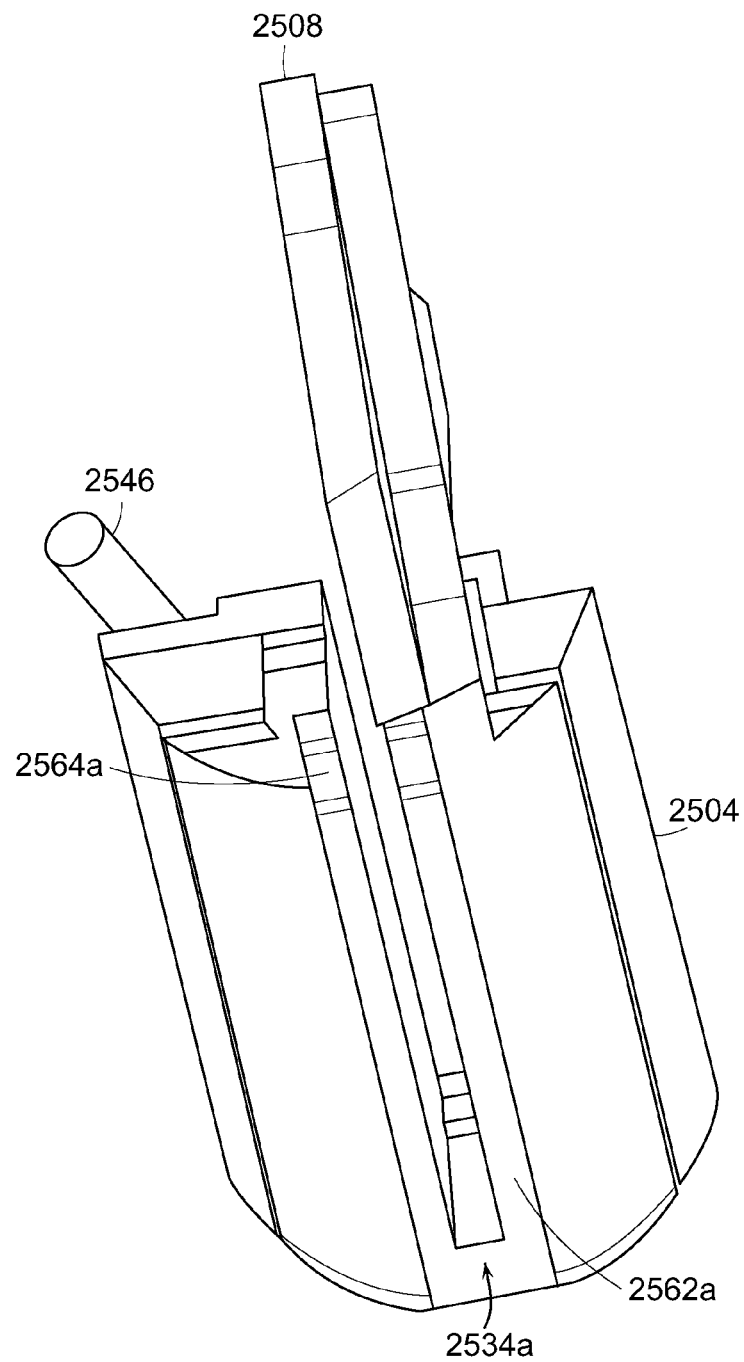

FIGS. 34 and 35 illustrate one embodiment of the jaw member 2502 of FIG. 25. As shown, the jaw member 2502 may define a hole 2560*a* at about the pivot point 2516. For example, the hole 2560*a* may receive a pivot pin. The perspective shown in FIG. 35 provides a view of the slot 2534*b*. A surface 2662*b* may partially or completely surround the slot 2534*b*. The surface 2562*b* may receive the flange 2528*a* of the reciprocating member 2524 as it translates distally. The flange 2528*a* may exert a force on the surface 2562*b*, and therefore the jaw member 2502, (flange 2528*b* may exert a force on the surface 2562*a* and therefore the jaw member 2504), tending to cause the jaw members 2502, 2504 to the closed position. At its proximal portion, the surface 2562*b* may define an incline 2564*b* for receiving the flange 2528*a*. For example, the incline 2564*b* may allow the flange 2528*a* to engage the slot 2534*b* when the jaws 2502, 2504 are not in a closed or completely closed position. FIGS. 36 and 37 illustrate one embodiment of the jaw member 2504 of FIG. 25. As illustrated, the jaw member 2504 may comprise a hole 2560*b*, surface 2562*a* and incline 2564*a* similar to those of the jaw member 2502 described above.

Referring back to FIGS. 25 through 28, FIG. 25 shows the end effector 2500 with the jaw members 2502, 2504 in an open position. In use, the jaw members 2502, 2504 may be placed around tissue, such as a bodily lumen to be severed and sealed. When the end effector 2500 is properly positioned, the clinician may close the jaw members 2502, 2504 by operating an actuator, such as 113, on the handle 102. This may cause the translating member 2530 to translate proximally, pulling the shuttle 2520 proximally along with the cam pin 2518. This may pull the cam pin 2518 proximally within the cam slots 2510, 2512, causing the jaw members 2502, 2504 to pivot about the pivot point 2516 to the closed position shown in FIG. 27. The clinician may then cause the reciprocating member 2524 to extend distally (e.g., by using the actuator 113 or another actuator at the handle 102). This may cause the reciprocating member 2524 to be received into the respective slots 2534*a*, 2534*b*. Flanges 2528*a*, 2528*b* may contact surfaces 2562*a*, 2562*b*, exerting a force on the jaw members 2502, 2504 tending to further close them, as shown in FIG. 28. The cutting edge 2526 of the reciprocating member 2524 may transect tissue held within the jaws. According to various embodiments, the reciprocating member may be extended distally before the jaw members 2502, 2504 are closed, or completely closed. For example, the flanges 2528*a*, 2528*b* may engage the inclines 2564*a*, 2564*b*, exerting a force on the jaw members 2502, 2504 tending to close them. In various embodiments, severed tissue within the jaws 2502, 2504 may be sealed, for example, utilizing the electrical energy techniques described herein. To open the jaw members 2502, 2504, the reciprocating member 2524 may be withdrawn proximally from the slots 2534*a*, 2534*b*. The shuttle 2520 may be pushed distally, for example, by exerting a distally directed force on the translating member 2530 (e.g., via the handle 102). Distal motion of the shuttle 2520 may cause the cam pin 2518 to slide distally within the cam slots 2510, 2512. This may, in turn force the jaw members 2502, 2504 to the open position. In various surgical situations, this may allow the clinician to dissect or separate tissue with the instrument 100. Allowing the clinician to transect and seal as well as dissect with the same instrument 100 may minimize the number of instrument changes required during an operation, thus reducing time and potentially cost.

Figure 38:
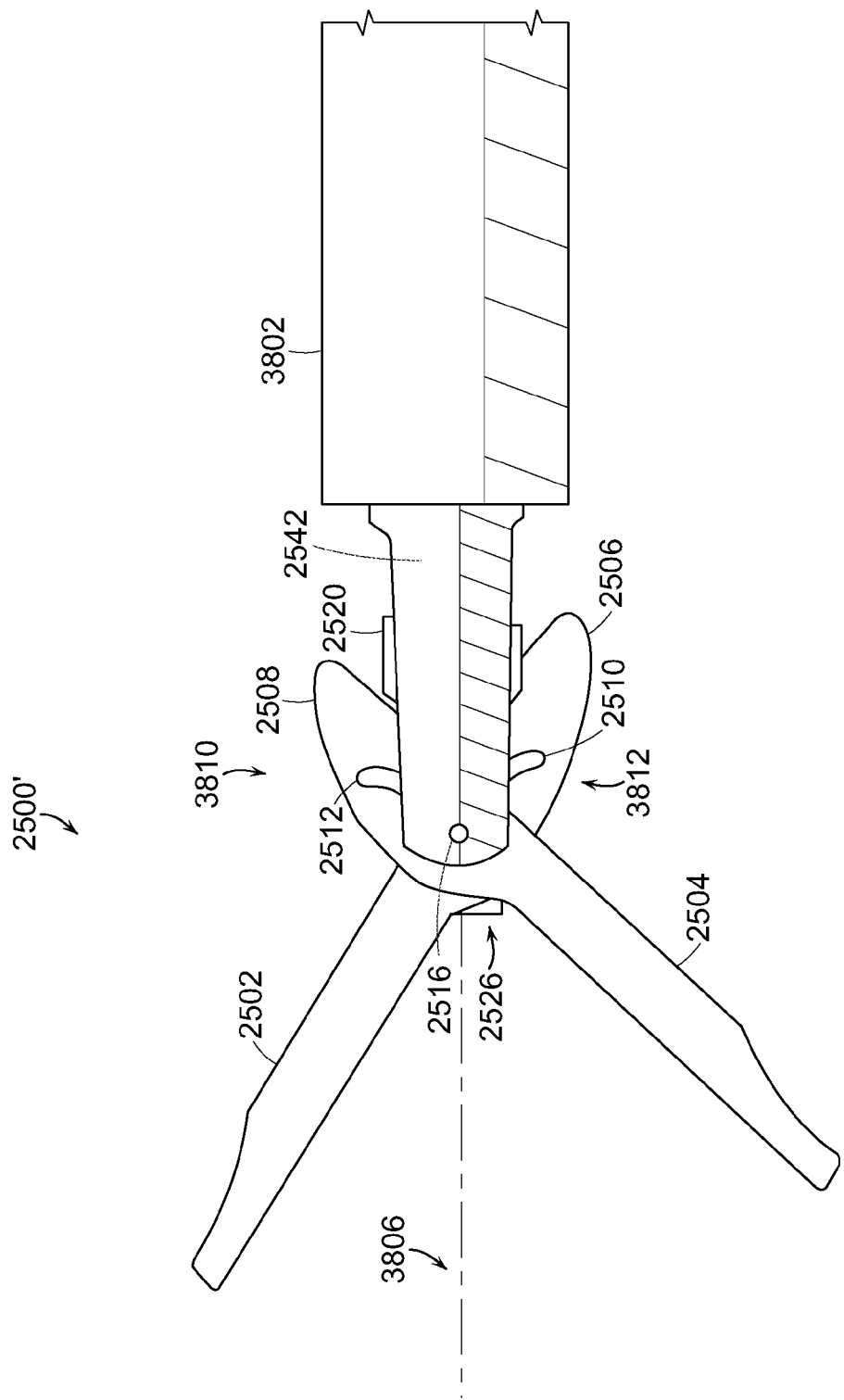
FIGS. 38-40 illustrate one embodiment of an end effector comprising an overtube for providing closing force to jaw members.
Figure 39:
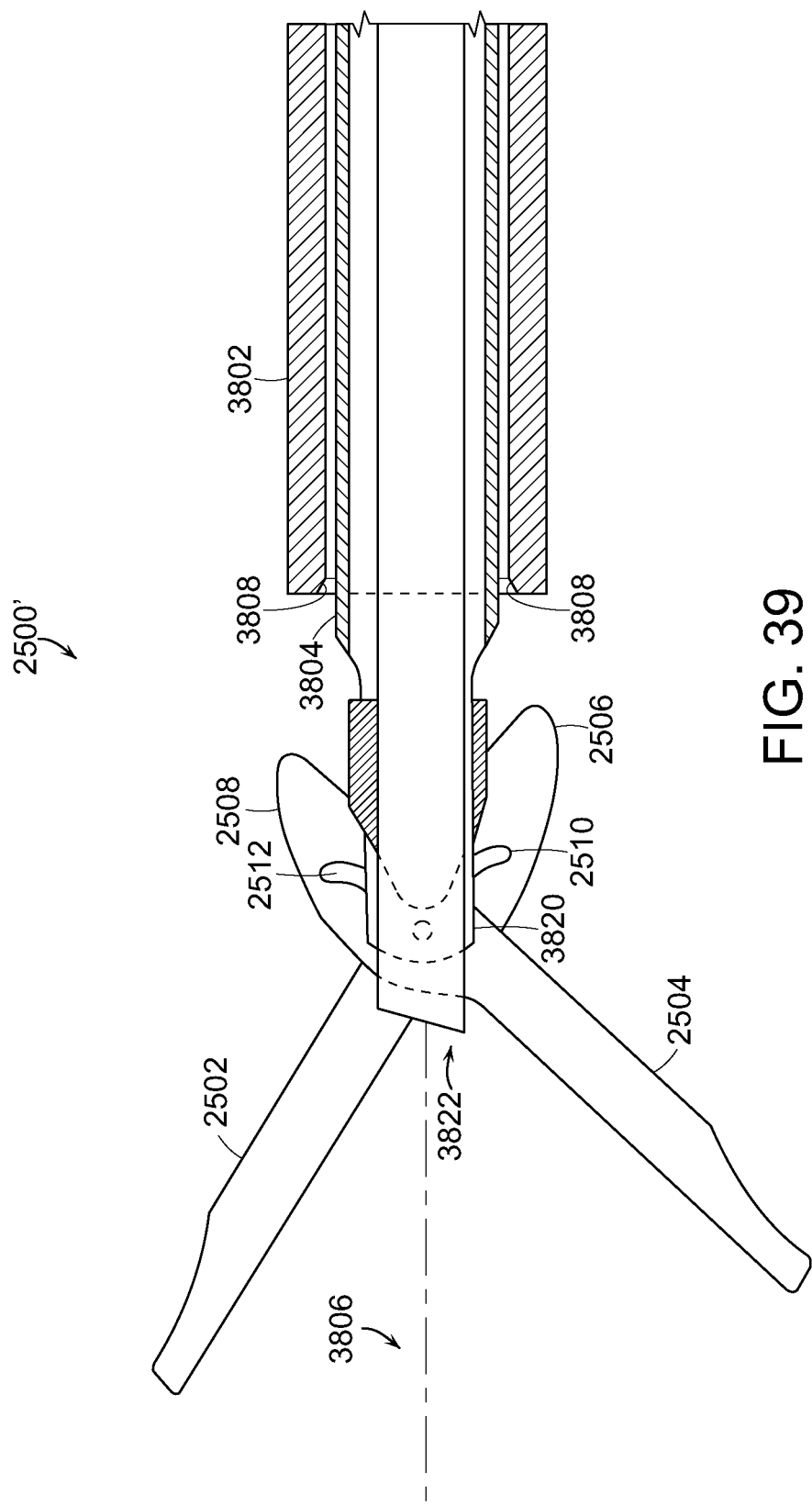
Figure 40:
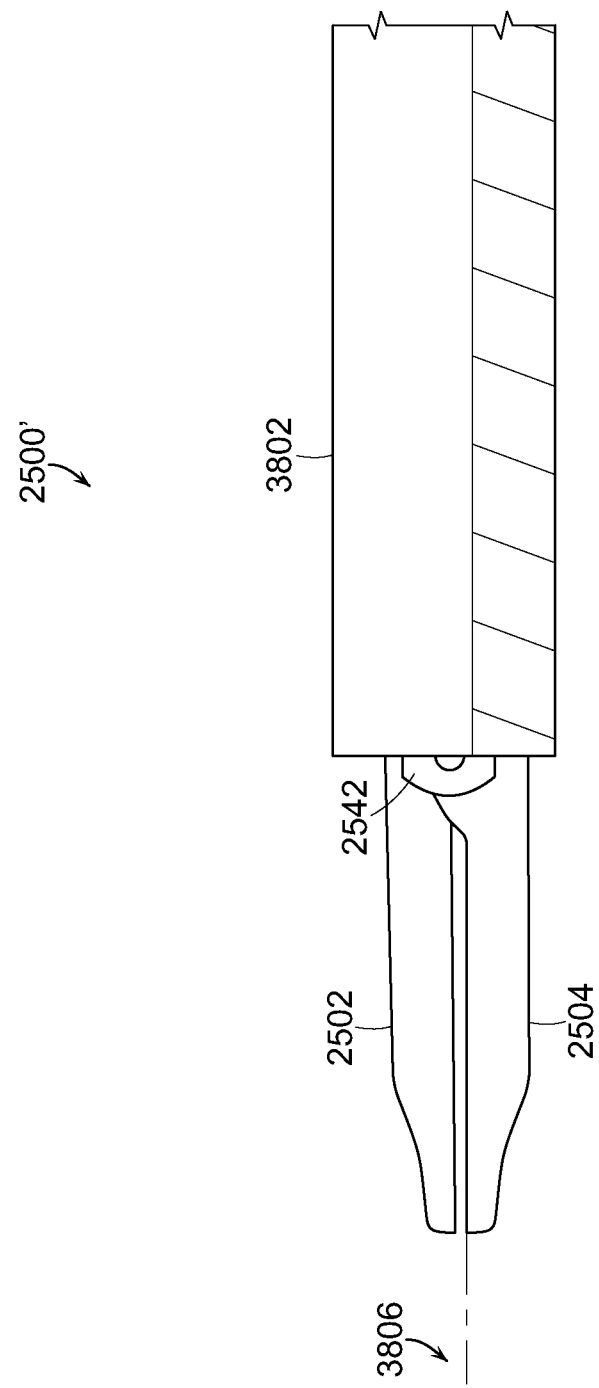

FIGS. 38-40 illustrate one embodiment of an end effector 2500' comprising an overtube 3802 for providing closing force to jaw members 2502, 2504. As illustrated in FIGS. 25-26 and 38-39, the respective cam portions 2508, 2510 of the jaw members 2502, 2504 may protrude away from a longitudinal axis 3806 of the end effector 2500'. As the jaw members 2502, 2504 are closed, as shown in FIGS. 27-28 and 40, the cam portions 2508, 2510 translate towards the axis 3806. According to various embodiments, additional clamping force between the jaw members 2502, 2504 may be obtained by forcing the cam portions 2508, 2510 towards the axis 3806. This may be performed by an overtube 3802. The overtube 3802, like the reciprocating member 2524 and shuttle 2520 may be translatable distally and proximally by the clinician from the handle 102. To close the jaw members 2502, 2504, the shuttle 2520 may be translated proximally, causing the jaw members 2502, 2504 to pivot towards the axis 3806, as illustrated and described with reference to FIGS. 27-28. Overtube 3802 may then be translated distally, where it may contact the cam portions 2508, 2506, tending to force them and their respective jaw members 2502, 2504 towards the longitudinal axis 3806. This may provide additional clamping force tending to force the jaw members 2502, 2504 together towards the longitudinal axis 3806. In some embodiments, the overtube 3802 may be shortened in length to more closely resemble a ring for applications involving flexible shafts. This would be of particular benefit for use in flexible endoscopic applications.

According to various embodiments, the shapes of the cam portions 2506 and 2508 and/or the overtube 3802 may be optimized to reduce the force necessary to force the overtube 3802 distally and/or to increase the compression force put on the jaw members 2502, 2504. For example, the cam portions 2506, 2508 may have curved sections 3810, 3812 positioned to contact the overtube 3802. The curved portions may be shaped to act as a camming surface to guide the overtube 3802 over the cam portions 2506, 2508 and progressively increase the compressive force provided by the overtube 3802 as it is translated distally. In some embodiments, the overtube 3802 may also comprise beveled camming surfaces 3808 around its interior distal edge to also guide the overtube 3802 over the cam portions 2506, 2508 and progressively increase the compressive force provided by the overtube 3802 as it is translated distally. Also, according to various embodiments, it will be appreciated that the end effector 2500' may utilize a reciprocating member 2524 with flanges 2528*a*, 2528*b*, as illustrated in FIGS. 29-31. The flanges 2528*a*, 2528*b* may serve, as described, to provide additional compressive force as the reciprocating member 2524 is translated distally. In other various embodiments, a reciprocating member 2520 may be used, as shown in FIG. 39. The reciprocating member 2520 may comprise a sharp leading edge for severing tissue, and may traverse within slots 2534*a*, 2534*b* of the respective jaw member 2502, 2504. The member 2520, however, may lack flange members, such as 2528*a*, 2528*b*. Accordingly, embodiments comprising a reciprocating member such as the member 2520 may rely on the cam portions 2508, 2506, cam slots 2512, 2510, and overtube 3802 to close the jaw members 2502, 2504 and provide compressive force.

Figure 41:
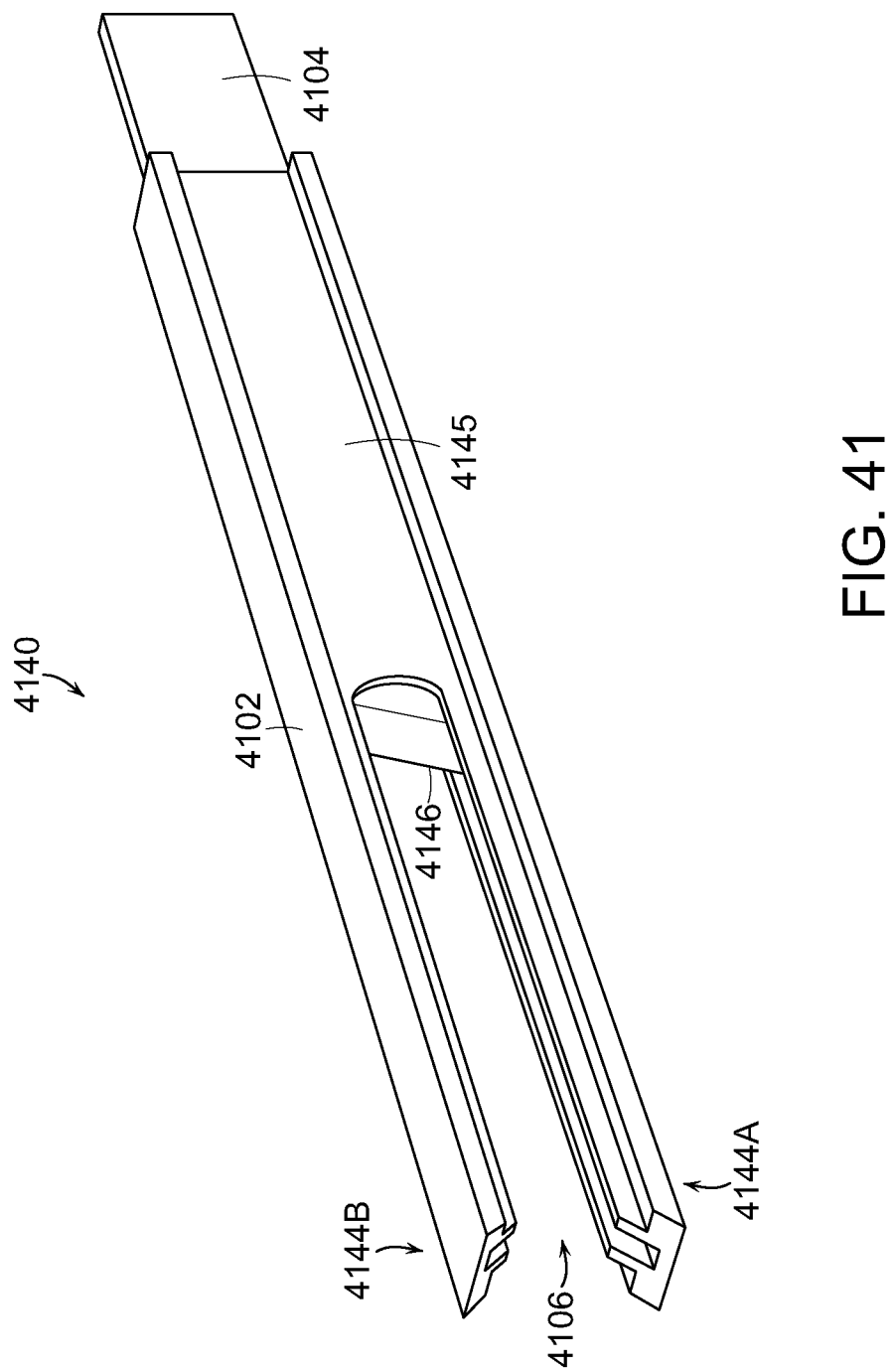
FIGS. 41-43 illustrate one embodiment of a reciprocating member that may be used in any of the end effectors described above in order to allow closure of jaw members without the advancement of a blade.
Figure 42:
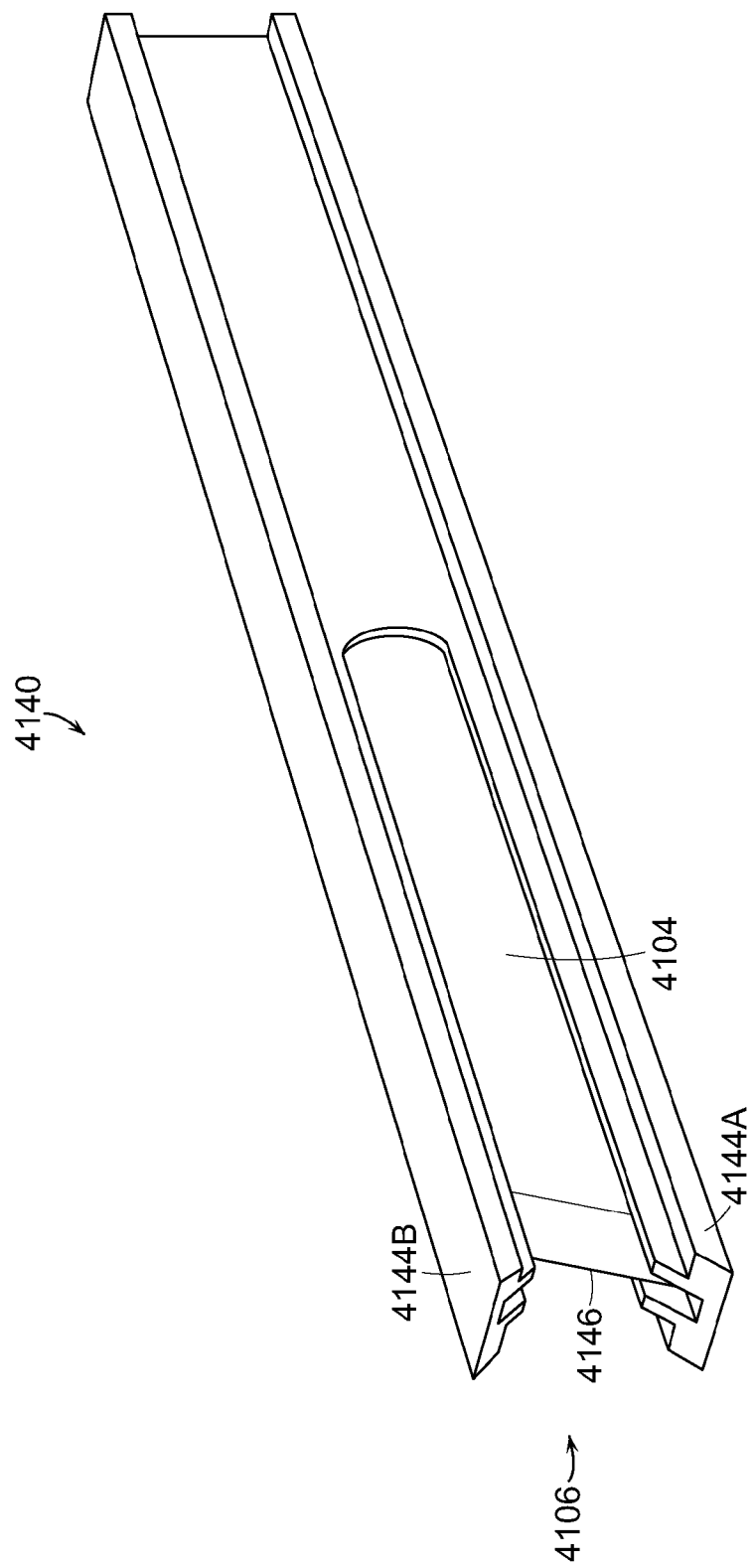
Figure 43:
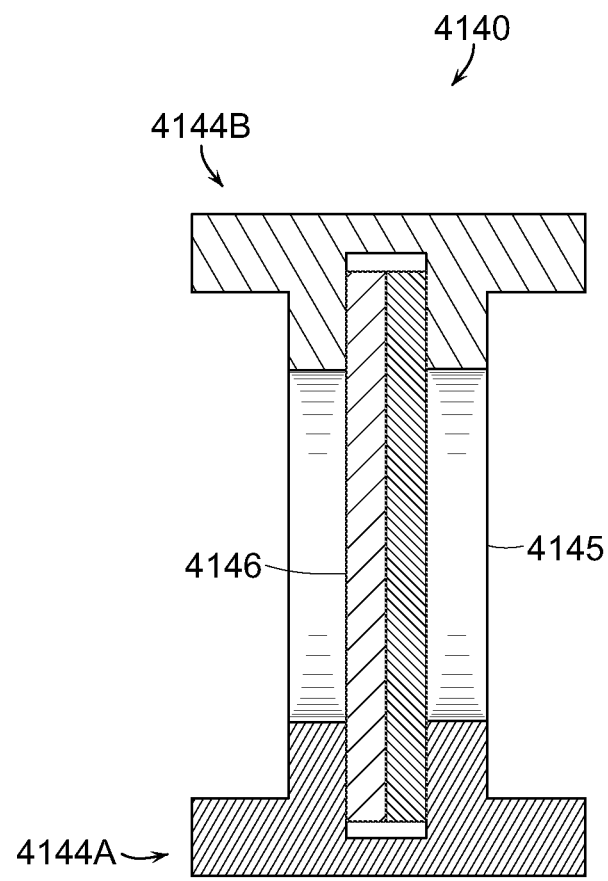

In various surgical settings, it may be desirable to close the jaw members of an end effector without cutting tissue therebetween. In this way, an end effector may be used as a grasper as well as a dissecting/sealing instrument. FIGS. 41-43 illustrate one embodiment of a reciprocating member 4140 that may be used in any of the end effectors 106, 1200, 1500, 2000, 2300, 2500, 2500' described above in order to allow closure of jaw members without the advancement of a blade. The member 4140 may comprise an I-beam member 4102 and a blade member 4104 positioned within the I-beam member. The I-beam member 4102 may comprise a transverse portion 4145 and a pair of flange portions 4144A, 4144B, for example, similar to those of reciprocating members described herein above. According to various embodiments, the I-beam member 4102 may also define a recess 4106 beginning at its distal end. The blade member 4104 may comprise a distally positioned leading edge or blade 4146. In use, the blade member 4104 and I-beam member 4102 may be separately slidable within the shaft 104 (not shown in FIG. 41). Each member 4104, 4102 may be separately controllable from the handle 102. For example, each member 4104, 4102 may be controllable from a separate motion of an actuator 113 or actuators such as a trigger, a slide, etc.

To close an end effector, the I-beam member 4102 may be pushed distally. The flange portions 4144A, 4144B may act to close and compress jaw member portions, for example, as illustrated and described with respect to FIGS. 7-8, 15-18, 20, 22 and 23-24, etc. Because of the recess 4106, tissue or other material present between jaw members may not impede distal motion of the I-beam member 4102. If the clinician decides to transect tissue or other material present between the end effector's jaw members, the clinician may cause the blade member 4104 to extend distally to the position illustrated in FIG. 42 (e.g., by actuating a handle 113 of the handle 102). The sharp leading edge 4146 (or alternatively a cutting electrode) of the blade member 4140 may transect tissue or other material as the blade member 4140 translates distally. According to various embodiments, the blade member 4104 and the I-beam member 4102 may be extended distally together, causing the reciprocating member 4140 to behave in a manner similar to the various reciprocating members described above.

According to various embodiments, the end effectors 106, 1200, 1500, 2000, 2300, 2500, 2500' may be used to cut and fasten tissue utilizing electrical energy. The examples described below are illustrated with the end effector 106. It will be appreciated, however, that similar configurations and techniques may be used with any of the end effectors described above. Referring to the end effector 106 shown in FIGS. 3-4 and 7-8, the electrodes 120, 122 of the end effector 106 may be arranged in any suitable configuration. In use, for example, tissue (not shown) may be captured between the jaw members 108, 110. RF current may flow across the captured tissue between the opposing polarity electrodes 120, 122. This may serve to join the tissue by coagulation, welding, etc. The RF current may be activated according to any suitable control method. For example, according to various embodiments, the electrodes 120, 122 may be used to implement a "power adjustment" approach, a "current-path directing" approach or an approach referred to herein as a "weld" or "fusion" approach. These various approaches are illustrated herein with reference to FIGS. 44-47, which show the walls of an example blood vessel acted upon by various RF end effectors including those using the power adjustment and current-path directing approaches from above.

Figure 44:
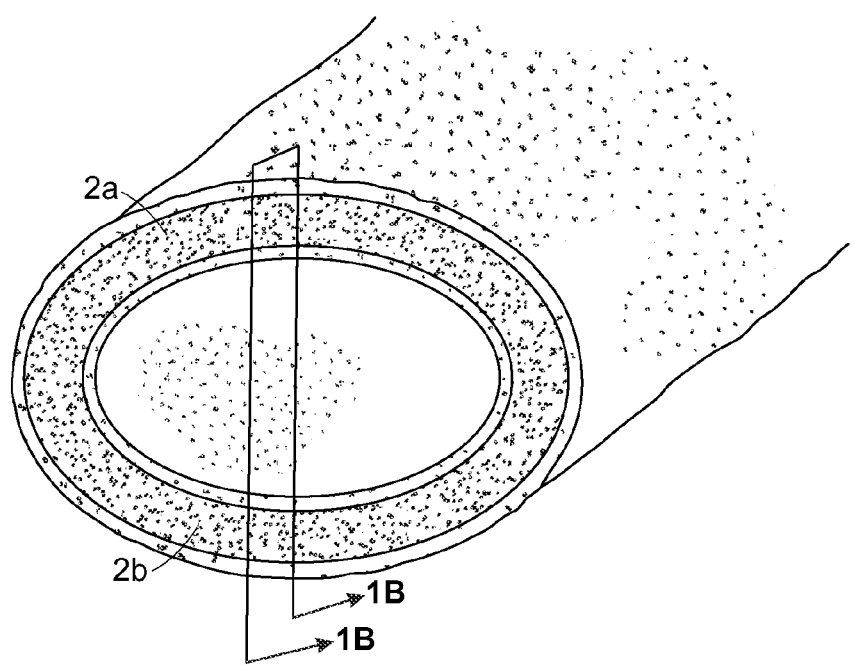
FIG. 44 shows an example embodiment of a vessel having opposing wall portions.
Figure 45:
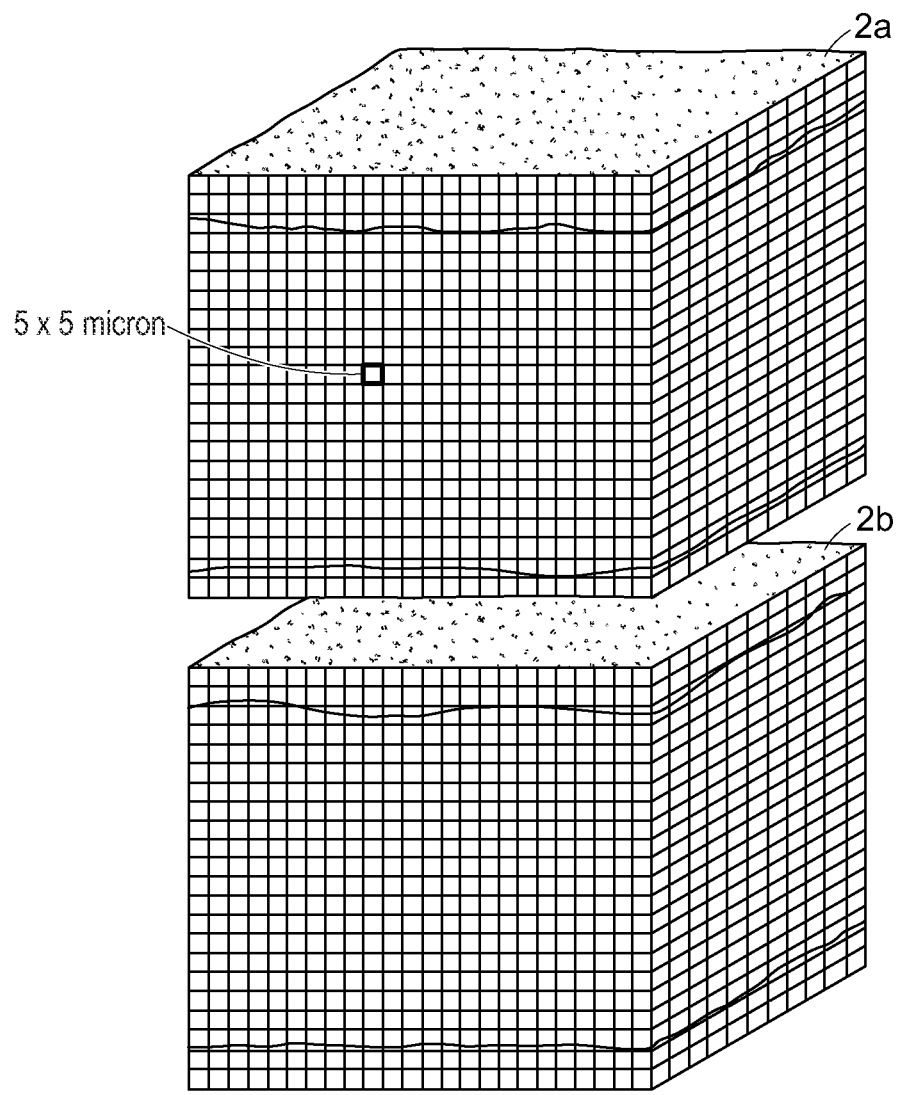
FIG. 45 is a graphic illustration of one embodiment of the opposing vessel walls portions of FIG. 44 with the tissue divided into a grid with arbitrary micron dimensions.

FIG. 44 shows an example embodiment of a vessel having opposing wall portions 2a and 2b. FIG. 45 is a graphic illustration of one embodiment of the opposing vessel walls portions 2a and 2b with the tissue divided into a grid with arbitrary micron dimensions. For example, the grid may represent 5 microns on each side of the targeted tissue. In order to coagulate or weld tissue, collagen and other protein molecules within an engaged tissue volume may be denatured by breaking the inter- and intra-molecular hydrogen bonds. When heat or other energy is removed (e.g., thermal relaxation), the molecules are re-crosslinked to create a fused-together tissue mass. It is desirable that each micron-dimensioned volume of tissue be elevated to the temperature needed to denature the proteins therein in a substantially uniform manner.

Failing to heat tissue portions in a uniform manner can lead to ohmic heating, which can create portions of tissue that are not effectively joined and reduce the strength of the joint. Non-uniformly denatured tissue volume may still be "coagulated" and can prevent blood flow in small vasculature that contains little pressure. However, such non-uniformly denatured tissue may not create a seal with significant strength, for example in 2 mm to 10 mm arteries that contain high pressures. It is often difficult to achieve substantially uniform heating with a bipolar RF device in tissue, whether the tissue is thin or thick. For example, as RF energy density in tissue increases, the tissue surface tends to become desiccated and resistant to additional ohmic heating. Localized tissue desiccation and charring can sometimes occur almost instantly as tissue impedance rises, which then can result in a non-uniform seal in the tissue. Also, many RF jaws cause further undesirable effects by propagating RF density laterally from the engaged tissue thus causing unwanted collateral thermal damage.

Figure 46:
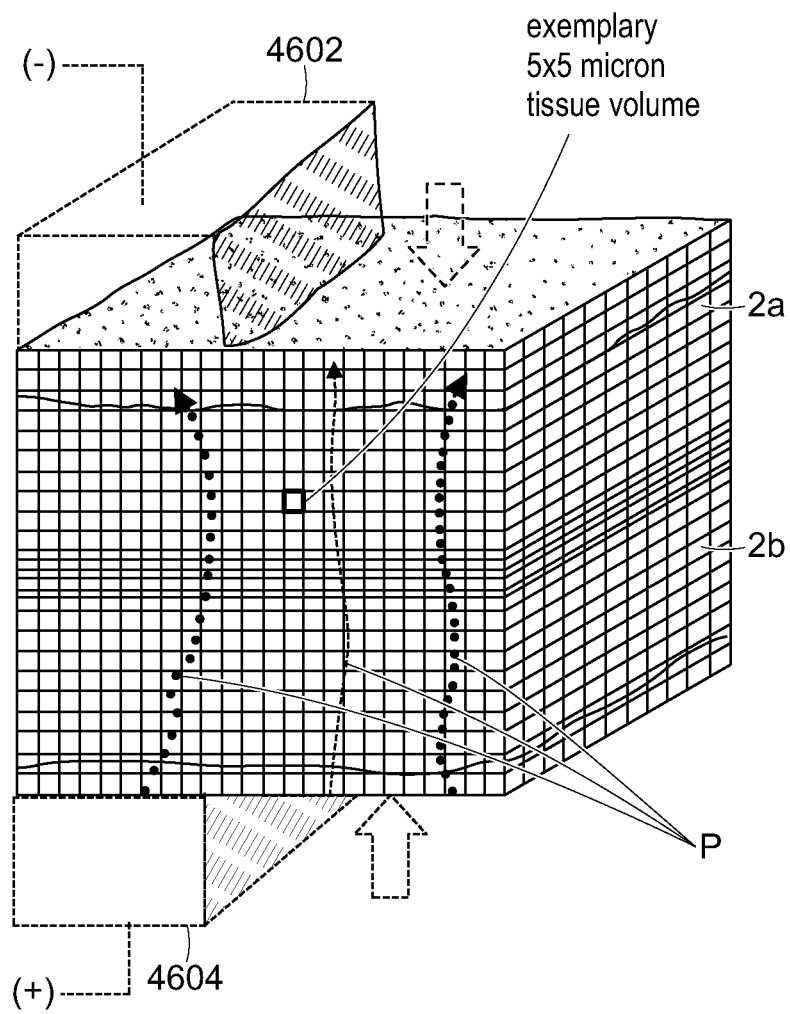
FIG. 46 illustrates one embodiment of the blood vessel of FIG. 44 acted upon by a device implementing a power adjustment approach to energy delivery.

To achieve substantially uniform coagulation, various embodiments described herein may utilize a "power adjustment" approach, a "current-path directing" approach and/or an approach referred to herein as a "weld" or "fusion" approach. According to the "power adjustment" approach, the RF generator 124 can rapidly adjust the level of total power delivered to the jaws' engagement surfaces in response to feedback circuitry, which may be present within the generator 124 and/or at the end effector 106, and may be electrically coupled to the active electrodes. The feedback circuitry may measure tissue impedance or electrode temperature. For example, temperature probes present on the jaw members 109, 110, 1202, 1204 may be in communication with the generator 123 and may sense electrode temperature. FIG. 46 illustrates one embodiment of the blood vessel of FIG. 44 acted upon by a device implementing a "power adjustment" approach to energy delivery. Opposing vessel walls 2a and 2b are shown compressed with cut-away phantom views of opposing polarity electrodes 4602, 4604 on either side of the tissue. For example, the electrode 4602 may be positioned on one jaw member 108, 110, while the electrode 4604 may be positioned on the opposite jaw member. One advantage of such an electrode arrangement is that 100% of each jaw engagement surface comprises an "active" conductor of electrical current—thus no tissue is engaged by an insulator which theoretically would cause a dead spot (no ohmic heating) proximate to the insulator.

FIG. 46 also graphically depicts current paths p in the tissue at an arbitrary time interval that can be microseconds (μs) apart. Such current paths p would be random and constantly in flux—along transient most conductive pathways through the tissue between the opposing polarity electrodes. The thickness of the paths is intended to represent the constantly adjusting power levels. Typically, the duration of energy density along any current path p is on the order of microseconds and the thermal relaxation time of tissue is on the order of milliseconds. Instruments using the power adjustment approach may be useful for sealing relatively small vessels with relatively low fluid pressure. This is because, given the spatial distribution of the current paths and the dynamic adjustment of their power levels, it is unlikely that enough random current paths will revisit and maintain each discrete micron-scale tissue volume at the targeted temperature before thermal relaxation. Also, because the hydration of tissue is constantly reduced during ohmic heating—any region of more desiccated tissue will lose its ohmic heating, rendering it unable to be "welded" to adjacent tissue volumes.

In a second "current-path directing" approach, the end effector jaws carry an electrode arrangement in which opposing polarity electrodes are spaced apart by an insulator material, which may cause current to flow within an extended path through captured tissue rather than simply between surfaces of the first and second jaws. For example, electrode configurations similar to those shown below in FIG. 47 may be implemented on tissue engaging surfaces 350*a*, 350*b*, 1236*a*, 1236*b*.

Figure 47:
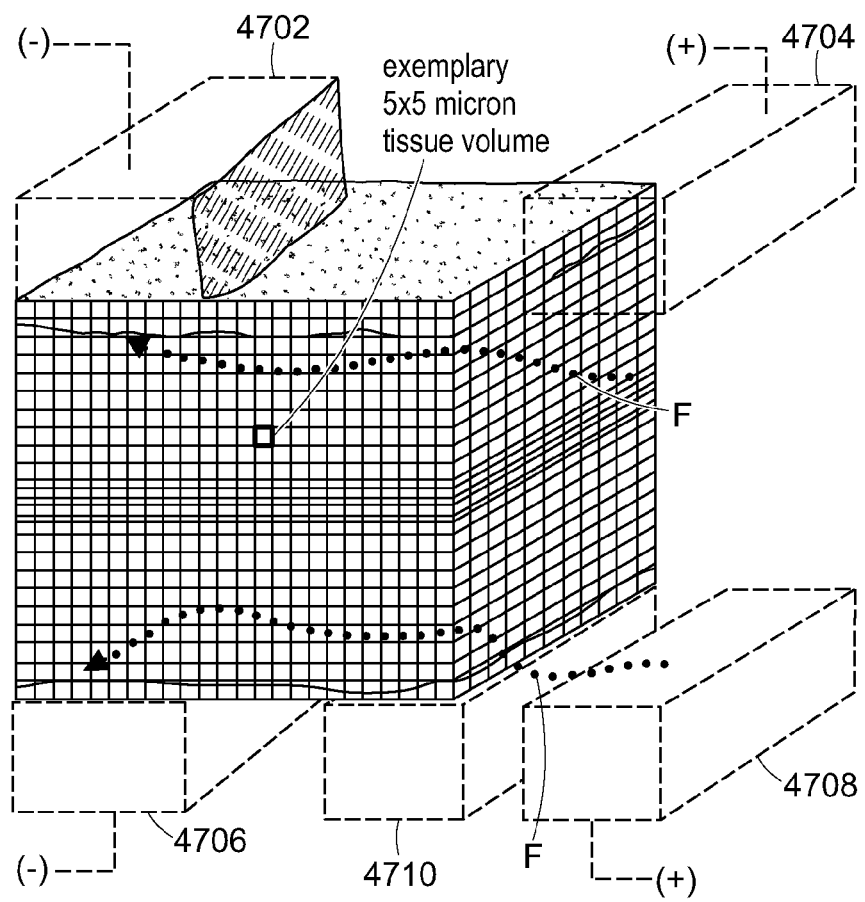
FIG. 47 illustrates one embodiment of the blood vessel of FIG. 44 acted upon by a device implementing a current-path directing approach to energy delivery.

"Current-path directing" techniques are also used to improve the quality of energy-delivered seals. FIG. 47 illustrates one embodiment of the blood vessel of FIG. 44 acted upon by a device implementing a current-path directing approach to energy delivery. In FIG. 47, vessel walls 2*a* and 2*b* are engaged between opposing jaws surfaces with cut-away phantom views of electrodes 4702, 4704, 4706, 4708, with opposing polarity (+) and (−) electrodes (4702, 4704 and 4706, 4708) on each side of the engaged tissue. For example, electrodes 4702 and 4704 may be positioned on one of the jaw members 108, 110, 1202, 1204 while electrodes 4706 and 4708 may be positioned on the opposite jaw member. An insulator 4710 is shown in cut-away view that electrically isolates the electrodes in the jaw. The tissue that directly contacts the insulator 4710 will only be ohmically heated when a current path p extends through the tissue between the spaced apart electrodes. FIG. 47 graphically depicts current paths p at any arbitrary time interval, for example in the μs range. Again, such current paths p will be random and in constant flux along transient conductive pathways.

A third approach, according to various embodiments, may be referred to as a "weld" or "fusion" approach. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. Such welds may be used in various surgical applications including, for example, (i) permanently sealing blood vessels in vessel transection procedures; (ii) welding organ margins in resection procedures; (iii) welding other anatomic ducts or lumens where permanent closure is desired; and also (iv) for performing vessel anastomosis, vessel closure or other procedures that join together anatomic structures or portions thereof.

The welding or fusion of tissue as disclosed herein may be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

A "weld," for example, may result from the thermally-induced denaturation of collagen and other protein molecules in a targeted tissue volume to create a transient liquid or gel-like proteinaceous amalgam. A selected energy density may be provided in the targeted tissue to cause hydrothermal breakdown of intra- and intermolecular hydrogen crosslinks in collagen and other proteins. The denatured amalgam is maintained at a selected level of hydration—without desiccation—for a selected time interval, which may be very brief. The targeted tissue volume may be maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

To implement the welding described above, the electrodes 120, 122 (or electrodes that are part of the other end effector embodiments described herein) may, one or both, comprise an electrically conductive portion, such as copper or another suitable metal or alloy, and a portion comprising a positive temperature coefficient (PTC) material having a selected increased resistance that differs at selected increased temperatures thereof. The PTC material may be positioned between the electrically conductive portion and any tissue to be acted upon by the end effector 106. One type of PTC material is a ceramic that can be engineered to exhibit a selected positively slope curve of temperature-resistance over a temperature range of about 37° C. to 100° C. Another type of PCT material may comprise a polymer having similar properties. The region at the higher end of such a temperature range brackets a targeted "thermal treatment range" at which tissue can be effectively welded. The selected resistance of the PTC matrix at the upper end of the temperature range may substantially terminate current flow therethrough.

In operation, it can be understood that the electrodes 120 or 122 will apply active RF energy (ohmic heating within) to the engaged tissue until the point in time that the PTC matrix is heated to exceed the maximum of the thermal treatment range. Thereafter, RF current flow from the engagement surface will be lessened—depending on the relative surface areas of the first and second electrodes 120, 122. This instant and automatic reduction of RF energy application may prevent any substantial dehydration of tissue proximate to the engagement plane. By thus maintaining an optimal level of moisture around the engagement plane, the working end can more effectively apply energy to the tissue—and provide a weld thicker tissues with limited collateral thermal effects.

Figure 48:
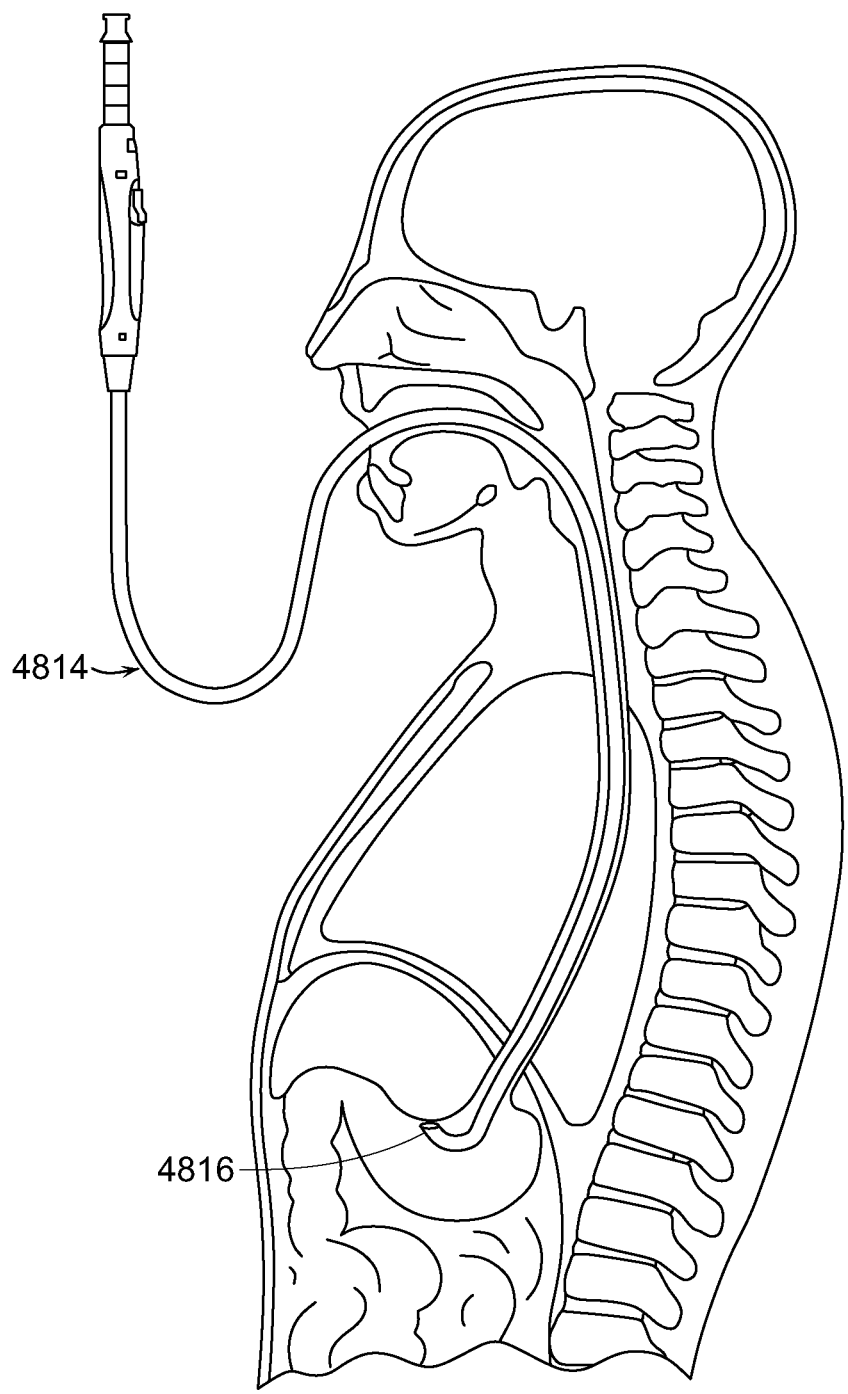
FIG. 48 illustrates one embodiment of an endoscope (illustrated here as a gastroscope) inserted into the upper gastrointestinal tract of a patient.

In various embodiments, surgical instruments utilizing various embodiments of the transection and sealing instrument 100, with the various end effectors and actuating mechanisms described herein may be employed in conjunction with a flexible endoscope. FIG. 48 illustrates one embodiment of an endoscope 4814 (illustrated here as a gastroscope) inserted into the upper gastrointestinal tract of a patient. The endoscope 4814 may be any suitable endoscope including, for example, the GIF-100 model available from Olympus Corporation. The endoscope 4814 has a distal end 4816 that may include various optical channels, illumination channels, and working channels. According to various embodiments, the endoscope 4814 may be a flexible endoscope.

Figure 49:
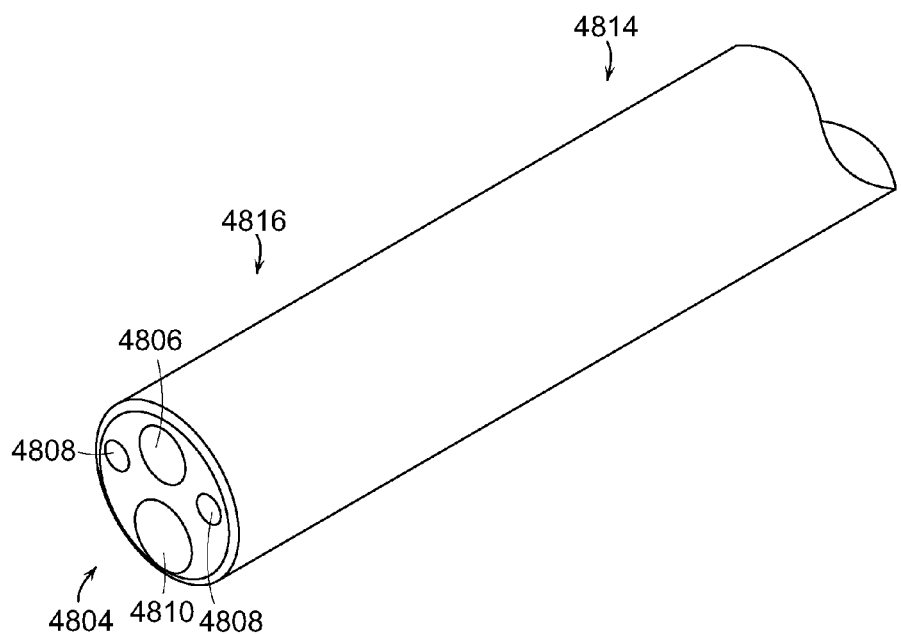
FIG. 49 illustrates one embodiment of a distal portion of the endoscope of FIG. 48, which may be used with the transection and sealing instrument described herein.

FIG. 49 illustrates one embodiment of a distal portion 4816 of the endoscope 4814, which may be used with the transection and sealing instrument 100 described herein. The example endoscope 4814 shown comprises a distal face 4804, which defines the distal ends of illumination channels 4808, an optical channel 4806 and a working channel 4810. The illumination channels 4808 may comprise one or more optical fibers or other suitable waveguides for directing light from a proximally positioned light source (not shown) to the surgical site. The optical channel 4806 may comprise one or more optical fibers or other suitable waveguides for receiving and transmitting an image of the surgical site proximally to a position where the image may be viewed by the clinician operating the endoscope 4814. As described above, the working channel 4810 may allow the clinician to introduce one or more surgical tools to the surgical site. Examples of such surgical tools include scissors, cautery knives, suturing devices, and dissectors. It will be appreciated that the endoscope 4814 is but one example of an endoscope that may be used in accordance with various embodiments. Endoscopes having alternate configurations of optical channels 4806, illumination channels 4808 and/or working channels 4810 may also be used. According to various embodiments, the endoscope 4814 may be, or may be used in conjunction with, steerable devices such as traditional flexible endoscopes or steerable overtubes as described in U.S. Patent Application Publication No. 2010/0010299, incorporated herein by reference. Combinations of flexible endoscopes and steerable overtubes may also be used in some embodiments.

In at least one such embodiment, the endoscope 4814, a laparoscope, or a thoracoscope, for example, may be introduced into the patient trans-anally through the colon, the abdomen via an incision or keyhole and a trocar, or trans-orally through the esophagus or transvaginally through the cervix, for example. These devices may assist the clinician to guide and position the transection and sealing instrument 100 near the tissue treatment region to treat diseased tissue on organs such as the liver, for example.

In one embodiment, Natural Orifice Translumenal Endoscopic Surgery (NOTES)™ techniques may be employed to introduce the endoscope 4814 and various instruments into the patient and carry out the various procedures described herein. A NOTES™ technique is a minimally invasive therapeutic procedure that may be employed to treat diseased tissue or perform other therapeutic operations through a natural opening of the patient without making incisions in the abdomen. A natural opening may be the mouth, anus, and/or vagina. Medical implantable instruments may be introduced into the patient to the target area via the natural opening. In a NOTE™ technique, a clinician inserts a flexible endoscope into one or more natural openings of the patient to view the target area, for example, using a camera. During endoscopic surgery, the clinician inserts surgical devices through one or more lumens or working channels of the endoscope 4814 to perform various key surgical activities (KSA). These KSAs include forming an anastomosis between organs, performing dissections, repairing ulcers and other wounds. Although the devices and methods described herein may be used with NOTES™ techniques, it will be appreciated that they may also be used with other surgical techniques including, for example, other endoscopic techniques, and laparoscopic techniques.

It will be appreciated that the terms "proximal" and "distal" are used herein with reference to a clinician manipulating an end of an instrument extending from the clinician to a surgical site (e.g., through a trocar, through a natural orifice or through an open surgical site). The term "proximal" refers to the portion closest to the clinician, and the term "distal" refers to the portion located away from the clinician. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

While several embodiments have been illustrated and described, and while several illustrative embodiments have been described in considerable detail, the described embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. The described embodiments are therefore intended to cover all such modifications, alterations and adaptations without departing from the scope of the appended claims.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;
U.S. Pat. No. 7,354,440, entitled ELECTROSURGICAL INSTRUMENT AND METHOD OF USE;
U.S. Pat. No. 7,311,709, entitled ELECTROSURGICAL INSTRUMENT AND METHOD OF USE;
U.S. Pat. No. 7,309,849, entitled POLYMER COMPOSITIONS EXHIBITING A PTC PROPERTY AND METHODS OF FABRICATION;
U.S. Pat. No. 7,220,951, entitled SURGICAL SEALING SURFACES AND METHODS OF USE;
U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY;

U.S. Pat. No. 7,112,201, entitled ELECTROSURGICAL INSTRUMENT AND METHOD OF USE;

U.S. Patent Application Publication No. 2010/0010299, entitled ENDOSCOPIC TRANSLUMENAL ARTICULATABLE STEERABLE OVERTUBE; and U.S. Patent Application Publication No. 2006/0111735, entitled CLOSING ASSEMBLIES FOR CLAMPING DEVICE.

Any patent, publication, or other disclosure material, in whole or in part, that is said to be incorporated by reference herein is incorporated herein only to the extent that the incorporated material does not conflict with existing definitions, statements or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the embodiments described herein will be processed before surgery. First a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the embodiments described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

What is claimed is:

1. A surgical instrument comprising:
a handle;
a shaft coupled to the handle and extending distally along a longitudinal axis;
an end effector positioned at a distal end of the shaft, wherein the end effector comprises:
a first jaw member defining a first longitudinal slot;
a second jaw member defining a second longitudinal slot, the second jaw member pivotable towards the first jaw member about a pivot point and comprising a cam pin positioned offset from the pivot point; and
a reciprocating member translatable distally and proximally parallel to the longitudinal axis through the first longitudinal slot and the second longitudinal slot, wherein a distal portion of the reciprocating member defines a blade, wherein the reciprocating member defines a cam slot for receiving the cam pin, wherein distal motion of the reciprocating member exerts a force on the cam pin such that the second jaw member pivots towards the first jaw member, and wherein proximal motion of the reciprocating member exerts a force on the cam pin such that the second jaw member pivots away from the first jaw member.

2. The surgical instrument of claim 1, wherein the first jaw member is stationary and coupled to the shaft.

3. The surgical instrument of claim 1, wherein the first jaw member is also pivotable about the pivot point and comprises a first jaw member cam pin, wherein the reciprocating member also defines a second cam slot for receiving the first jaw member cam pin, wherein the distal motion of the reciprocating member exerts a force on the first jaw member cam pin such that the first jaw member pivots towards the second jaw member, and wherein the proximal motion of the reciprocating member exerts a force on the first jaw member cam pin such that the first jaw member pivots away from the second jaw member.

4. The surgical instrument of claim 1, wherein the pivot point is a rolling pivot point.

5. The surgical instrument of claim 1, wherein the cam slot comprises a distal portion, a transition portion and a proximal portion.

6. The surgical instrument of claim 1, wherein the reciprocating member comprises a pair of flanges positioned to ride above the first and second longitudinal slots when the reciprocating member is extended distally through the first and second longitudinal slots.

7. The surgical instrument of claim 1, wherein the first jaw member further comprises a first electrode and the second jaw member further comprises a second electrode.

8. The surgical instrument of claim 7 wherein at least one of the first electrode and the second electrode comprises a first electrically conductive portion and a positive temperature coefficient (PTC) portion.

9. The surgical instrument of claim 8, wherein the PTC portion comprises at least one material selected from the group consisting of a polymer PTC material and a ceramic PTC material.

10. The surgical instrument of claim 8, wherein the PTC portion comprises a PTC material with a temperature dependent electrical resistance such that the electrical resistance of the PTC material increases to substantially eliminate current flowing through the PTC material at a predetermined temperature.

11. The surgical instrument of claim 1, wherein the first jaw member comprises a tissue engagement surface comprising a positive electrode and a negative electrode separated by an insulator.

12. A surgical instrument comprising:
a handle;
a shaft coupled to the handle and extending distally along a longitudinal axis; and
an end effector positioned at a distal end of the shaft, wherein the end effector comprises:
  a first jaw member defining a first longitudinal slot;
  a second jaw member defining a second longitudinal slot, the second jaw member pivotable relative to the first jaw member about a pivot point; and
  a reciprocating member comprising:
    an I-beam member translatable distally and proximally relative to the longitudinal axis through the first longitudinal slot and the second longitudinal slot; and
    a blade member translatable distally and proximally separately from the I-beam member.

13. The surgical instrument of claim 12, wherein the second jaw member comprises a cam pin positioned offset from the pivot point, wherein the I-beam member defines a cam slot for receiving the cam pin, wherein distal motion of the reciprocating member exerts a force on the cam pin such that the second jaw member pivots towards the first jaw member, and wherein proximal motion of the reciprocating member exerts a force on the cam pin such that the second jaw member pivots away from the first jaw member.

14. The surgical instrument of claim 13, wherein the first jaw member is also pivotable about the pivot point and comprises a first jaw member cam pin, wherein the reciprocating member defines a second cam slot for receiving the first jaw member cam pin, wherein the distal motion of the reciprocating member exerts a force on the first jaw member cam pin such that the first jaw member pivots towards the second jaw member, and wherein the proximal motion of the reciprocating member exerts a force on the first jaw member cam pin such that the first jaw member pivots away from the second jaw member.

15. The surgical instrument of claim 12, wherein the first jaw member comprises a first cam portion positioned proximally from the pivot point, the second jaw member comprises a second cam portion positioned proximally from the pivot point, the surgical instrument further comprising an overtube positioned over the shaft, wherein the overtube is translatable distally toward the pivot point, wherein the overtube is configured to contact the first and second cam portions as the overtube translates distally to apply a force on the first and second cam portions tending to close the first and second jaw members.

16. The surgical instrument of claim 12, wherein the first jaw member further comprises a first electrode and the second jaw member further comprises a second electrode.

17. The surgical instrument of claim 16 wherein at least one of the first electrode and the second electrode comprises a first electrically conductive portion and a positive temperature coefficient (PTC) portion.

18. The surgical instrument of claim 17, wherein the PTC portion comprises at least one material selected from the group consisting of a polymer PTC material and a ceramic PTC material.

19. The surgical instrument of claim 16, wherein the PTC portion comprises a PTC material with a temperature dependent electrical resistance such that the electrical resistance of the PTC material increases to substantially eliminate current flowing through the PTC material at a predetermined temperature.

20. The surgical instrument of claim 12, wherein the first jaw member comprises a tissue engagement surface comprising a positive electrode and a negative electrode separated by an insulator.

\* \* \* \* \*